(12) United States Patent
Palerm

(10) Patent No.: US 11,344,674 B2
(45) Date of Patent: May 31, 2022

(54) INFUSION DEVICES AND RELATED METHODS AND SYSTEMS FOR REGULATING INSULIN ON BOARD

(71) Applicant: MEDTRONIC MINIMED, INC., Northridge, CA (US)

(72) Inventor: Cesar C. Palerm, Pasadena, CA (US)

(73) Assignee: Medtronic MiniMed, Inc., Northridge (CA)

( * ) Notice: Subject to any disclaimer, the term of this patent is extended or adjusted under 35 U.S.C. 154(b) by 682 days.

(21) Appl. No.: 16/255,394

(22) Filed: Jan. 23, 2019

(65) Prior Publication Data
US 2019/0151543 A1 May 23, 2019

Related U.S. Application Data

(62) Division of application No. 14/261,272, filed on Apr. 24, 2014, now Pat. No. 10,232,113.

(51) Int. Cl.
*A61M 5/172* (2006.01)
*A61M 5/145* (2006.01)
(Continued)

(52) U.S. Cl.
CPC ........ *A61M 5/1723* (2013.01); *A61M 5/1452* (2013.01); *A61M 5/14244* (2013.01);
(Continued)

(58) Field of Classification Search
CPC ............ A61M 5/1723; A61M 5/14244; A61M 2005/14208; A61M 2230/201; G06F 19/3468
See application file for complete search history.

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS (Animas Corporation, 1999). Animas . . . bringing new life to insulin therapy. (Applicant points out, in accordance with MPEP 609.04(a), that the year of publication, 1999 is sufficiently earlier than the effective U.S. filing date, so that the particular month of publication is not in issue.).
(Continued)

*Primary Examiner* — Nathan R Price
*Assistant Examiner* — Melissa A Snyder
(74) *Attorney, Agent, or Firm* — Shumaker & Sieffert, P.A.

(57) ABSTRACT

Infusion systems, infusion devices, and related operating methods are provided. An exemplary method of operating an infusion device capable of delivering fluid to a user involves determining a current amount of active fluid in the body of the user, determining a threshold amount of active fluid in the body of the user, and automatically altering operation of the infusion device to modify delivery of the fluid to the user based on a relationship between the current amount and the threshold amount.

19 Claims, 22 Drawing Sheets

(51) Int. Cl.
*A61M 5/168* (2006.01)
*A61M 5/142* (2006.01)

(52) U.S. Cl.
CPC . *A61M 5/1684* (2013.01); *A61M 2005/14208* (2013.01); *A61M 2005/1726* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen |
| 4,755,173 A | 7/1988 | Konopka et al. |
| 4,781,798 A | 11/1988 | Gough |
| 4,803,625 A | 2/1989 | Fu et al. |
| 4,809,697 A | 3/1989 | Causey et al. |
| 4,826,810 A | 5/1989 | Aoki |
| 4,871,351 A | 10/1989 | Feingold |
| 4,898,578 A | 2/1990 | Rubalcab, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,522,803 A | 6/1996 | Teissen-Simony |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Martiila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,807,375 A | 9/1998 | Gross et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,954,643 A | 9/1999 | Antwerp et al. |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,017,328 A | 1/2000 | Fischell et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,259,937 B1 | 7/2001 | Schulman et al. |
| 6,329,161 B1 | 12/2001 | Heller et al. |

(56) References Cited

U.S. PATENT DOCUMENTS

| | | |
|---|---|---|
| 6,355,021 B1 | 3/2002 | Nielsen et al. |
| 6,379,301 B1 | 4/2002 | Worthington et al. |
| 6,408,330 B1 | 6/2002 | Delahuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |
| 6,484,046 B1 | 11/2002 | Say et al. |
| 6,485,465 B2 | 11/2002 | Moberg et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,544,212 B2 | 4/2003 | Galley et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,589,229 B1 | 7/2003 | Connelly et al. |
| 6,591,125 B1 | 7/2003 | Buse et al. |
| 6,591,876 B2 | 7/2003 | Safabash |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,723,046 B2 | 4/2004 | Lichtenstein et al. |
| 6,728,576 B2 | 4/2004 | Thompson et al. |
| 6,733,471 B1 | 5/2004 | Ericson et al. |
| 6,736,797 B1 | 5/2004 | Larsen et al. |
| 6,740,072 B2 | 5/2004 | Starkweather et al. |
| 6,746,582 B2 | 6/2004 | Heller et al. |
| 6,747,556 B2 | 6/2004 | Medema et al. |
| 6,749,587 B2 | 6/2004 | Flaherty |
| 6,749,740 B2 | 6/2004 | Liamos et al. |
| 6,752,787 B1 | 6/2004 | Causey, III et al. |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 6,809,653 B1 | 10/2004 | Mann et al. |
| 6,817,990 B2 | 11/2004 | Yap et al. |
| 6,827,702 B2 | 12/2004 | Lebel et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,153,263 B2 | 12/2006 | Carter et al. |
| 7,153,289 B2 | 12/2006 | Vasko |
| 7,303,549 B2 | 12/2007 | Flaherty et al. |
| 7,323,142 B2 | 1/2008 | Pendo et al. |
| 7,396,330 B2 | 7/2008 | Banet et al. |
| 7,399,277 B2 | 7/2008 | Saidara et al. |
| 7,402,153 B2 | 7/2008 | Steil et al. |
| 7,442,186 B2 | 10/2008 | Blomquist |
| 7,602,310 B2 | 10/2009 | Mann et al. |
| 7,621,893 B2 | 11/2009 | Moberg et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,257,300 B2 | 9/2012 | Budiman et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,474,332 B2 | 7/2013 | Bente, IV |
| 9,861,748 B2 | 1/2018 | Mastrototaro et al. |
| 10,232,113 B2 | 3/2019 | Palerm |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060753 A1 | 3/2003 | Starkweather et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0114836 A1 | 6/2003 | Estes et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0015132 A1 | 1/2004 | Brown |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihal et al. |

(56) References Cited

U.S. PATENT DOCUMENTS

| | | |
|---|---|---|
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmuel et al. |
| 2007/0123819 A1 | 5/2007 | Mernoe et al. |
| 2007/0135866 A1 | 6/2007 | Baker et al. |
| 2008/0154503 A1 | 6/2008 | Wittenber et al. |
| 2009/0058635 A1 | 3/2009 | Lalonde et al. |
| 2009/0081951 A1 | 3/2009 | Erdmann et al. |
| 2009/0082635 A1 | 3/2009 | Baldus et al. |
| 2010/0057042 A1 | 3/2010 | Hayter |
| 2010/0160861 A1 | 6/2010 | Causey, III et al. |
| 2011/0021990 A1 | 1/2011 | Navarro et al. |
| 2011/0208155 A1* | 8/2011 | Palerm .................. G16H 20/17 604/503 |
| 2011/0233393 A1 | 9/2011 | Hanson et al. |
| 2014/0066889 A1 | 3/2014 | Grosman et al. |
| 2019/0290843 A1 | 9/2019 | Bazargan et al. |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 9620745 | 7/1996 |
| WO | WO 9636389 | 11/1996 |
| WO | WO 9637246 A1 | 11/1996 |
| WO | WO 9721456 | 6/1997 |
| WO | WO 9820439 | 5/1998 |
| WO | WO 9824358 | 6/1998 |
| WO | WO 9842407 | 10/1998 |
| WO | WO 9849659 | 11/1998 |
| WO | WO 9859487 | 12/1998 |
| WO | WO 9908183 | 2/1999 |
| WO | WO 9910801 | 3/1999 |
| WO | WO 9918532 | 4/1999 |
| WO | WO 9922236 | 5/1999 |
| WO | WO 0010628 | 3/2000 |
| WO | WO 0019887 | 4/2000 |
| WO | WO 0048112 | 8/2000 |
| WO | WO 02058537 | 8/2002 |
| WO | WO 03001329 | 1/2003 |
| WO | WO 03094090 | 11/2003 |
| WO | WO 2005065538 | 7/2005 |

OTHER PUBLICATIONS (Intensive Diabetes Management, 1995). Insulin Infusion Pump Therapy. pp. 66-78. (Applicant points out, in accordance with MPEP 609.04(a), that the year of publication, 1995 is sufficiently earlier than the effective U.S. filing date, so that the particular month of publication is not in issue.).

(Medtronic MiniMed, 2002). Medtronic MiniMed Meal Bolus Calculator and Correction Bolus Calculator. International Version. (Applicant points out, in accordance with MPEP 609.04(a), that the year of publication, 2002 is sufficiently earlier than the effective U.S. filing date, so that the particular month of publication is not in issue.).

(Medtronic MiniMed, 2002). The 508 Insulin Pump A Tradition of Excellence. Applicant points out, in accordance with MPEP 609.04(a), that the year of publication, 2002 is sufficiently earlier than the effective U.S. filing date, so that the particular month of publication is not in issue.).

(MiniMed Inc. 1999). MiniMed 508 Flipchart Guide to Insulin Pump Therapy. (Applicant points out, in accordance with MPEP 609.04(a), that the year of publication, 1999 is sufficiently earlier than the effective U.S. filing date, so that the particular month of publication is not in issue.).

(MiniMed Inc., 1999). Insulin Pump Comparison I Pump Therapy Will Change Your Life. (Applicant points out, in accordance with MPEP 609.04(a), that the year of publication, 1999 is sufficiently earlier than the effective U.S. filing date, so that the particular month of publication is not in issue.).

(MiniMed Inc., 2000). MiniMed® Now [I] Can Meal Bolus Calculator I MiniMed® Now [I] Can Correction Bolus Calculator. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Diabetes Management. (Applicant points out, in accordance with MPEP 609.04(a), that the year of publication, 2000 is sufficiently earlier than the effective U.S. filing date, so that the particular month of publication is not in issue.).

(MiniMed Inc., 2000). Now [I] Can MiniMed Pump Therapy. (Applicant points out, in accordance with MPEP 609.04(a), that the year of publication, 2000 is sufficiently earlier than the effective U.S. filing date, so that the particular month of publication is not in issue.).

(MiniMed International, 1998). MiniMed 507C Insulin Pump For those who appreciate the difference. (Applicant points out, in accordance with MPEP 609.04(a), that the year of publication, 1998 is sufficiently earlier than the effective U.S. filing date, so that the particular month of publication is not in issue.).

(MiniMed Technologies, 1994). MiniMed 506 Insulin Pump User's Guide. (Applicant points out, in accordance with MPEP 609.04(a), that the year of publication, 1994 is sufficiently earlier than the effective U.S. filing date, so that the particular month of publication is not in issue.).

(MiniMed Technologies, 1994). MiniMedrM Dosage Calculator Initial Meal Bolus Guidelines I MiniMed™ Dosage Calculator Initial Basal Rate Guidelines Percentage Method. 4 pages. (Applicant points out, in accordance with MPEP 609.04(a), that the year of publication, 1994 is sufficiently earlier than the effective U.S. filing date, so that the particular month of publication is not in issue.).

(Minimed, 1996). FAQ: The Practical Things . . . pp. 1-4. Retrieved on Sep. 16, 2003 from the WOrld Wide Web: http://web.archive.orglwebl19961111054546/www.minimed.com/fileslfaq_pract.htm. Applicant points out, in accordance with MPEP 609.04(a), that the year of publication, 1996 is sufficiently earlier than the effective U.S. filing date, so that the particular month of publication is not in issue.).

(Minimed, 1996). MiniMedTM 507Insulin Pump User's Guide. (Applicant points out, in accordance with MPEP 609.04(a), that the year of publication, 1996 is sufficiently earlier than the effective U.S. filing date, so that the particular month of publication is not in issue.).

(Minimed, 1996). The MiniMed 506. 7 pages. Retrieved on Sep. 16, 2003 from the WOrld Wide Web: http:/lweb.archive.orglweb/19961111054527/www.minimed.comlfiles/506_pic.htm.

(Minimed, 1997). MiniMed 507 Specifications. 2 pages. Retrieved on Sep. 16, 2003 from the WOrld Wide Web: http://web.archive.org/web/19970124234841www.minimed.comlfileslmmm075.htm.

(Minimed, 1997). MiniMedrM 507 Insulin Pump User's Guide. (Applicant points out, in accordance with MPEP 609.04(a), that the year of publication, 1997 is sufficiently earlier than the effective U.S. filing date, so that the particular month of publication is not in issue.).

(Minimed, 1997). Wanted: a Few Good Belt Clips! 1 page. Retrieved on Sep. 16, 2003 from the WOrld Wide Web: http:l/web.archive.orglwebl19970124234559lwww.minimed.comlfileslmmm002.htm.

(Minimed, 1998). MiniMed 507C Insulin Pump User's Guide. (Applicant points out, in accordance with MPEP 609.04(a), that the year of publication, 1998 is sufficiently earlier than the effective U.S. filing date, so that the particular month of publication is not in issue.).

(56) References Cited

OTHER PUBLICATIONS (Minimed, 2000). MiniMed® 508 User's Guide. (Applicant points out, in accordance with MPEP 609.04(a), that the year of publication, 2000 is sufficiently earlier than the effective U.S. filing date, so that the particular month of publication is not in issue.).

Abel, P., et al., "Experience with an implantable glucose sensor as a prerequiste of an artificial beta cell," Biomed. Biochim. Acta 43 (1984) 5, pp. 577-584. (Applicant points out, in accordance with MPEP 609.04(a), that the year of publication, 1984 is sufficiently earlier than the effective U.S. filing date, so that the particular month of publication is not in issue.).

Bindra, Dilbir S., et al., "Design and in Vitro Studies of a Needle-Type Glucose Sensor for a Subcutaneous Monitoring," American Chemistry Society, 1991, 63, pp. 1692-1696. (Applicant points out, in accordance with MPEP 609.04(a), that the year of publication, 1991 is sufficiently earlier than the effective U.S. filing date, so that the particular month of publication is not in issue.).

Bode B W, et al. (1996). Reduction in Severe Hypoglycemia with Long-Term Continuous Subcutaneous Insulin Infusion in Type I Diabetes. Diabetes Care, vol. 19, No. 4, 324-327. (Applicant points out, in accordance with MPEP 609.04(a), that the year of publication, 1984 is sufficiently earlier than the effective U.S. filing date, so that the particular month of publication is not in issue.).

Boguslavsky, Leonid, et al., "Applications of redox polymers in biosensors," Sold State Ionics 60, 1993, pp. 189-197. (Applicant points out, in accordance with MPEP 609.04(a), that the year of publication, 1993 is sufficiently earlier than the effective U.S. filing date, so that the particular month of publication is not in issue.).

Boland E (1998). Teens Pumping it Up! Insulin Pump Therapy Guide for Adolescents. 2nd Edition. (Applicant points out, in accordance with MPEP 609.04(a), that the year of publication, 1998 is sufficiently earlier than the effective U.S. filing date, so that the particular month of publication is not in issue.).

Brackenridge B P (1992). Carbohydrate Gram Counting A Key to Accurate Mealtime Boluses in Intensive Diabetes Therapy. Practical Diabetology, vol. 11, No. 2, pp. 22-28. (Applicant points out, in accordance with MPEP 609.04(a), that the year of publication, 1992 is sufficiently earlier than the effective U.S. filing date, so that the particular month of publication is not in issue.).

Brackenridge, B P et al. (1995). Counting Carbohydrates How to Zero in on Good Control. MiniMed Technologies Inc. (Applicant points out, in accordance with MPEP 609.04(a), that the year of publication, 1995 is sufficiently earlier than the effective U.S. filing date, so that the particular month of publication is not in issue.).

Disetronic H-TRON® plus Quick Start Manual, (no date).

Disetronic H-TRON®plus Reference Manual, (no date).

Disetronic My Choice H-TRONplus Insulin Pump Reference Manual, (no date).

Disetronic My Choice™ D-TRONTM Insulin Pump Reference Manual, (no date).

Farkas-Hirsch Ret al. (1994). Continuous Subcutaneous Insulin Infusion: A Review of the Past and Its Implementation for the Future. Diabetes Spectrum From Research to Practice, vol. 7, No. 2, pp. 80-84, 136-138. Applicant points out, in accordance with MPEP 609.04(a), that the year of publication, 1994 is sufficiently earlier than the effective U.S. filing date, so that the particular month of publication is not in issue.).

Geise, Robert J., et al., "Eiectropolymerized 1,3-diaminobenzene for the construction of a 1,1'-dimethylferrocene mediated glucose biosensor," Analytica Chimica Acta, 2B1, 1993, pp. 467-473. (Applicant points out, in accordance with MPEP 609.04(a), that the year of publication, 1993 is sufficiently earlier than the effective U.S. filing date, so that the particular month of publication is not in issue.).

Gernet, S., et al., "A Planar Glucose Enzyme Electrode," Sensors and Actuators, 17, 1989, pp. 537-540. (Applicant points out, in accordance with MPEP 609.04(a), that the year of publication, 1989 is sufficiently earlier than the effective U.S. filing date, so that the particular month of publication is not in issue.).

Gernet, S., et al., "Fabrication and Characterization of a Planar Electromechanical Cell and its Application as a Glucose Sensor," Sensors and Actuators, 18, 1989, pp. 59-70. (Applicant points out, in accordance with MPEP 609.04(a), that the year of publication, 1989 is sufficiently earlier than the effective U.S. filing date, so that the particular month of publication is not in issue.).

Gorton, L., et al., "Amperometric Biosensors Based on an Apparent Direct Electron Transfer Between Electrodes and Immobilized Peroxiases," Analyst, Aug. 1991, vol. 117, pp. 1235-1241. (Applicant points out, in accordance with MPEP 609.04(a), that the year of publication, 1991 is sufficiently earlier than the effective U.S. filing date, so that the particular month of publication is not in issue.).

Gorton, L., et al., "Amperometric Glucose Sensors Based on Immobilized Glucose-Oxidizing Enymes and Chemically Modified Electrodes," Analytica Chimica Acta, 249, 1991, pp. 43-54. (Applicant points out, in accordance with MPEP 609.04(a), that the year of publication, 1991 is sufficiently earlier than the effective U.S. filing date, so that the particular month of publication is not in issue.).

Gough, D. A., et al., "TWO-Dimensional Enzyme Electrode Sensor for Glucose," Analytical Chemistry, vol. 57, No. 5, 1985, pp. 2351-2357. (Applicant points out, in accordance with MPEP 609.04(a), that the year of publication, 1985 is sufficiently earlier than the effective U.S. filing date, so that the particular month of publication is not in issue.).

Gregg, Brian A., et al., "Cross-Linked Redox Gels Containing Glucose Oxidase for Amperometric Biosensor Applications," Analytical Chemistry, 62, Feb. 1990, pp. 258-263.

Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975. (Applicant points out, in accordance with MPEP 609.04(a), that the year of publication, 1991 is sufficiently earlier than the effective U.S. filing date, so that the particular month of publication is not in issue.).

Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.

Heller, Adam, "Electrical Wiring of Redox Enzymes," Ace. Chern. Res., vol. 23, No. 5, May 1990, pp. 128-134.

Hirsch I B et al. (1990). Intensive Insulin Therapy for Treatment of Type I Diabetes. Diabetes Care, vol. 13, No. 12, pp. 1265-1283. (Applicant points out, in accordance with MPEP 609.04(a), that the year of publication, 1990 is sufficiently earlier than the effective U.S. filing date, so that the particular month of publication is not in issue.).

Jobst, Gerhard, et al., "Thin-Film Microbiosensors for Glucose-Lactate Monitoring," Analytical Chemistry, vol. 68, No. 18, Sep. 15, 1996, pp. 3173-3179.

Johnson, K.W., et al., "In vivo evaluation of an electroenzymatic glucose sensor implanted in subcutaneous tissue," Biosensors & Bioelectronics, 7, 1992, pp. 709-714. (Applicant points out, in accordance with MPEP 609.04(a), that the year of publication, 1992 is sufficiently earlier than the effective U.S. filing date, so that the particular month of publication is not in issue.).

Jonsson, G., et al., "An Electromechanical Sensor for Hydrogen Peroxide Based on Peroxidase Adsorbed on a Spectrographic Graphite Electrode," Electroanalysis, 1989, pp. 465-468. (Applicant points out, in accordance with MPEP 609.04(a), that the year of publication, 1989 is sufficiently earlier than the effective U.S. filing date, so that the particular month of publication is not in issue.).

Kanapieniene, J. J., et al., "Miniature Glucose Biosensor with Extended Linearity," Sensors and Actuators, B. 10, 1992, pp. 37-40. (Applicant points out, in accordance with MPEP 609.04(a), that the year of publication, 1992 is sufficiently earlier than the effective U.S. filing date, so that the particular month of publication is not in issue.).

(56) References Cited

OTHER PUBLICATIONS

Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52. (Applicant points out, in accordance with MPEP 609.04(a), that the year of publication, 1988 is sufficiently earlier than the effective U.S. filing date, so that the particular month of publication is not in issue.).
Koudelka, M., et al., "In-vivo Behaviour of Hypodermically Implanted Microfabricated Glucose Sensors," Biosensors & Bioelectronics 6, 1991, pp. 31-36. (Applicant points out, in accordance with MPEP 609.04(a), that the year of publication, 1991 is sufficiently earlier than the effective U.S. filing date, so that the particular month of publication is not in issue.).
Koudelka, M., et al., "Planar Amperometric Enzyme-Based Glucose Microelectrode," Sensors & Actuators, 18, 1989, pp. 157-165. (Applicant points out, in accordance with MPEP 609.04(a), that the year of publication, 1991 is sufficiently earlier than the effective U.S. filing date, so that the particular month of publication is not in issue.).
Kulkarni Ket al. (1999). Carbohydrate Counting A Primer for Insulin Pump Users to Zero in on Good Control. MiniMed Inc. (Applicant points out, in accordance with MPEP 609.04(a), that the year of publication, 1999 is sufficiently earlier than the effective U.S. filing date, so that the particular month of publication is not in issue.).
Marcus A 0 et al. (1996). Insulin Pump Therapy Acceptable Alternative to Injection Therapy. Postgraduate Medicine, vol. 99, No. 3, pp. 125-142. (Applicant points out, in accordance with MPEP 609.04(a), that the year of publication, 1996 is sufficiently earlier than the effective U.S. filing date, so that the particular month of publication is not in issue.).
Mastrototaro, John J., et al. "An electroenzymatic glucose sensor fabricated on a flexible substrate," Sensors & Actuators, B. 5,1991, pp. 139-144. (Applicant points out, in accordance with MPEP 609.04(a), that the year of publication, 1991 is sufficiently earlier than the effective U.S. filing date, so that the particular month of publication is not in issue.).
Mastrototaro, John J., et al., "An Electroenzymatic Sensor Capable of 72 Hour Continuous Monitoring of Subcutaneous Glucose," 14th Annual International Diabetes Federation Congress, Washington D.C.. Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," AnnuaalInternational Conference ofteh IEEE Engineering in Medicine and Biology Society, Vo. 12, No. 2, 1990, pp. 483-484. (Applicant points out, in accordance with MPEP 609.04(a), that the year of publication, 1999 is sufficiently earlier than the effective U.S. filing date, so that the particular month of publication is not in issue.).
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.
Nakamoto, S., et al., "A Lift-Off Method for Patterning Enzyme-Immobilized Membranes in Multi-Biosensors," Sensors and Actuators 13, 1988, pp. 165-172. (Applicant points out, in accordance with MPEP 609.04(a), that the year of publication, 1988 is sufficiently earlier than the effective U.S. filing date, so that the particular month of publication is not in issue.).
Nishida, Kenro, et al., "Clinical applications often wearable artificial endocrine pancreas with the newly designed needle-type glucose sensor," Elsevier Sciences B.V., 1994, pp. 353-358. (Applicant points out, in accordance with MPEP 609.04(a), that the year of publication, 1994 is sufficiently earlier than the effective U.S. filing date, so that the particular month of publication is not in issue.).
Nishida, Kenro, et al., "Development of a ferrocene-mediated needle-type glucose sensor covered with newly designed biocompatible membrane, 2-methacryloyloxyethylphosphorylcholine-co-n-butyl methacrylate," Medical Progress Through Technology, vol. 21, 1995, pp. 91-103. (Applicant points out, in accordance with MPEP 609.04(a), that the year of publication, 1995 is sufficiently earlier than the effective U.S. filing date, so that the particular month of publication is not in issue.).
Poitout, V., et al., "A glucose monitoring system for on line estimation on man of blood glucose concentration using a miniaturized glucose sensor implanted in the subcutaneous tissue and a wearable control unit," Diabetologia, vol. 36, published Jul. 1993, pp. 658-663.
Reach, G., "A Method for Evaluating in vivo the Functional Characteristics of Glucose Sensors," Biosensors 2, 1986, pp. 211-220. (Applicant points out, in accordance with MPEP 609.04(a), that the year of publication, 1986 is sufficiently earlier than the effective U.S. filing date, so that the particular month of publication is not in issue.).
Reed J et al. (1996). Voice of the Diabetic, vol. 11, No. 3, pp. 1-38. (Applicant points out, in accordance with MPEP 609.04(a), that the year of publication, 1986 is sufficiently earlier than the effective U.S. filing date, so that the particular month of publication is not in issue.).
Shaw, G. W., et al., "In vitro testing of a simply constructed, highly stable glucose sensor suitable for implantation in diabetic patients," Biosensors & Bioelectronics 6, 1991, pp. 401-406. (Applicant points out, in accordance with MPEP 609.04(a), that the year of publication, 1991 is sufficiently earlier than the effective U.S. filing date, so that the particular month of publication is not in issue.).
Shichiri, M., "A Needle-Type Glucose Sensor—A Valuable Tool Not Only For a Self-Blood Glucose Monitoring but for a Wearable Artificial Pancreas," Life Support Systems Proceedings, XI Annual Meeting ESAO, Alpbach-lnnsbruck, Austria, Sep. 1984, pp. 7-9.
Shichiri, M., et al., "In Vivo Characteristics of Needle-Type Glucose Sensor-Measurements of Subcutaneous Glucose Concentrations in Human Volunteers," Hormone and Metabolic Research, Supplement Series vol. No. 20, 1988, pp. 17-20. (Applicant points out, in accordance with MPEP 609.04(a), that the year of publication, 1998 is sufficiently earlier than the effective U.S. filing date, so that the particular month of publication is not in issue.).
Shichiri, M., et al., "Membrane design for extending the long-life of an implantable glucose sensor," Diab. Nutr. Metab., vol. 2, No. 4, 1989, pp. 309-313. (Applicant points out, in accordance with MPEP 609.04(a), that the year of publication, 1991 is sufficiently earlier than the effective U.S. filing date, so that the particular month of publication is not in issue.).
Shichiri, Motoaki, et al., "An artificial endocrine pancreas-problems awaiting solution for long-term clinical applications of a glucose sensor," Frontiers Med. Bioi. Engng., 1991, vol. 3, No. 4, pp. 283-292. (Applicant points out, in accordance with MPEP 609. 04(a), that the year of publication, 1998 is sufficiently earlier than the effective U.S. filing date, so that the particular month of publication is not in issue.).
Shichiri, Motoaki, et al., "Closed-Loop Glycemic Control with a Wearable Artificial Endocrine Pancreas-Variations in Daily Insulin Requirements to Glycemic Response," Diabetes, vol. 33, Dec. 1984, pp. 1200-1202.
Shichiri, Motoaki, et al., "Giycaemic Control in a Pacreatectomized Dogs with a Wearable Artificial Endocrine Pancreas," Diabetologia, vol. 24, 1983, pp. 179-184. (Applicant points out, in accordance with MPEP 609.04(a), that the year of publication, 1983 is sufficiently earlier than the effective U.S. filing date, so that the particular month of publication is not in issue.).
Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

(56) References Cited

OTHER PUBLICATIONS

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.
Shichiri, Motoaki, et al., "The Wearable Artificial Endocrine Pancreas with a Needle-Type Glucose Sensor: Perfect Glycemic Control in Ambulatory Diabetes," Acta Paediatr Jpn, Dec. 1984, vol. 26, pp. 359-370.
Shichiri, Motoaki, et al., "Wearable Artificial Endocrine Pancreas with Needle-Type Glucose Sensor," The Lancet, Nov. 20, 1992, pp. 1129-1131.
Shinkai, Seiji, "Molecular Recognitiion of Mono- and Disaccharides by Phenylboronic Acids in Solvent Extraction and as a Monolayer," J. Chem. Soc., Chem. Commun., 1991, pp. 1039-1041. (Applicant points out, in accordance with MPEP 609.04(a), that the year of publication, 1991 is sufficiently earlier than the effective U.S. filing date, so that the particular month of publication is not in issue.).
Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.
Skyler J S, "Continuous Subcutaneous Insulin Infusion [CSII] With External Devices: Current Status. Update in Drug Delivery Systems," Chapter 13, pp. 163-183, 1989, Futura Publishing Company. (Applicant points out, in accordance with MPEP 609.04(a), that the year of publication, 1989 is sufficiently earlier than the effective U.S. filing date, so that the particular month of publication is not in issue.).
Skyler J S et al. (1995). The Insulin Pump Therapy Book Insights from the Experts. MiniMed Technologies, (Applicant points out, in accordance with MPEP 609.04(a), that the year of publication, 1995 is sufficiently earlier than the effective U.S. filing date, so that the particular month of publication is not in issue.).
Sternberg, Robert, et al., "Study and Development of Multilayer Needle-type Enzyme-based Glucose Microsensors," Biosensors, vol. 4, 1988, pp. 27-40. (Applicant points out, in accordance with MPEP 609.04(a), that the year of publication, 1988 is sufficiently earlier than the effective U.S. filing date, so that the particular month of publication is not in issue.).
Strowig S M (1993). Initiation and Management of Insulin Pump Therapy. The Diabetes Educator, vol. 19, No. 1, pp. 50-60. (Applicant points out, in accordance with MPEP 609.04(a), that the year of publication, 1993 is sufficiently earlier than the effective U.S. filing date, so that the particular month of publication is not in issue.).
Tamiya, E., et al., "Micro Glucose Sensors using Electron Mediators Immobilized on a Polypyrrole-Modified Electrode," Sensors and Actuators, vol. 18, 1989, pp. 297-307. (Applicant points out, in accordance with MPEP 609.04(a), that the year of publication, 1989 is sufficiently earlier than the effective U.S. filing date, so that the particular month of publication is not in issue.).
Tsukagoshi, Kazuhiko, et al., "Specific Complexation with Mono- and Disaccharides that can be Detected by Circular Dichroism," J. Org. Chem., vol. 56, 1991, pp. 4089-4091. (Applicant points out, in accordance with MPEP 609.04(a), that the year of publication, 1991 is sufficiently earlier than the effective U.S. filing date, so that the particular month of publication is not in issue.).
Ubran, G., et al., "Miniaturized thin-film biosensors using covalently immobilized glucose oxidase," Biosensors & Bioelectronics, vol. 6, 1991, pp. 555-562. (Applicant points out, in accordance with MPEP 609.04(a), that the year of publication, 1991 is sufficiently earlier than the effective U.S. filing date, so that the particular month of publication is not in issue.).
Urban, G., et al., "Miniaturized multi-enzyme biosensors integrated with pH sensors on flexible polymer carriers for in vivo applications," Biosensors & Bioelectronics, vol. 7, 1992, pp. 733-739. (Applicant points out, in accordance with MPEP 609.04(a), that the year of publication, 1992 is sufficiently earlier than the effective U.S. filing date, so that the particular month of publication is not in issue.).
Velho, G., et al., "In vivo calibration of a subcutaneous glucose sensor for determination of subcutaneous glucose kinetics," Diab. Nutr. Metab., vol. 3, 1988, pp. 227-233. (Applicant points out, in accordance with MPEP 609.04(a), that the year of publication, 1988 is sufficiently earlier than the effective U.S. filing date, so that the particular month of publication is not in issue.).
Walsh J, et al. (1989). Pumping Insulin: The Art of Using an Insulin Pump. Published by MiniMed Technologies. (Applicant points out, in accordance with MPEP 609.04(a), that the year of publication, 1989 is sufficiently earlier than the effective U.S. filing date, so that the particular month of publication is not in issue.).
Wang, Joseph, et al., "Needle-Type Dual Microsensor for the Simultaneous Monitoring of Glucose and Insulin," Analytical Chemistry, vol. 73, 2001, pp. 844-847. Applicant points out, in accordance with MPEP 609.04(a), that the year of publication, 2001 is sufficiently earlier than the effective U.S. filing date, so that the particular month of publication is not in issue.).
Yamasaki, Yoshimitsu, et al., "Direct Measurement of Whole Blood Glucose by a Needle-Type Sensor," Clinics Chimica Acta, vol. 93, 1989, pp. 93-98. (Applicant points out, in accordance with MPEP 609.04(a), that the year of publication, 1989 is sufficiently earlier than the effective U.S. filing date, so that the particular month of publication is not in issue.).
Yokoyama, K., "Integrated Biosensor for Glucose and Galactose," Analytica Chimica Acta, vol. 218, 1989 pp. 137-142 (Applicant points out, in accordance with MPEP 609.04(a), that the year of publication, 1989 is sufficiently earlier than the effective U.S. filing date, so that the particular month of publication is not in issue.).
International Search Report from International Application No. PCT/US2002/03299, dated Dec. 31, 2002.
International Preliminary Examination Report from International Application No. PCT/US2002/03299, dated Jan. 22, 2003, 2 pp.
Prosecution History from U.S. Appl. No. 14/261,272, from Jan. 13, 2017 through Nov. 29, 2018, 83 pp.

* cited by examiner

| $y_{t-8}$ | $y_{t-7}$ | $y_{t-6}$ | $y_{t-5}$ | $y_{t-4}$ | $y_{t-3}$ | $y_{t-2}$ | $y_{t-1}$ | $y_t$ |
|---|---|---|---|---|---|---|---|---|
| 1 | 1.5 | 2 | 2.5 | 3 | 3.5 | 4 | 4.5 | 5 |
| 1 | NULL | 2 | 2.5 | 3 | NULL | NULL | NULL | 3.5 |
| 1 | NULL | 1.5 | 2 | 2.5 | NULL | NULL | 4 | 5 |
| NULL | NULL | NULL | 2.5 | 3 | 3.5 | 4 | 4.5 | 5 |
| 1 | 1.5 | 2 | NULL | NULL | NULL | NULL | 4.5 | 5 |
| NULL | NULL | NULL | NULL | 3 | 3.5 | 4 | 4.5 | 5 |
| NULL | NULL | 2 | NULL | NULL | 3 | 3 | 2.75 | 2.5 |

FIG. 9

| $y_{t-8}$ | $y_{t-7}$ | $y_{t-6}$ | $y_{t-5}$ | $y_{t-4}$ | $y_{t-3}$ | $y_{t-2}$ | $y_{t-1}$ | $y_t$ | $\hat{y}$ |
|---|---|---|---|---|---|---|---|---|---|
| 1 | 1.5 | 2 | 2.5 | 3 | 3.5 | 4 | 4.5 | 5 | 7.59 |
| 1 | 1.5 | 2 | 2.5 | 3 | 3.13 | 3.25 | 3.38 | 3.5 | 4.67 |
| 1 | 1.25 | 1.5 | 2 | 2.5 | 3 | 3.5 | 4 | 5 | 8.12 |
| 1.38 | 1.75 | 2.13 | 2.5 | 3 | 3.5 | 4 | 4.5 | 5 | 7.48 |
| 4.5 | 4.5 | 4.5 | 4.5 | 4.5 | 4.5 | 4.5 | 4.5 | 5 | 5.66 |
| 3 | 3 | 3 | 3 | 3 | 3.5 | 4 | 4.5 | 5 | 6.89 |
| 2 | 2 | 2 | 2.33 | 2.67 | 3 | 3 | 2.75 | 2.5 | 2.41 |

FIG. 10

INFUSION DEVICES AND RELATED METHODS AND SYSTEMS FOR REGULATING INSULIN ON BOARD

CROSS-REFERENCE TO RELATED APPLICATIONS

This application is a division of U.S. patent application Ser. No. 14/261,272, filed Apr. 24, 2014. The subject matter described herein is also related to the subject matter described in U.S. patent application Ser. No. 14/261,266, filed Apr. 24, 2014.

TECHNICAL FIELD

Embodiments of the subject matter described herein relate generally to medical devices, and more particularly, embodiments of the subject matter relate to controlling operations of a portable electronic device, such as a fluid infusion device.

BACKGROUND

Infusion pump devices and systems are relatively well known in the medical arts, for use in delivering or dispensing an agent, such as insulin or another prescribed medication, to a patient. A typical infusion pump includes a pump drive system which typically includes a small motor and drive train components that convert rotational motor motion to a translational displacement of a plunger (or stopper) in a reservoir that delivers medication from the reservoir to the body of a user via a fluid path created between the reservoir and the body of a user. Use of infusion pump therapy has been increasing, especially for delivering insulin for diabetics.

Continuous insulin infusion provides greater control of a diabetic's condition, and hence, control schemes are being developed that allow insulin infusion pumps to monitor and regulate a user's blood glucose level in a substantially continuous and autonomous manner, for example, overnight while the user is sleeping. Regulating blood glucose level is complicated by variations in the response time for the type of insulin being used along with each user's individual insulin response. Predictive algorithms may be utilized to provide estimations of the future blood glucose levels as an aid in regulating the blood glucose level. Rather than continuously sampling and monitoring a user's blood glucose level, which may compromise battery life, intermittently obtained blood glucose data samples may be utilized for determining estimations of future blood glucose levels.

Problems arise, however, when one or more blood glucose data samples intended for input to a predictive algorithm are corrupted, lost, or otherwise invalid, for example, due to noise, transmission errors, or the like. For example, in the case of recursive prediction algorithms, the prediction algorithm may be reset to eliminate the so-called "bad" data from undesirably influencing the device operation. Such an approach also incurs the lag time required for the prediction algorithm to achieve a desired level of reliability, and thus, would result in an inability to provide predictive control for periods of time.

BRIEF SUMMARY

An embodiment of a method of operating a device is provided. An exemplary method of operating an infusion device operable to deliver fluid influencing a physiological condition in the body of a user comprises determining a current amount of active fluid in the body of the user, determining a threshold amount of active fluid in the body of the user, and automatically altering operation of the infusion device to modify delivery of the fluid to the user based on a relationship between the current amount and the threshold amount.

In one embodiment, an infusion device is provided that comprises a motor operable to deliver fluid to a body of a user and a control module coupled to the motor to operate the motor to deliver the fluid based on a difference between a current measurement value for the physiological condition and a target value for the physiological condition when the current measurement value is greater than the target value. When the current measurement value is less than or equal to the target value and a current amount of active fluid in the body is less than a lower threshold amount, the control module operates the motor to deliver the fluid in a manner that regulates the current amount of the active fluid in the body of the user to the lower threshold amount. Conversely, when the current measurement value is less than or equal to the target value and the current amount of active fluid is greater than an upper threshold amount, the control module suspends operation of the motor.

In another embodiment, a method of operating an infusion device operable to deliver insulin to a body of a user is provided. The method involves identifying a minimum insulin on board for the user, identifying a current insulin on board for the user, generating a delivery command configured to regulate the current insulin on board to the minimum insulin on board, and operating the infusion device in accordance with the delivery command.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures, which may be illustrated for simplicity and clarity and are not necessarily drawn to scale.

FIG. 9 depicts a table of measurement sequences suitable for use with the control process of FIG. 8;

FIG. 10 depicts a table of the measurement sequences of FIG. 9 after modifying unusable measurement samples and determining a predicted measurement value in accordance with one or more exemplary embodiments of the control process of FIG. 8;

DETAILED DESCRIPTION

Figure 1:
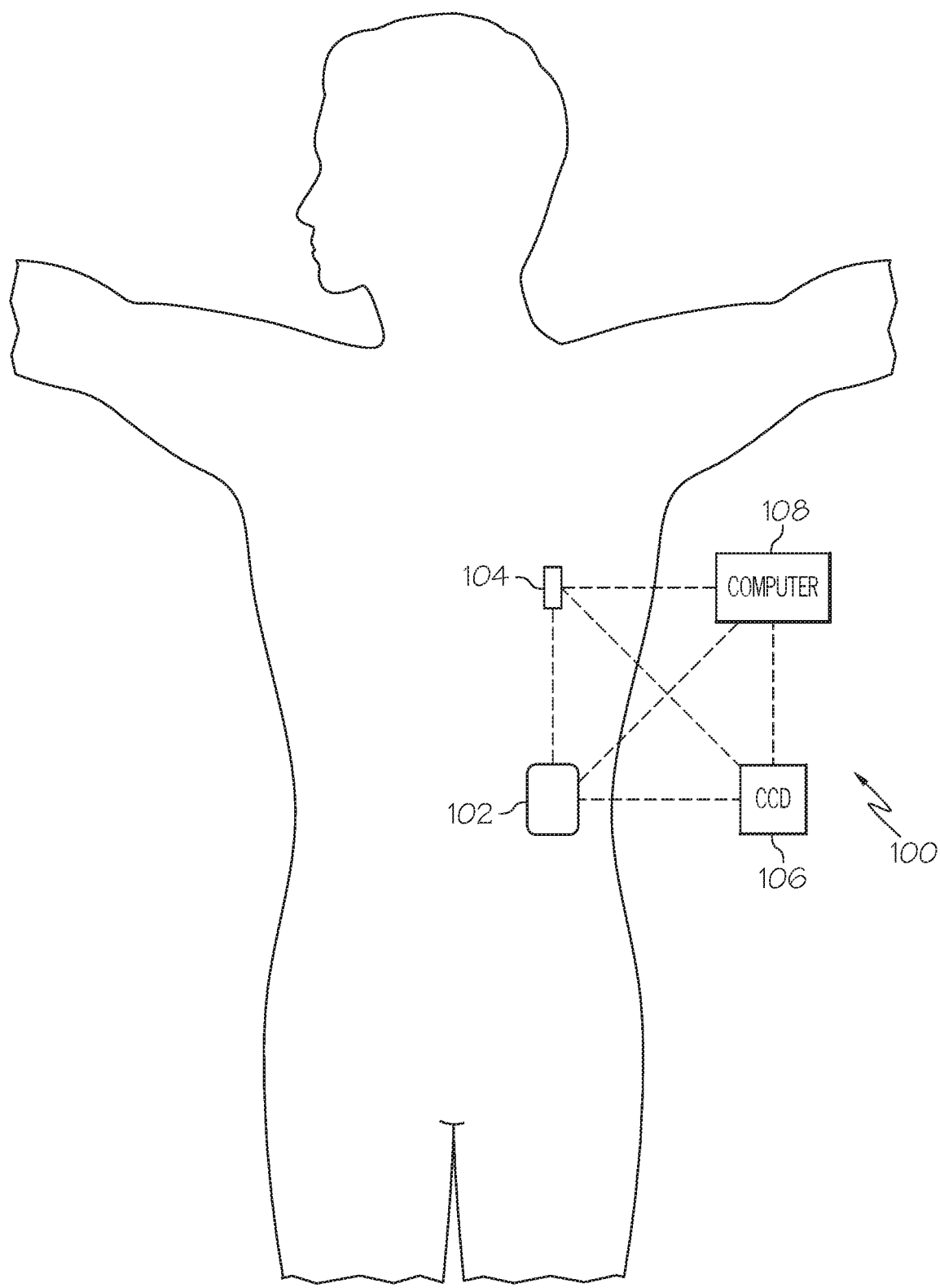
FIG. 1 depicts an exemplary embodiment of an infusion system.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

While the subject matter described herein can be implemented in any electronic device that includes a motor, exemplary embodiments described below are implemented in the form of medical devices, such as portable electronic medical devices. Although many different applications are possible, the following description focuses on a fluid infusion device (or infusion pump) as part of an infusion system deployment. For the sake of brevity, conventional techniques related to infusion system operation, insulin pump and/or infusion set operation, and other functional aspects of the systems (and the individual operating components of the systems) may not be described in detail here. Examples of infusion pumps may be of the type described in, but not limited to, U.S. Pat. Nos. 4,562,751; 4,685,903; 5,080,653; 5,505,709; 5,097,122; 6,485,465; 6,554,798; 6,558,320; 6,558,351; 6,641,533; 6,659,980; 6,752,787; 6,817,990; 6,932,584; and 7,621,893; each of which are herein incorporated by reference.

Embodiments of the subject matter described herein generally relate to fluid infusion devices including a motor that is operable to linearly displace a plunger (or stopper) of a reservoir provided within the fluid infusion device to deliver a dosage of fluid, such as insulin, to the body of a user. As described in greater detail below, in exemplary embodiments, the dosage commands that govern operation of the motor are influenced by not only a current (or most recent) measurement of a condition in the body of the user, but also a predicted value (or anticipated measurement) for that condition in the body of the user at some point in the future. For example, an insulin dosage command may be determined based on a current blood glucose measurement for the user in a manner that is influenced by a predicted (or anticipated) blood glucose level in the body of the user 30 minutes into the future. In this regard, the insulin dosage command determined based on the user's current blood glucose level may be adjusted, modified, enabled and/or disabled based on the predicted blood glucose level to increase the likelihood (if not ensure) that the user's blood glucose level is maintained within an acceptable range of values going forward. While the subject matter is described herein in the context of a fluid infusion device for purposes of explanation, the subject matter is not necessarily limited to such an implementation. For example, the predicted value may be determined and/or utilized by a monitoring device to determine when and/or how the monitoring device should be operated to alert or otherwise notify a user (or one or more other individuals) of a condition in the body of the user, an operational status of an infusion device or another medical device associated with the user, and/or the like.

As described in greater detail below in the context of FIGS. 5-10, in exemplary embodiments, a predicted blood glucose level is calculated or otherwise determined as a sum of the user's current blood glucose level and a weighted estimate of the trend in the user's blood glucose level that is determined based on previously obtained blood glucose levels for the user. In exemplary embodiments, the estimate of the trend is calculated as a weighted sum of the differences between consecutive measurements that precede the current measurement. Thus, previously obtained blood glucose measurements for the user are stored or otherwise maintained for use in calculating the estimate of the trend in a deterministic manner rather than a recursive manner. In exemplary embodiments described herein, when one or more of the previously obtained blood glucose measurements are unusable for determining the predicted value, one or more other blood glucose measurements are used to obtain a modified measurement value that is substituted or otherwise used in place of the unusable blood glucose measurement. In this manner, measurements that are deemed invalid, unacceptable, or otherwise unreliable are excluded from use in determining the predicted value. Rather than disabling or otherwise resetting the prediction and/or waiting until a full sequence of consecutive usable measurements is available, the modified measurement sequence is utilized to calculate the predicted value and continue operation of the device in a manner that is influenced by the predicted value.

As described in the context of FIGS. 11-19, in one or more embodiments, the operation of the infusion device is automatically altered or change to modify the delivery of fluid to the user when both the predicted value for a physiological condition of the user violates an applicable threshold value and the current value for the physiological condition also violates its corresponding applicable threshold value. In this regard, the operating mode for the infusion device is automatically adjusted or otherwise transitioned from an operating mode where delivery of the fluid is enabled (e.g., a delivery mode) to an alternative operating mode where delivery of the fluid is disabled or otherwise suspended (e.g., a suspend delivery mode), and vice versa. For example, the infusion device may automatically transition from a normal delivery mode used to regulate the blood glucose level of the user to an alternative operating mode where fluid delivery is suspended, disabled or otherwise altered in response to determining that the current glucose measurement value for the user is less than a first threshold value and the predicted glucose value for the user is less than a second threshold value.

In the suspend delivery mode, any delivery (or dosage) commands that may otherwise be determined using the normal delivery control scheme (e.g., open-loop delivery commands to provide a basal infusion rate, closed-loop delivery commands based on the user's current glucose measurement value, or the like) are disabled or otherwise deactivated to reduce the likelihood and/or mitigate the potential impact of the user's blood glucose level falling below a protection threshold value. Similarly, the infusion device may automatically transition from the suspend delivery mode to another operating mode resume delivery of fluid to the user when both the current and predicted glucose values exceed their respective delivery resumption thresholds. In this regard, any delivery (or dosage) commands determined in accordance with the normal delivery control scheme are re-enabled or otherwise reactivated to resume regulating the user's blood glucose. For purposes of explanation, the subject matter may be described herein in the context of the normal delivery control scheme (or delivery mode) that provides closed-loop control of a physiological condition of the user (e.g., the user's blood glucose) to regulate a current measurement value for the physiological condition of the user to a target value. That said, it will be appreciated that the subject matter described herein can be implemented in an equivalent manner in embodiments where the normal delivery mode control scheme provides open-loop control to maintain a basal infusion rate of fluid to the user. Accordingly, the subject matter described herein is not intended to any particular delivery mode or control scheme.

In an exemplary embodiment, the threshold values used to suspend or resume delivery are based on a user-configurable protection threshold value. For example, the user may input or otherwise provide a baseline blood glucose value below which the user would like to minimize his or her exposure to. For purposes of explanation, the input value from the user is alternatively referred to herein as the suspend protection threshold (SPT) value or variants thereof. Based on the suspend protection threshold value, a second threshold to be applied to the predicted glucose value, alternatively referred to herein as a predictive suspend threshold value, may be calculated or otherwise determined, for example, by adding/subtracting an offset to/from the suspend protection threshold value, multiplying the suspend protection threshold value by a conversion factor, or the like. In a similar manner, a suspend enable threshold value to be applied to the current glucose measurement value may also be calculated or determined based on the suspend protection threshold value. In exemplary embodiments, the infusion device is automatically transitioned to the suspend delivery mode when the predicted glucose value is less than or equal to the predictive suspend threshold value and the user's current glucose measurement value is less than or equal to the suspend enable threshold value, thereby reducing the likelihood of the user's current glucose measurement value reaching the suspend protection threshold value. Additionally, the infusion device may be automatically transitioned to the suspend delivery mode when the user's current glucose measurement value is less than both the suspend protection threshold value and the suspend enable threshold value. In this manner, suspension of delivery is ensured when the current glucose measurement value reaches the level for which the user has indicated he or she would like protection.

In a similar manner, a resume (or delivery) enable threshold value that is greater than or equal to the suspend protection threshold value may be calculated or otherwise determined based on the suspend protection threshold value (e.g., by adding an offset). Additionally, a predictive resume threshold value greater than the resume enable threshold value may be calculated or otherwise determined based on the suspend protection threshold value and/or the resume enable threshold value (e.g., by adding another offset). Thereafter, when the user's current glucose measurement value is greater than the resume enable threshold value and the predicted glucose value is greater than the predictive resume threshold value, the infusion device is automatically transitioned from the suspend delivery mode to an operating mode where delivery of fluid to the user is enabled. The resume delivery thresholds may be chosen relative to the suspend thresholds to provide a hysteretic effect. Additionally, in exemplary embodiments, a minimum suspension time period is imposed after transitioning to the suspend delivery mode to further ensure that the infusion device does not toggle between operating modes. In exemplary embodiments, a refractory period is also imposed when transitioning from the suspend delivery mode to a delivery mode ensure that the infusion device does not repeatedly operate in the suspend delivery mode without at least some recovery time period elapsing.

During prolonged periods of nondelivery, the amount of the fluid that remains active within the user's body (e.g., the fluid yet to be metabolized or in the process of being metabolized) may become depleted. Furthermore, when fluid delivery is resumed, there may be a delay between when the fluid is infused and when the fluid begins having a corresponding effect on the physiological condition of the user, which, in turn, may result in the physiological condition reaching undesirable levels. For example, infusion of insulin may be suspended when the user's current and/or predicted blood glucose levels fall below applicable threshold values, as described above. While insulin infusion is suspended, the amount of active insulin in the user's body (i.e., the insulin on board) decreases. Thereafter, as the user's blood glucose level rises, additional insulin may not be infused until the user's blood glucose levels exceed a target blood glucose level. However, the user's insulin response introduces a delay between the time when the insulin is infused and the time when the corresponding response occurs in the user's blood glucose, at which point, the user's blood glucose level may have risen to an undesirably high level.

As described in greater detail below in the context of FIGS. 20-21, in one or more embodiments, the infusion device may automatically transition from the suspend delivery mode to an alternative delivery mode that regulates an active amount of the fluid within the user's body, rather than maintaining a predetermined basal infusion rate or otherwise regulating the physiological condition of the user in accordance with the normal delivery mode. For example, the infusion device may automatically transition from the suspend delivery mode to an insulin on board (JOB) control mode that regulates the insulin infusion rate to maintain at least a threshold amount of insulin on board. In this regard, when the user's current glucose level is less than the desired target (or reference) glucose level, the insulin on board control mode may provide a minimum infusion rate that may be greater than the infusion rate that would otherwise be determined based on the normal closed-loop delivery mode based on the difference between the user's current glucose measurement value and the user's target (or reference) glucose value. For example, even though the user's current glucose measurement values and/or predicted glucose values may be rising, the normal closed-loop delivery mode may result in a delivery command of zero (or nondelivery) while the user's current glucose measurement value is less than the user's target glucose value. Thus, the IOB control mode may preemptively infuse insulin to maintain the insulin on board at a level that reduces the likelihood of a hyperglycemic rebound event in response to transitioning out of the suspend delivery mode or another prolonged period of nondelivery.

In one or more embodiments, the IOB control mode may be utilized in lieu of or in addition to the suspend delivery mode. For example, when the user's predicted blood glucose value and the user's current blood glucose measurement value are both less than their applicable threshold values for suspending delivery, the infusion device may automatically transition from a normal closed-loop delivery mode to the IOB control mode to maintain at least a threshold amount of insulin on board. The IOB control mode could be used in lieu of the suspend delivery mode. Thereafter, when the user's predicted blood glucose value and the user's current blood glucose measurement value are both greater than their applicable threshold values for enabling the normal closed-loop delivery mode, the infusion device may automatically transition from the IOB control mode back to the normal closed-loop delivery mode. Furthermore, in some embodiments, the infusion device may automatically transition from the IOB control mode to the suspend delivery mode after previously transitioning from normal closed-loop delivery mode to the IOB control mode, for example, when the user's current glucose measurement value is less than the absolute suspend protection threshold value set by the user. Thus, the IOB control mode may be used instead of predictively suspending infusion delivery based on the predicted blood glucose value, while the suspend delivery mode is still utilized to automatically suspend delivery when the current blood glucose measurement value is at or below a mandatory suspend threshold value. In such embodiments, the IOB control mode may function as a buffer or transitional delivery mode between the suspend delivery mode and the normal closed-loop or open-loop delivery mode.

Turning now to FIG. 1, one exemplary embodiment of an infusion system 100 includes, without limitation, a fluid infusion device (or infusion pump) 102, a sensing arrangement 104, a command control device (CCD) 106, and a computer 108. The components of an infusion system 100 may be realized using different platforms, designs, and configurations, and the embodiment shown in FIG. 1 is not exhaustive or limiting. In practice, the infusion device 102 and the sensing arrangement 104 are secured at desired locations on the body of a user (or patient), as illustrated in FIG. 1. In this regard, the locations at which the infusion device 102 and the sensing arrangement 104 are secured to the body of the user in FIG. 1 are provided only as a representative, non-limiting, example. The elements of the infusion system 100 may be similar to those described in U.S. patent application Ser. No. 13/049,803, the subject matter of which is hereby incorporated by reference in its entirety.

In the illustrated embodiment of FIG. 1, the infusion device 102 is designed as a portable medical device suitable for infusing a fluid, a liquid, a gel, or other agent into the body of a user. In exemplary embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. In some embodiments, the fluid may include a nutritional supplement, a dye, a tracing medium, a saline medium, a hydration medium, or the like.

The sensing arrangement 104 generally represents the components of the infusion system 100 configured to sense, detect, measure or otherwise quantify a condition of the user, and may include a sensor, a monitor, or the like, for providing data indicative of the condition that is sensed, detected, measured or otherwise monitored by the sensing arrangement. In this regard, the sensing arrangement 104 may include electronics and enzymes reactive to a biological condition, such as a blood glucose level, or the like, of the user, and provide data indicative of the blood glucose level to the infusion device 102, the CCD 106 and/or the computer 108. For example, the infusion device 102, the CCD 106 and/or the computer 108 may include a display for presenting information or data to the user based on the sensor data received from the sensing arrangement 104, such as, for example, a current glucose level of the user, a graph or chart of the user's glucose level versus time, device status indicators, alert messages, or the like. In other embodiments, the infusion device 102, the CCD 106 and/or the computer 108 may include electronics and software that are configured to analyze sensor data and operate the infusion device 102 to deliver fluid to the body of the user based on the sensor data and/or preprogrammed delivery routines. Thus, in exemplary embodiments, one or more of the infusion device 102, the sensing arrangement 104, the CCD 106, and/or the computer 108 includes a transmitter, a receiver, and/or other transceiver electronics that allow for communication with other components of the infusion system 100, so that the sensing arrangement 104 may transmit sensor data or monitor data to one or more of the infusion device 102, the CCD 106 and/or the computer 108.

Still referring to FIG. 1, in various embodiments, the sensing arrangement 104 may be secured to the body of the user or embedded in the body of the user at a location that is remote from the location at which the infusion device 102 is secured to the body of the user. In various other embodiments, the sensing arrangement 104 may be incorporated within the infusion device 102. In other embodiments, the sensing arrangement 104 may be separate and apart from the infusion device 102, and may be, for example, part of the CCD 106. In such embodiments, the sensing arrangement 104 may be configured to receive a biological sample, analyte, or the like, to measure a condition of the user.

As described above, in some embodiments, the CCD 106 and/or the computer 108 may include electronics and other components configured to perform processing, delivery routine storage, and to control the infusion device 102 in a manner that is influenced by sensor data measured by and/or received from the sensing arrangement 104. By including control functions in the CCD 106 and/or the computer 108, the infusion device 102 may be made with more simplified electronics. However, in other embodiments, the infusion device 102 may include all control functions, and may operate without the CCD 106 and/or the computer 108. In various embodiments, the CCD 106 may be a portable electronic device. In addition, in various embodiments, the infusion device 102 and/or the sensing arrangement 104 may be configured to transmit data to the CCD 106 and/or the computer 108 for display or processing of the data by the CCD 106 and/or the computer 108.

In some embodiments, the CCD 106 and/or the computer 108 may provide information to the user that facilitates the user's subsequent use of the infusion device 102. For example, the CCD 106 may provide information to the user to allow the user to determine the rate or dose of medication to be administered into the user's body. In other embodiments, the CCD 106 may provide information to the infusion device 102 to autonomously control the rate or dose of medication administered into the body of the user. In some embodiments, the sensing arrangement 104 may be integrated into the CCD 106. Such embodiments may allow the user to monitor a condition by providing, for example, a sample of his or her blood to the sensing arrangement 104 to assess his or her condition. In some embodiments, the sensing arrangement 104 and the CCD 106 may be used for determining glucose levels in the blood and/or body fluids of the user without the use of, or necessity of, a wire or cable connection between the infusion device 102 and the sensing arrangement 104 and/or the CCD 106.

In some embodiments, the sensing arrangement 104 and/or the infusion device 102 are cooperatively configured to utilize a closed-loop system for delivering fluid to the user. Examples of sensing devices and/or infusion pumps utilizing closed-loop systems may be found at, but are not limited to, the following U.S. Pat. Nos. 6,088,608, 6,119,028, 6,589,229, 6,740,072, 6,827,702, 7,323,142, and 7,402, 153, all of which are incorporated herein by reference in their entirety. In such embodiments, the sensing arrangement 104 is configured to sense or measure a condition of the user, such as, blood glucose level or the like. The infusion device 102 is configured to deliver fluid in response to the condition sensed by the sensing arrangement 104. In turn, the sensing arrangement 104 continues to sense or otherwise quantify a current condition of the user, thereby allowing the infusion device 102 to deliver fluid continuously in response to the condition currently (or most recently) sensed by the sensing arrangement 104 indefinitely. In some embodiments, the sensing arrangement 104 and/or the infusion device 102 may be configured to utilize the closed-loop system only for a portion of the day, for example only when the user is asleep or awake.

As described in greater detail below in the context of FIGS. 5-10, in exemplary embodiments, the sensing arrangement 104 and/or the infusion device 102 are cooperatively configured to determine one or more predicted values for the condition in the body of the user at one or more times in the future. Thereafter, the delivery of the fluid may be influenced by the one or more predicted values indicative of the anticipated future condition of the user in addition to a recently obtained value indicative of the current condition of the user. For example, commands for operating the infusion device to deliver insulin may be determined as a function of a currently sensed blood glucose value and one or more predicted blood glucose values in a manner that accounts for the anticipated response time for the insulin and/or the user using the preceding blood glucose measurement values and/or the preceding dosage commands. To put it another way, the control of a user's blood glucose level to regulate the user's blood glucose level using the user's current blood glucose level may be influenced by one or more predicted blood glucose levels for the user in the future. As described in the context of FIGS. 11-19, in one or more exemplary embodiments, the operating mode for the infusion device 102 is automatically adjusted or altered based on the predicted blood glucose value and/or the current blood glucose measurement value violating applicable threshold values.

Figure 2:
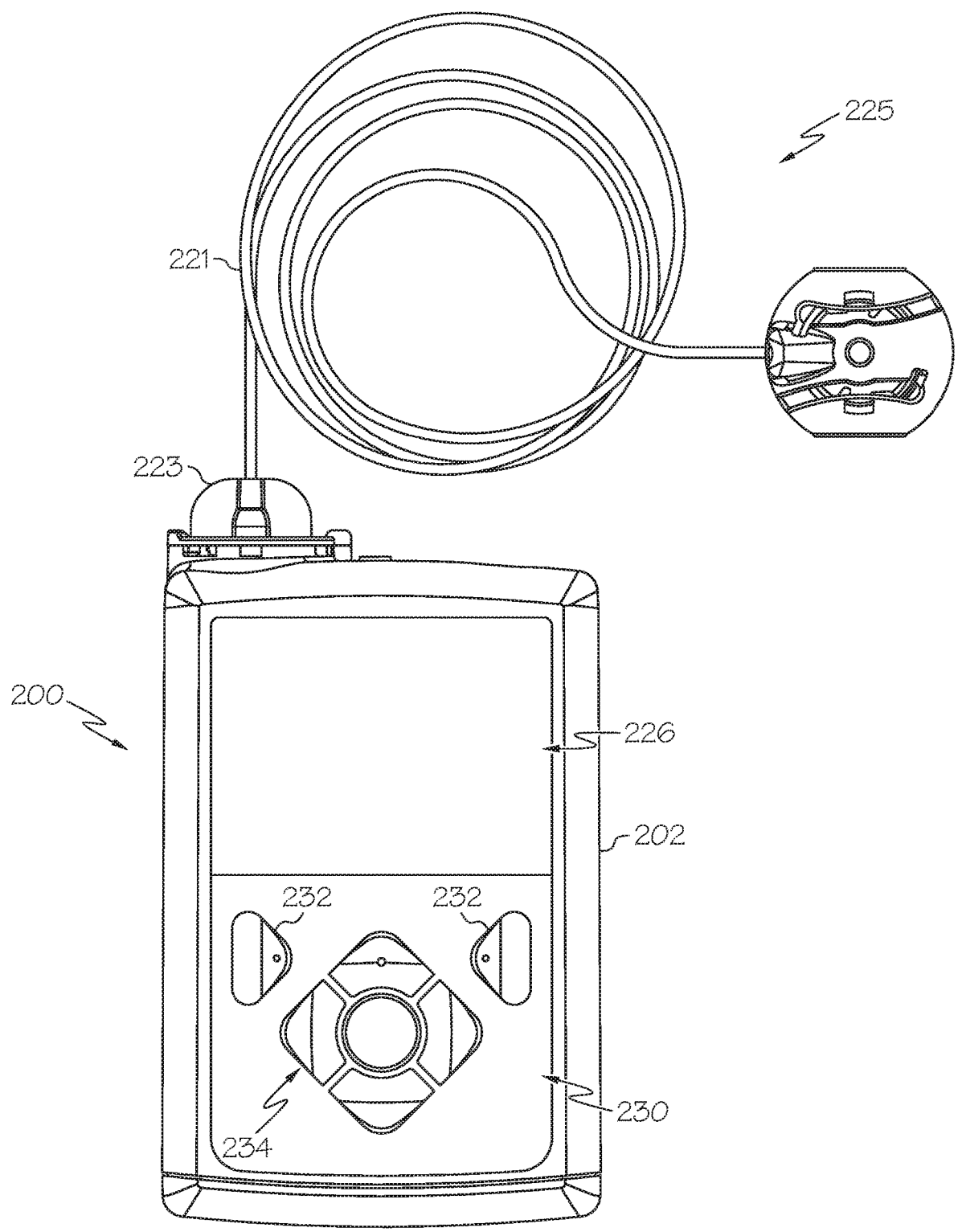
FIG. 2 depicts a plan view of an exemplary embodiment of a fluid infusion device suitable for use in the infusion system of FIG. 1.
Figure 3:
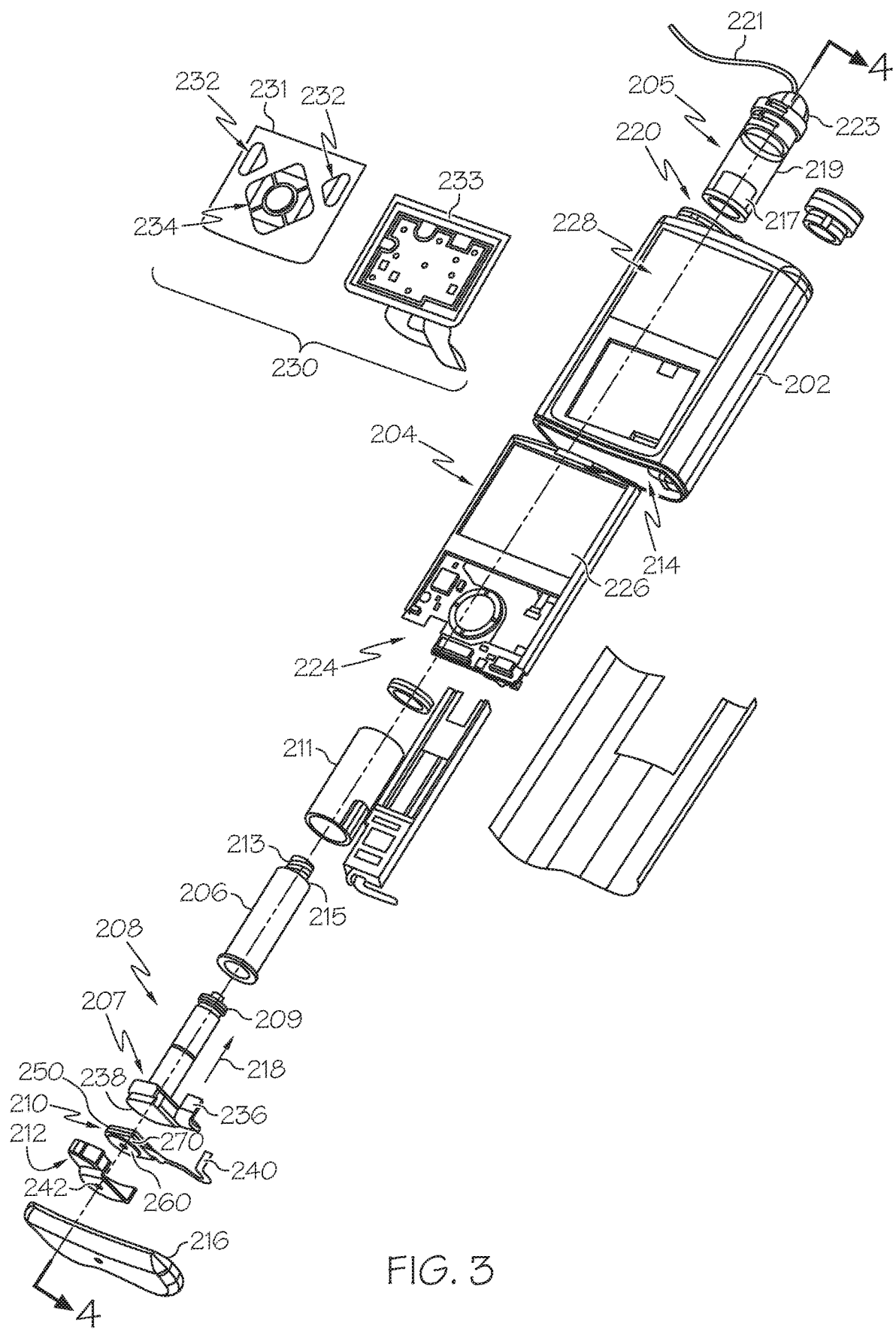
FIG. 3 is an exploded perspective view of the fluid infusion device of FIG. 2.
Figure 4:
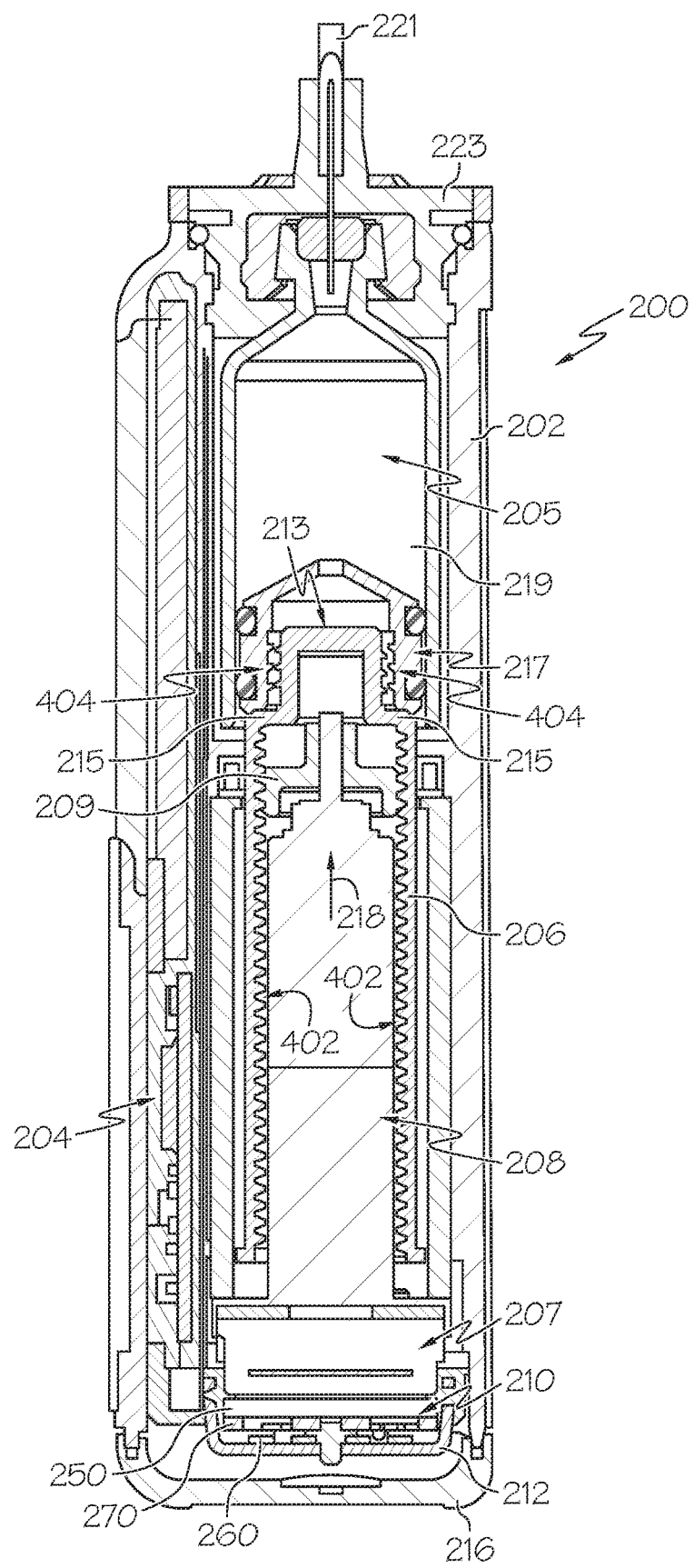
FIG. 4 is a cross-sectional view of the fluid infusion device of FIGS. 2-3 as viewed along line 4-4 in FIG. 3 when assembled with a reservoir inserted in the infusion device.

FIGS. 2-4 depict one exemplary embodiment of a fluid infusion device 200 (or alternatively, infusion pump) suitable for use in an infusion system, such as, for example, as infusion device 102 in the infusion system 100 of FIG. 1. The fluid infusion device 200 is a portable medical device designed to be carried or worn by a patient (or user), and the fluid infusion device 200 may leverage any number of conventional features, components, elements, and characteristics of existing fluid infusion devices, such as, for example, some of the features, components, elements, and/or characteristics described in U.S. Pat. Nos. 6,485,465 and 7,621,893. It should be appreciated that FIGS. 2-4 depict some aspects of the infusion device 200 in a simplified manner; in practice, the infusion device 200 could include additional elements, features, or components that are not shown or described in detail herein.

As best illustrated in FIGS. 2-3, the illustrated embodiment of the fluid infusion device 200 includes a housing 202 adapted to receive a fluid-containing reservoir 205. An opening 220 in the housing 202 accommodates a fitting 223 (or cap) for the reservoir 205, with the fitting 223 being configured to mate or otherwise interface with tubing 221 of an infusion set 225 that provides a fluid path to/from the body of the user. In this manner, fluid communication from the interior of the reservoir 205 to the user is established via the tubing 221. The illustrated fluid infusion device 200 includes a human-machine interface (HMI) 230 (or user interface) that includes elements 232, 234 that can be manipulated by the user to administer a bolus of fluid (e.g., insulin), to change therapy settings, to change user preferences, to select display features, and the like. The infusion device also includes a display element 226, such as a liquid crystal display (LCD) or another suitable display element, that can be used to present various types of information or data to the user, such as, without limitation: the current glucose level of the patient; the time; a graph or chart of the patient's glucose level versus time; device status indicators; etc.

The housing 202 is formed from a substantially rigid material having a hollow interior 214 adapted to allow an electronics assembly 204, a sliding member (or slide) 206, a drive system 208, a sensor assembly 210, and a drive system capping member 212 to be disposed therein in addition to the reservoir 205, with the contents of the housing 202 being enclosed by a housing capping member 216. The opening 220, the slide 206, and the drive system 208 are coaxially aligned in an axial direction (indicated by arrow 218), whereby the drive system 208 facilitates linear displacement of the slide 206 in the axial direction 218 to dispense fluid from the reservoir 205 (after the reservoir 205 has been inserted into opening 220), with the sensor assembly 210 being configured to measure axial forces (e.g., forces aligned with the axial direction 218) exerted on the sensor assembly 210 responsive to operating the drive system 208 to displace the slide 206. In various embodiments, the sensor assembly 210 may be utilized to detect one or more of the following: an occlusion in a fluid path that slows, prevents, or otherwise degrades fluid delivery from the reservoir 205 to a user's body; when the reservoir 205 is empty; when the slide 206 is properly seated with the reservoir 205; when a fluid dose has been delivered; when the infusion pump 200 is subjected to shock or vibration; when the infusion pump 200 requires maintenance.

Depending on the embodiment, the fluid-containing reservoir 205 may be realized as a syringe, a vial, a cartridge, a bag, or the like. In certain embodiments, the infused fluid is insulin, although many other fluids may be administered through infusion such as, but not limited to, HIV drugs, drugs to treat pulmonary hypertension, iron chelation drugs, pain medications, anti-cancer treatments, medications, vitamins, hormones, or the like. As best illustrated in FIGS. 3-4, the reservoir 205 typically includes a reservoir barrel 219 that contains the fluid and is concentrically and/or coaxially aligned with the slide 206 (e.g., in the axial direction 218) when the reservoir 205 is inserted into the infusion pump 200. The end of the reservoir 205 proximate the opening 220 may include or otherwise mate with the fitting 223, which secures the reservoir 205 in the housing 202 and prevents displacement of the reservoir 205 in the axial direction 218 with respect to the housing 202 after the reservoir 205 is inserted into the housing 202. As described above, the fitting 223 extends from (or through) the opening 220 of the housing 202 and mates with tubing 221 to establish fluid communication from the interior of the reservoir 205 (e.g., reservoir barrel 219) to the user via the tubing 221 and infusion set 225. The opposing end of the reservoir 205 proximate the slide 206 includes a plunger 217 (or stopper) positioned to push fluid from inside the barrel 219 of the reservoir 205 along a fluid path through tubing 221 to a user. The slide 206 is configured to mechanically couple or otherwise engage with the plunger 217, thereby becoming seated with the plunger 217 and/or reservoir 205. Fluid is forced from the reservoir 205 via tubing 221 as the drive system 208 is operated to displace the slide 206 in the axial direction 218 toward the opening 220 in the housing 202.

In the illustrated embodiment of FIGS. 3-4, the drive system 208 includes a motor assembly 207 and a drive screw 209. The motor assembly 207 includes a motor that is coupled to drive train components of the drive system 208 that are configured to convert rotational motor motion to a translational displacement of the slide 206 in the axial direction 218, and thereby engaging and displacing the plunger 217 of the reservoir 205 in the axial direction 218. In some embodiments, the motor assembly 207 may also be powered to translate the slide 206 in the opposing direction (e.g., the direction opposite direction 218) to retract and/or detach from the reservoir 205 to allow the reservoir 205 to be replaced. In exemplary embodiments, the motor assembly 207 includes a brushless DC (BLDC) motor having one or more permanent magnets mounted, affixed, or otherwise disposed on its rotor. However, the subject matter described herein is not necessarily limited to use with BLDC motors, and in alternative embodiments, the motor may be realized as a solenoid motor, an AC motor, a stepper motor, a piezoelectric caterpillar drive, a shape memory actuator drive, an electrochemical gas cell, a thermally driven gas cell, a bimetallic actuator, or the like. The drive train components may comprise one or more lead screws, cams, ratchets, jacks, pulleys, pawls, clamps, gears, nuts, slides, bearings, levers, beams, stoppers, plungers, sliders, brackets, guides, bearings, supports, bellows, caps, diaphragms, bags, heaters, or the like. In this regard, although the illustrated embodiment of the infusion pump utilizes a coaxially aligned drive train, the motor could be arranged in an offset or otherwise non-coaxial manner, relative to the longitudinal axis of the reservoir 205.

As best shown in FIG. 4, the drive screw 209 mates with threads 402 internal to the slide 206. When the motor assembly 207 is powered and operated, the drive screw 209 rotates, and the slide 206 is forced to translate in the axial direction 218. In an exemplary embodiment, the infusion pump 200 includes a sleeve 211 to prevent the slide 206 from rotating when the drive screw 209 of the drive system 208 rotates. Thus, rotation of the drive screw 209 causes the slide 206 to extend or retract relative to the drive motor assembly 207. When the fluid infusion device is assembled and operational, the slide 206 contacts the plunger 217 to engage the reservoir 205 and control delivery of fluid from the infusion pump 200. In an exemplary embodiment, the shoulder portion 215 of the slide 206 contacts or otherwise engages the plunger 217 to displace the plunger 217 in the axial direction 218. In alternative embodiments, the slide 206 may include a threaded tip 213 capable of being detachably engaged with internal threads 404 on the plunger 217 of the reservoir 205, as described in detail in U.S. Pat. Nos. 6,248,093 and 6,485,465, which are incorporated by reference herein.

As illustrated in FIG. 3, the electronics assembly 204 includes control electronics 224 coupled to the display element 226, with the housing 202 including a transparent window portion 228 that is aligned with the display element 226 to allow the display 226 to be viewed by the user when the electronics assembly 204 is disposed within the interior 214 of the housing 202. The control electronics 224 generally represent the hardware, firmware, processing logic and/or software (or combinations thereof) configured to control operation of the motor assembly 207 and/or drive system 208, as described in greater detail below in the context of FIG. 5. Whether such functionality is implemented as hardware, firmware, a state machine, or software depends upon the particular application and design constraints imposed on the embodiment. Those familiar with the concepts described here may implement such functionality in a suitable manner for each particular application, but such implementation decisions should not be interpreted as being restrictive or limiting. In an exemplary embodiment, the control electronics 224 includes one or more programmable controllers that may be programmed to control operation of the infusion pump 200.

The motor assembly 207 includes one or more electrical leads 236 adapted to be electrically coupled to the electronics assembly 204 to establish communication between the control electronics 224 and the motor assembly 207. In response to command signals from the control electronics 224 that operate a motor driver (e.g., a power converter) to regulate the amount of power supplied to the motor from a power supply, the motor actuates the drive train components of the drive system 208 to displace the slide 206 in the axial direction 218 to force fluid from the reservoir 205 along a fluid path (including tubing 221 and an infusion set), thereby administering doses of the fluid contained in the reservoir 205 into the user's body. Preferably, the power supply is realized one or more batteries contained within the housing 202. Alternatively, the power supply may be a solar panel, capacitor, AC or DC power supplied through a power cord, or the like. In some embodiments, the control electronics 224 may operate the motor of the motor assembly 207 and/or drive system 208 in a stepwise manner, typically on an intermittent basis; to administer discrete precise doses of the fluid to the user according to programmed delivery profiles.

Referring to FIGS. 2-4, as described above, the user interface 230 includes HMI elements, such as buttons 232 and a directional pad 234, that are formed on a graphic keypad overlay 231 that overlies a keypad assembly 233, which includes features corresponding to the buttons 232, directional pad 234 or other user interface items indicated by the graphic keypad overlay 231. When assembled, the keypad assembly 233 is coupled to the control electronics 224, thereby allowing the HMI elements 232, 234 to be manipulated by the user to interact with the control electronics 224 and control operation of the infusion pump 200, for example, to administer a bolus of insulin, to change therapy settings, to change user preferences, to select display features, to set or disable alarms and reminders, and the like. In this regard, the control electronics 224 maintains and/or provides information to the display 226 regarding program parameters, delivery profiles, pump operation, alarms, warnings, statuses, or the like, which may be adjusted using the HMI elements 232, 234. In various embodiments, the HMI elements 232, 234 may be realized as physical objects (e.g., buttons, knobs, joysticks, and the like) or virtual objects (e.g., using touch-sensing and/or proximity-sensing technologies). For example, in some embodiments, the display 226 may be realized as a touch screen or touch-sensitive display, and in such embodiments, the features and/or functionality of the HMI elements 232, 234 may be integrated into the display 226 and the HMI 230 may not be present. In some embodiments, the electronics assembly 204 may also include alert generating elements coupled to the control electronics 224 and suitably configured to generate one or more types of feedback, such as, without limitation: audible feedback; visual feedback; haptic (physical) feedback; or the like.

Referring to FIGS. 3-4, in accordance with one or more embodiments, the sensor assembly 210 includes a back plate structure 250 and a loading element 260. The loading element 260 is disposed between the capping member 212 and a beam structure 270 that includes one or more beams having sensing elements disposed thereon that are influenced by compressive force applied to the sensor assembly 210 that deflects the one or more beams, as described in greater detail in U.S. patent application Ser. No. 12/908,807, which is incorporated by reference herein. In exemplary embodiments, the back plate structure 250 is affixed, adhered, mounted, or otherwise mechanically coupled to the bottom surface 238 of the drive system 208 such that the back plate structure 250 resides between the bottom surface 238 of the drive system 208 and the housing cap 216. The drive system capping member 212 is contoured to accommodate and conform to the bottom of the sensor assembly 210 and the drive system 208. The drive system capping member 212 may be affixed to the interior of the housing 202 to prevent displacement of the sensor assembly 210 in the direction opposite the direction of force provided by the drive system 208 (e.g., the direction opposite direction 218). Thus, the sensor assembly 210 is positioned between the motor assembly 207 and secured by the capping member 212, which prevents displacement of the sensor assembly 210 in a downward direction opposite the direction of arrow 218, such that the sensor assembly 210 is subjected to a reactionary compressive force when the drive system 208 and/or motor assembly 207 is operated to displace the slide 206 in the axial direction 218 in opposition to the fluid pressure in the reservoir 205. Under normal operating conditions, the compressive force applied to the sensor assembly 210 is correlated with the fluid pressure in the reservoir 205. As shown, electrical leads 240 are adapted to electrically couple the sensing elements of the sensor assembly 210 to the electronics assembly 204 to establish communication to the control electronics 224, wherein the control electronics 224 are configured to measure, receive, or otherwise obtain electrical signals from the sensing elements of the sensor assembly 210 that are indicative of the force applied by the drive system 208 in the axial direction 218.

Figure 5:
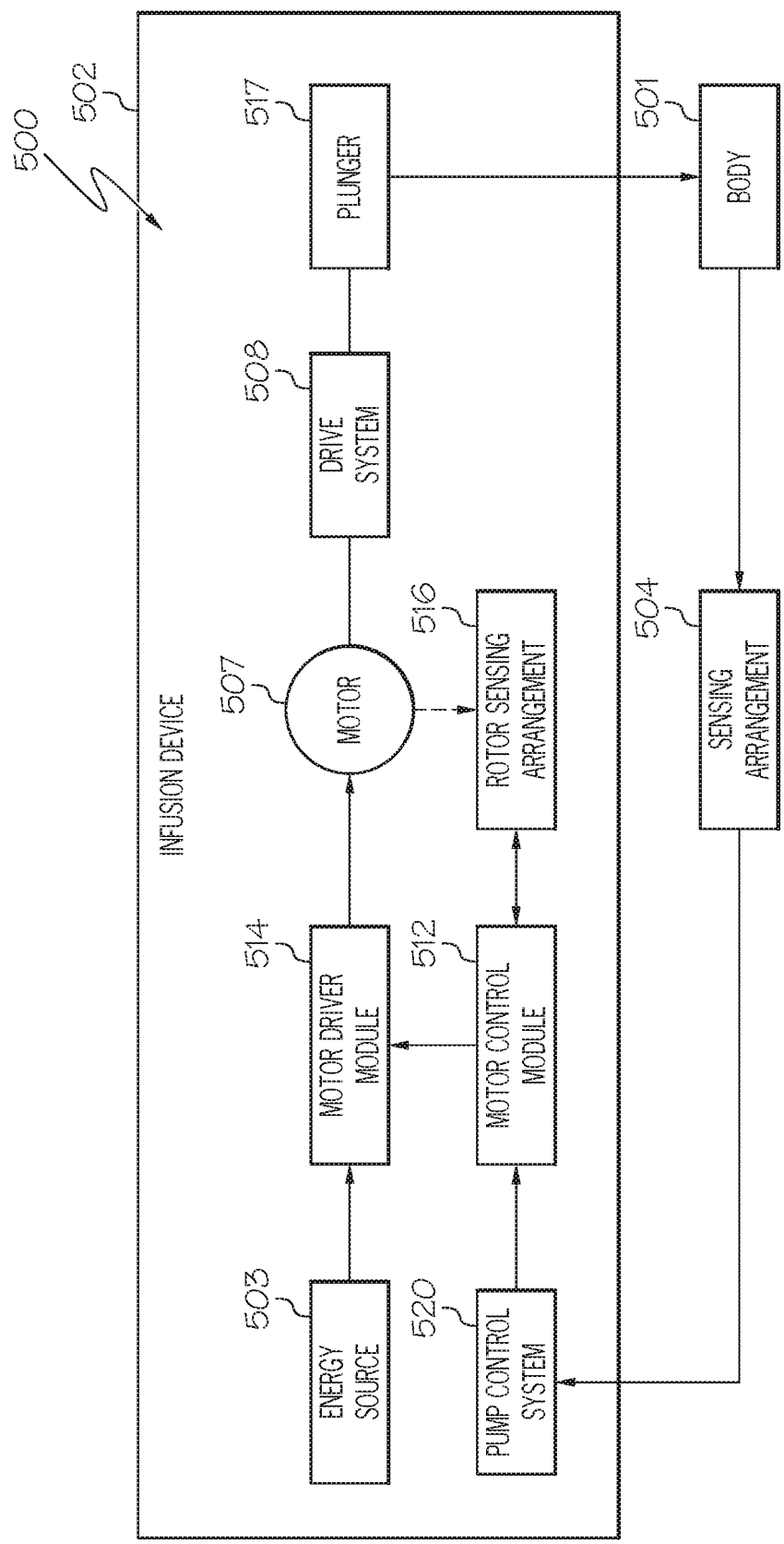
FIG. 5 is a block diagram of an exemplary control system suitable for use in a fluid infusion device, such as the fluid infusion device of FIG. 1.

FIG. 5 depicts an exemplary embodiment of a control system 500 suitable for use with an infusion device 502, such as the infusion device 102 in FIG. 1 or the infusion device 200 of FIG. 2. The control system 500 is configured to control or otherwise regulate a condition in the body 501 of a user to a desired (or target) value or otherwise maintain the condition within a range of acceptable values. In one or more exemplary embodiments, the condition being regulated is sensed, detected, measured or otherwise quantified by a sensing arrangement 504 (e.g., sensing arrangement 104) communicatively coupled to the infusion device 502. However, it should be noted that in alternative embodiments, the condition being regulated by the control system 500 may be correlative to the measured values obtained by the sensing arrangement 504. For example, the condition being regulated could be a blood glucose level or another condition that is influenced by physical activity of the user, and the sensing arrangement 504 may be realized as a heart rate monitor, a gyroscope, an accelerometer, or another suitable physiological sensor that provides measured values indicative of the level of physical activity being exhibited by the user.

It should be appreciated that FIG. 5 is a simplified representation of the infusion device 502 for purposes of explanation and is not intended to limit the subject matter described herein in any way. In this regard, more complex control schemes may be implemented by the control system 500 with multiple sensing arrangements 504 being utilized in conjunction with one another. For example, a blood glucose sensing device may be used with a heart rate monitor to implement a control scheme that regulates a user's blood glucose level based on the measured blood glucose level in a manner that accounts for the user's level of physical activity. That said, for clarity and ease of explanation, the subject matter may be described herein in the context of the control system 500 having an individual sensing arrangement 504 that senses, detects, measures or otherwise quantifies the condition being regulated.

In the illustrated embodiment, the infusion device 502 includes a motor control module 512 coupled to a motor 507 (e.g., motor assembly 207) that is operable to displace a plunger 517 (e.g., plunger 217) in a reservoir (e.g., reservoir 205) and provide a desired amount of fluid to the body 501 of a user. In this regard, displacement of the plunger 517 results in the delivery of a fluid that is capable of influencing the condition in the body 501 of the user to the body 501 of the user via a fluid delivery path (e.g., via tubing 221 of an infusion set 225). A motor driver module 514 is coupled between an energy source 503 and the motor 507. The motor control module 512 is coupled to the motor driver module 514, and the motor control module 512 generates or otherwise provides command signals that operate the motor driver module 514 to provide current (or power) from the energy source 503 to the motor 507 to displace the plunger 517 in response to receiving, from a pump control system 520, a dosage command indicative of the desired amount of fluid to be delivered. In this regard, the pump control system 520 generally represents the electronics and other components that control operation of the fluid infusion device 502 according to a desired infusion delivery program in a manner that is influenced by sensor data pertaining to a condition of a user (e.g., the user's current glucose level) received from the sensing arrangement 504 and/or in a manner that is dictated by the user. To support closed-loop control, the pump control system 520 receives or otherwise obtains a desired value (e.g., a target or command blood glucose value) for the condition in the body 501 of the user. For example, the infusion device 502 may store or otherwise maintain the target value in a data storage element accessible to the pump control system 520. Alternatively, the target value may be received from an external component (e.g., CCD 106 and/or computer 108).

In exemplary embodiments, the energy source 503 is realized as a battery housed within the infusion device 502 (e.g., within housing 202) that provides direct current (DC) power. In this regard, the motor driver module 514 generally represents the combination of circuitry, hardware and/or other electrical components configured to convert or otherwise transfer DC power provided by the energy source 503 into alternating electrical signals applied to respective phases of the stator windings of the motor 507 that result in current flowing through the stator windings that generates a stator magnetic field and causes the rotor of the motor 507 to rotate. The motor control module 512 is configured to receive or otherwise obtain a commanded dosage from the pump control system 520, convert the commanded dosage to a commanded translational displacement of the plunger 517, and command, signal, or otherwise operate the motor driver module 514 to cause the rotor of the motor 507 to rotate by an amount that produces the commanded translational displacement of the plunger 517. For example, the motor control module 512 may determine an amount of rotation of the rotor required to produce translational displacement of the plunger 517 that achieves the commanded dosage received from the pump control system 520. Based on the current rotational position (or orientation) of the rotor with respect to the stator that is indicated by the output of the rotor sensing arrangement 516, the motor control module 512 determines the appropriate sequence of alternating electrical signals to be applied to the respective phases of the stator windings that should rotate the rotor by the determined amount of rotation from its current position (or orientation). In embodiments where the motor 507 is realized as a BLDC motor, the alternating electrical signals commutate the respective phases of the stator windings at the appropriate orientation of the rotor magnetic poles with respect to the stator and in the appropriate order to provide a rotating stator magnetic field that rotates the rotor in the desired direction. Thereafter, the motor control module 512 operates the motor driver module 514 to apply the determined alternating electrical signals (e.g., the command signals) to the stator windings of the motor 507 to achieve the desired delivery of fluid to the user.

When the motor control module 512 is operating the motor driver module 514, current flows from the energy source 503 through the stator windings of the motor 507 to produce a stator magnetic field that interacts with the rotor magnetic field. In some embodiments, after the motor control module 512 operates the motor driver module 514 and/or motor 507 to achieve the commanded dosage, the motor control module 512 ceases operating the motor driver module 514 and/or motor 507 until a subsequent dosage command is received. In this regard, the motor driver module 514 and the motor 507 enter an idle state during which the motor driver module 514 effectively disconnects or isolates the stator windings of the motor 507 from the energy source 503. In other words, current does not flow from the energy source 503 through the stator windings of the motor 507 when the motor 507 is idle, and thus, the motor 507 does not consume power from the energy source 503 in the idle state, thereby improving efficiency.

Depending on the embodiment, the motor control module 512 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. Furthermore, the steps of a method or algorithm described in connection with the embodiments disclosed herein may be embodied directly in hardware, in firmware, in a software module executed by the motor control module 512, or in any practical combination thereof. In exemplary embodiments, the motor control module 512 includes or otherwise accesses a data storage element or memory, including any sort of random access memory (RAM), read only memory (ROM), flash memory, registers, hard disks, removable disks, magnetic or optical mass storage, or any other short or long term storage media or other non-transitory computer-readable medium, which is capable of storing programming instructions for execution by the motor control module 512. The computer-executable programming instructions, when read and executed by the motor control module 512, cause the motor control module 512 to perform the tasks, operations, functions, and processes described herein.

As described in greater detail below in the context of FIGS. 6-10, in one or more embodiments, the pump control system 520 generates or otherwise determines the dosage commands for operating the motor 507 to displace the plunger 517 based at least in part on a measurement value indicative of the current condition in the body 501 of the user in a manner that is influenced by a predicted value for the condition. In this regard, the predicted value is calculated based at least in part on the most recent (or current) measurement value and represents an estimate of the anticipated condition in the body 501 of the user at a particular point of time in the future. In exemplary embodiments, the pump control system 520 may adjust or override the dosage command for regulating the condition of the user based on the predicted value. For example, the pump control system 520 may suspend fluid delivery (e.g., by disabling the dosage command or setting the dosage command to zero) when the predicted value falls below a suspend delivery threshold value and resume fluid delivery (e.g., by enabling the dosage command or determining a nonzero dosage command using the current measurement value) when the predicted value exceeds a resume delivery threshold value. In exemplary embodiments, the resume delivery threshold value is different from the suspend delivery threshold value. For example, the resume delivery threshold value may be equal to the suspend delivery value plus some offset value (which may be a percentage of the suspend delivery value). In other embodiments, the resume delivery threshold value may be equal to the suspend delivery threshold value.

In accordance with one or more embodiments, based on the predicted value, the pump control system 520 may adjust the dosage command for regulating the condition of the user based on the observed condition of the user and the trends in the user's condition. For example, if a predicted blood glucose level indicates that the user's blood glucose level is expected to fall below a lower threshold value, the pump control system 520 may reduce the dosage command (e.g., to zero or some other relatively smaller amount) to ensure the blood glucose level is maintained above the lower threshold value, even though the current blood glucose measurement value indicates the blood glucose level is sufficiently above the lower threshold value. Conversely, if the predicted blood glucose level indicates that the user's blood glucose level is expected to exceed an upper threshold value, the pump control system 520 may increase the dosage command to ensure the blood glucose level is maintained below the upper threshold value, even though the current blood glucose measurement value indicates the blood glucose level is sufficiently below the upper threshold value. For example, if a target blood glucose level is between a resume delivery threshold value and a suspend delivery threshold value, the pump control system 520 may decrease and/or increase the dosage command to attempt to maintain the blood glucose level between the resume delivery threshold value and the suspend delivery threshold value, and thereby improve the likelihood of the blood glucose level being maintained at or near the target value.

In some embodiments, the pump control system 520 may generate or otherwise provide an alert based on the predicted value. For example, the pump control system 520 may generate or otherwise provide an auditory and/or visual notification to the user associated with the infusion device 502 that fluid delivery can or should be suspended when the predicted value falls below a threshold value and/or that fluid delivery can or should be resumed.

In exemplary embodiments, the predicted value is calculated by adding the current measurement value to a weighted sum determined using the preceding measurement values. In this regard, a sequence of the most recently obtained measurement values for the condition in the body 501 of the user is stored or otherwise maintained. For example, in one embodiment, the predicted value is calculated using a truncated Taylor series expansion or a recursive prediction algorithm, such as a Holt-Winters exponential smoothing function. In some embodiments, the sensing arrangement 504 includes a data storage element (or memory) for storing the sensor data sequence comprised of the current measurement value and a number of preceding measurement values, as described in greater detail below in the context of FIG. 6. Additionally, in such embodiments, the sensing arrangement 504 may calculate or otherwise determine the predicted value for the condition in the body 501 of the user based on the stored sensor measurement data sequence and transmit or otherwise provide the predicted value to the pump control system 520 along with the current measurement value. Alternatively, the sensing arrangement 504 may transmit or otherwise provide the sensor measurement data sequence to the pump control system 520, which, in turn, calculates the predicted value using the sensor data sequence received from the sensing arrangement 504. In yet other embodiments, the pump control system 520 may maintain a sensor measurement data sequence comprised of the current measurement value and a number of preceding measurement values received from the sensing arrangement 504 (e.g., by queuing or buffering the most recently received current measurement values), and based on the stored sensor measurement data sequence and the current measurement value received from the sensing arrangement 504, the pump control system 520 determines the predicted value for the condition in the body 501 of the user, as described in the context of FIG. 7.

Figure 8:
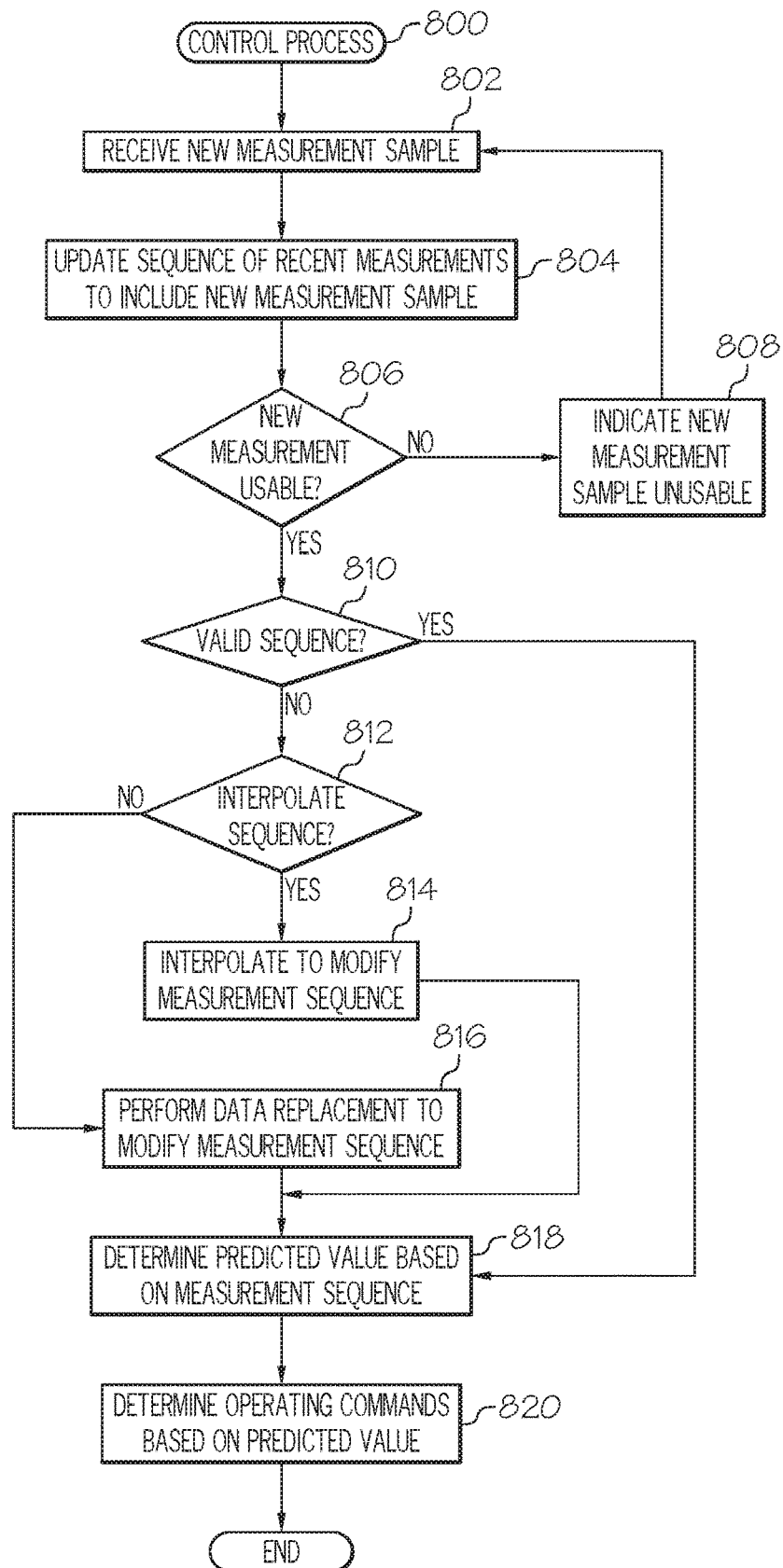
FIG. 8 is a flow diagram of an exemplary control process suitable for use with the control system of FIG. 5.

As described in the context of FIGS. 8-10, in exemplary embodiments, either the sensing arrangement 504 or the pump control system 520 analyzes or otherwise monitors the sensor measurement data sequence and/or the current measurement value to detect or otherwise identify when one or more measurement values in the sequence are invalid, unreliable, unacceptable, or otherwise unusable. In this regard, a measurement value is unusable when one or more characteristics of the measurement value is indicative of the measurement value being corrupted, unreliable, or otherwise unacceptable for purposes of determining a predicted value based thereon. In response to detecting an unusable measurement value in a sensor measurement data sequence, the sensing arrangement 504 and/or the pump control system 520 modifies the sensor measurement data sequence to ameliorate the invalid measurement value, for example, by interpolating that value in the measurement sequence using acceptable measurement values that precede and succeed the unusable measurement or replacing the unusable measurement value in the sequence with a value of a succeeding measurement value in the sequence. In this manner, by virtue of modifying the sensor measurement data sequence and calculating the predicted value in a deterministic manner, a relatively reliable predicted value may be determined and utilized without having to reset the prediction calculation (e.g., deleting or discarding the measurement sequence) and/or incur the additional lag time associated with resetting the prediction calculation and/or waiting for a complete sequence of usable values to be obtained (e.g., the time required for the data sequence to be filled with the usable measurement values).

Again, it should be understood that FIG. 5 depicts a simplified representation of the infusion device 502 for purposes of explanation and is not intended to limit the subject matter described herein in any way. In this regard, depending on the embodiment, some features and/or functionality of the sensing arrangement 504 may implemented by or otherwise integrated into the pump control system 520, or vice versa. Similarly, in practice, the features and/or functionality of the motor control module 512 may implemented by or otherwise integrated into the pump control system 520, or vice versa. Furthermore, the features and/or functionality of the pump control system 520 may be implemented by control electronics 224 located in the fluid infusion device 200, 400, while in alternative embodiments, the pump control system 520 may be implemented by a remote computing device that is physically distinct and/or separate from the infusion device 502, such as, for example, the CCD 106 or the computer 108. Additionally, although FIG. 5 depicts the sensing arrangement 504 as being physically separate and distinct from the infusion device 502, in alternative embodiments, the sensing arrangement 504 may be integrated into or otherwise implemented by the infusion device 502 (e.g., by providing the sensing arrangement 504 within the housing 202).

Figure 6:
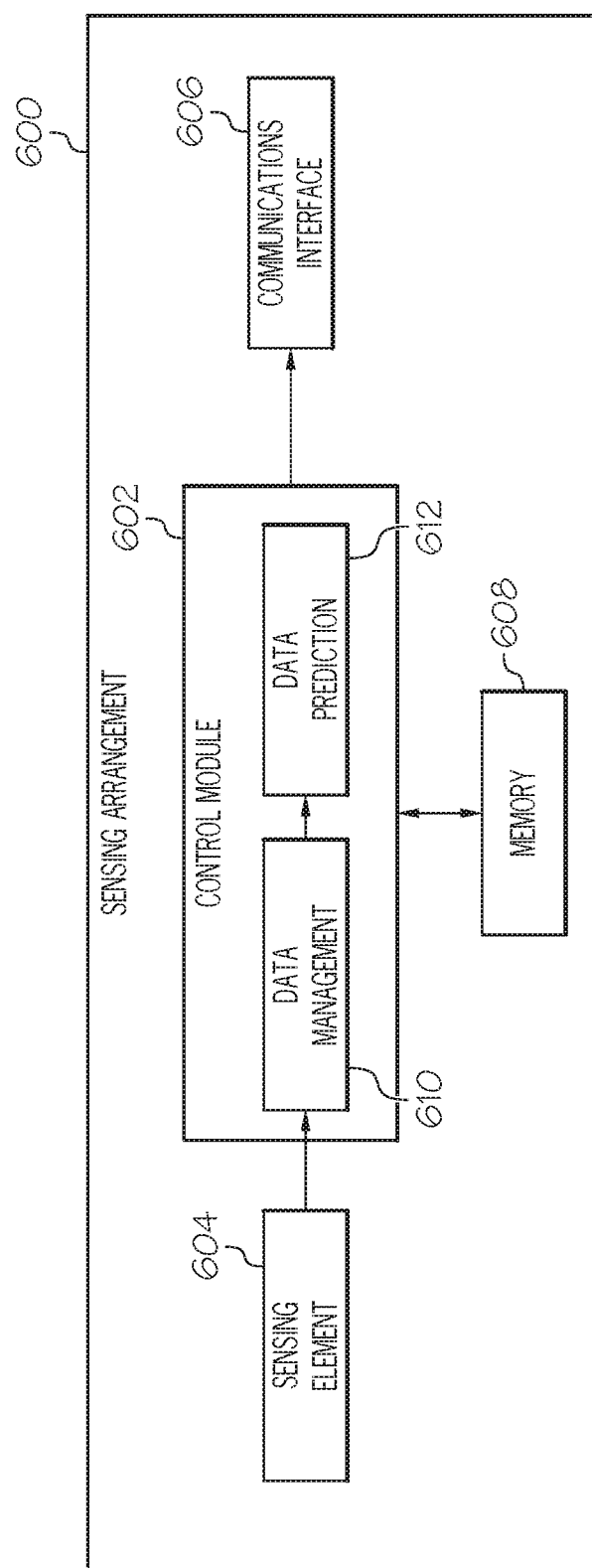
FIG. 6 is a block diagram of an exemplary sensing arrangement suitable for use in the control system of FIG. 5.

FIG. 6 depicts an exemplary embodiment of a sensing arrangement 600 suitable for use as the sensing arrangement 504 in FIG. 5 in accordance with one or more embodiments. The illustrated sensing arrangement 600 includes, without limitation, a control module 602, a sensing element 604, a communications interface 606, and a data storage element (or memory) 608. The control module 602 is coupled to the sensing element 604, the communications interface 606, and the memory 608, and the control module 602 is suitably configured to support the operations, tasks, and/or processes described herein.

The sensing element 604 generally represents the component of the sensing arrangement 600 that are configured to generate, produce, or otherwise output one or more electrical signals indicative of a characteristic that is sensed, measured, or otherwise quantified by the sensing arrangement. In this regard, a characteristic of the output electrical signal provided by the sensing element 604 corresponds or is otherwise correlative to the characteristic that the sensing element 604 senses, detects, measures, or otherwise quantifies. For example, referring to FIG. 5, the sensing element 604 may be realized as a glucose sensing element that generates an electrical signal, wherein a current (or voltage) associated with the electrical signal is correlative to the blood glucose level that is sensed or otherwise measured in the body 501 of the user.

Still referring to FIG. 6, the control module 602 generally represents the hardware, circuitry, logic, firmware and/or other component of the sensing arrangement 600 that is coupled to the sensing element 604, and the control module 602 is configured to receive the measurement data from the sensing element 604 and perform various additional tasks, operations, functions and/or operations described herein. For example, in one or more embodiments, the control module 602 implements or otherwise executes a data management application 610 that processes the measurement data received from the sensing element 604 to detect or otherwise identify whether measurement data value received from the sensing element 604 is valid or otherwise acceptable, and when a measurement data value is unacceptable, the data management application 610 substitutes a modified measurement data value for the unacceptable measurement data value in a data sequence of the most recent measurement data values. Additionally, in one or more embodiments, the control module 602 also implements or otherwise executes a data prediction application 612 that calculates or otherwise determines one or more predicted values for the characteristic sensed by the sensing element 604 based on the sequence of the most recent measurement data values received from the data management application 610. In this regard, a predicted value for the sensed characteristic at a time in the future may be influenced by or otherwise based at least in part on the modified measurement data value substituted by the data management application 610 in lieu of the unacceptable measurement data value received from the sensing element 604, as described in greater detail below.

Depending on the embodiment, the control module 602 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 602, or in any practical combination thereof. In some embodiments, the control module 602 includes an analog-to-digital converter (ADC) or another similar sampling arrangement that converts the output data signal received from the sensing element 604 into corresponding digital measurement data value. For example, the control module 602 may convert an output electrical signal received from the sensing element 604 into corresponding digital measurement value (e.g., an uncalibrated glucose sensor electrical current value).

In exemplary embodiments, the control module 602 includes or otherwise accesses the data storage element or memory 608. The memory 608 may be realized using any sort of RAM, ROM, flash memory, registers, hard disks, removable disks, magnetic or optical mass storage, short or long term storage media, or any other non-transitory computer-readable medium capable of storing programming instructions for execution by the control module 602. The computer-executable programming instructions, when read and executed by the control module 602, cause the control module 602 to implement or otherwise generate the applications 610, 612 and perform the tasks, operations, functions, and processes described in greater detail below.

The communications interface 606 generally represents the hardware, circuitry, logic, firmware and/or other components of the sensing arrangement 600 that are coupled to the control module 602 and configured to support communications to/from the sensing arrangement 600. The communications interface 606 may include or otherwise be coupled to one or more transceiver modules capable of supporting wireless communications between the sensing arrangement 600 and another electronic device (e.g., an infusion device 102, 502 or another electronic device 106, 108 in an infusion system 100). Alternatively, the communications interface 606 may be realized as a port that is adapted to receive or otherwise be coupled to a wireless adapter that includes one or more transceiver modules and/or other components that support the operations of the sensing arrangement 600 described herein. In other embodiments, the communications interface 606 may be configured to support wired communications to/from the sensing arrangement 600.

It should be understood that FIG. 6 is a simplified representation of a sensing arrangement 600 for purposes of explanation and is not intended to limit the subject matter described herein in any way. In this regard, although FIG. 6 depicts the various elements residing within the sensing arrangement 600, one or more elements of the sensing arrangement 600 may be distinct or otherwise separate from the other elements of the sensing arrangement 600. For example, the sensing element 604 may be separate and/or physically distinct from the control module 602 and/or the communications interface 606. Furthermore, although FIG. 6 depicts the data management application 610 and the data prediction application 612 as being implemented by the sensing arrangement 600, in alternative embodiments, features and/or functionality of the data management application 610 and/or the data prediction application 612 may be implemented by or otherwise reside on the infusion device 102, 502 or another device 106, 108 within an infusion system 100. For example, as described in greater detail below, in some embodiments, the data management application 610 implemented by the sensing arrangement 600 may merely detect or otherwise identify unacceptable measurement data values and provide a corresponding notification of the unacceptable measurement data value to the infusion device 102, 502, which, in turn, substitutes a modified measurement data value for the unacceptable measurement data value and determines one or more predicted values for the sensed characteristic based thereon.

Figure 7:
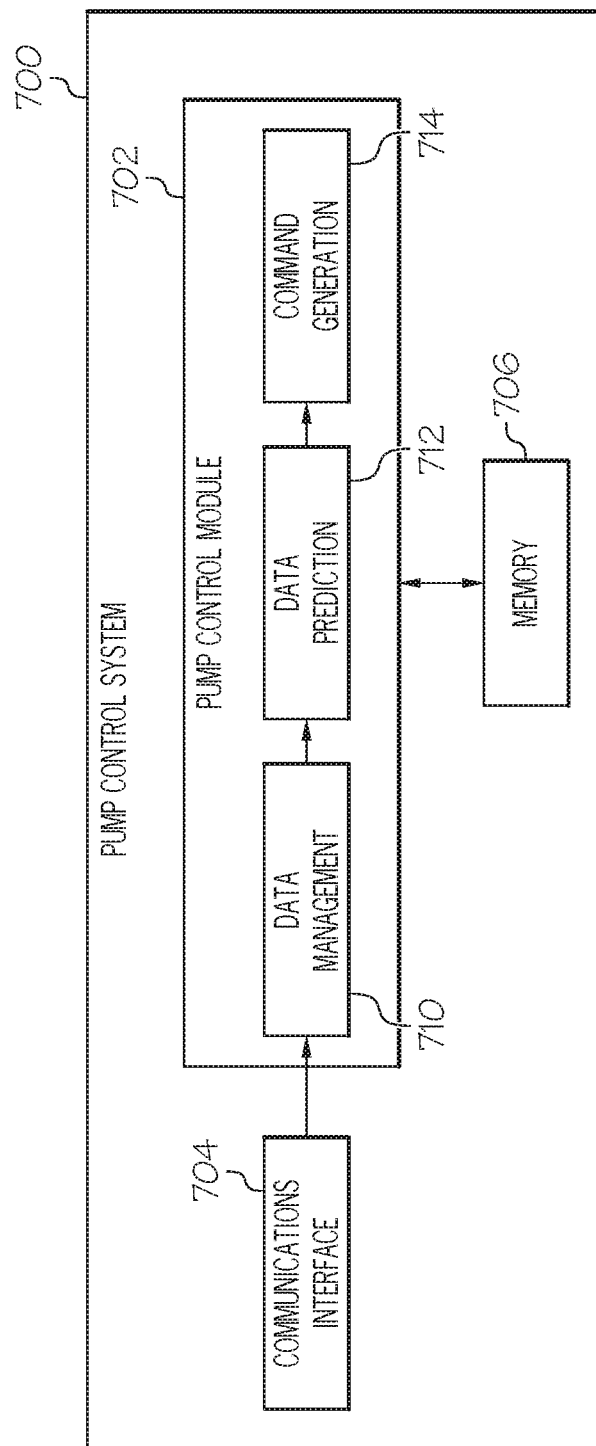
FIG. 7 is a block diagram of an exemplary pump control system suitable for use in the control system of FIG. 5.

FIG. 7 depicts an exemplary embodiment of a pump control system 700 suitable for use as the pump control system 520 in FIG. 5 in accordance with one or more embodiments. The illustrated pump control system 700 includes, without limitation, a pump control module 702, a communications interface 704, and a data storage element (or memory) 706. The pump control module 702 is coupled to the communications interface 704 and the memory 706, and the pump control module 702 is suitably configured to support the operations, tasks, and/or processes described herein.

Referring to FIG. 7 and with reference to FIG. 5, the communications interface 704 generally represents the hardware, circuitry, logic, firmware and/or other components of the pump control system 700 that are coupled to the pump control module 702 and configured to support communications between the pump control system 700 and the sensing arrangement 504. In this regard, the communications interface 704 may include or otherwise be coupled to one or more transceiver modules capable of supporting wireless communications between the pump control system 520, 700 and the sensing arrangement 504 or another electronic device 106, 108 in an infusion system 100. In other embodiments, the communications interface 704 may be configured to support wired communications to/from the sensing arrangement 504.

The pump control module 702 generally represents the hardware, circuitry, logic, firmware and/or other component of the pump control system 700 that is coupled to the communications interface 704 and configured to determine dosage commands for operating the motor 507 to deliver fluid to the body 501 based on data received from the sensing arrangement 504 and perform various additional tasks, operations, functions and/or operations described herein. For example, in exemplary embodiments, pump control module 702 implements or otherwise executes a command generation application 714 that calculates or otherwise determines a dosage command for operating the motor 507 of the infusion device 502 based at least in part on a current measurement value for a condition in the body 501 of the user, a predicted measurement value for that condition in the body 501 of the user, and one or more reference (or target) values for that condition in the body 501 of the user. For example, the command generation application 714 may determine a dosage command for operating the motor 507 to deliver insulin to the body 501 of the user based at least in part on a current blood glucose measurement value, a predicted blood glucose measurement value at a time in the future (e.g., in 30 minutes from the current time), and a reference glucose value. For example, the reference value may be equal to the threshold blood glucose value at which insulin delivery should be suspended, wherein the command generation application 714 sets the dosage command to zero to suspend operation of the motor 507 (and thereby, suspend delivery) when the current blood glucose measurement value is less than or equal to the threshold blood glucose value. Conversely, when the current blood glucose measurement value is greater than a threshold blood glucose value (e.g., the resume delivery threshold), the command generation application 714 may determine a nonzero dosage command for operating the motor 507 to deliver insulin to the body 501 of the user based at least in part on the current blood glucose measurement value. In the case of closed-loop control, the dosage command determined by the command generation application 714 may be configured to regulate the user's blood glucose level to a target blood glucose value.

Referring to FIG. 7 with reference to FIGS. 5-6, in some embodiments, the pump control module 702 may also implement or otherwise execute a data prediction application 712 and/or a data management application 710 in lieu of and/or in addition to the applications 610, 612 being implemented by the sensing arrangement 504, 600. In this regard, in some embodiments, the sensing arrangement 504, 600 may merely transmit the current measurement value and/or a sequence of recent measurement values, either with or without indications of whether those measurement values are valid and/or acceptable. In such embodiments, the data management application 710 on the pump control module 702 may process the measurement data received from the sensing arrangement 504, 600 to detect or otherwise identify whether any of the measurement data values received from the sensing arrangement 504, 600 are invalid or otherwise unacceptable. In this regard, the data management application 710 may also detect or otherwise measurement data values that were dropped, lost, or otherwise failed to be received by the communications interface 704. In a similar manner as described above, the data management application 710 substitutes a modified measurement data value for an unacceptable measurement data value to provide a modified data sequence for the most recent measurement data values. Similarly, in one or more embodiments, the pump control module 702 may also implement or otherwise execute a data prediction application 712 that calculates or otherwise determines one or more predicted values for the characteristic quantified by the sensing arrangement 504, 600 based on the sequence of the most recent measurement data values provided by the data management application 610. Thus, a predicted value for a sensed characteristic at a time in the future may be influenced by or otherwise based at least in part on the modified data sequence provided by data management application 710, as described in greater detail below.

Still referring to FIG. 7, depending on the embodiment, the control module 702 may be implemented or realized with a general purpose processor, a microprocessor, a controller, a microcontroller, a state machine, a content addressable memory, an application specific integrated circuit, a field programmable gate array, any suitable programmable logic device, discrete gate or transistor logic, discrete hardware components, or any combination thereof, designed to perform the functions described herein. In this regard, the steps of a method or algorithm described in connection with the embodiments disclosed herein may be embodied directly in hardware, in firmware, in a software module executed by the control module 702, or in any practical combination thereof. In exemplary embodiments, the pump control module 702 includes or otherwise accesses the data storage element or memory 708, which may be realized using any sort of non-transitory computer-readable medium capable of storing programming instructions for execution by the pump control module 702. The computer-executable programming instructions, when read and executed by the control module 702, cause the control module 702 to implement or otherwise generate one or more of the applications 710, 712, 714 and perform the tasks, operations, functions, and processes described in greater detail below.

It should be understood that FIG. 7 is a simplified representation of a pump control system 700 for purposes of explanation and is not intended to limit the subject matter described herein in any way. For example, in some embodiments where the sensing arrangement 504, 600 implements the features and/or functionality of the data management application 710 and/or the data prediction application 712, such applications 710, 712 may be absent from the pump control system 700. Furthermore, in some embodiments, the features and/or functionality of the motor control module 512 may be implemented by or otherwise integrated into the pump control system 700 and/or the pump control module 702, for example, by the command generation application 714 converting the dosage command into a corresponding motor command, in which case, the separate motor control module 512 may be absent from an embodiment of the infusion device 502.

FIG. 8 depicts an exemplary control process 800 suitable for implementation by a control system in a fluid infusion device, such as the control system 500 in the infusion device 502, to determine commands for operating a motor to deliver fluid to a user in a manner that is influenced by one or more predicted measurement values for a condition of the user at some point in the future. The various tasks performed in connection with the control process 800 may be performed by hardware, firmware, software executed by processing circuitry, or any combination thereof. For illustrative purposes, the following description refers to elements mentioned above in connection with FIGS. 1-7. In practice, portions of the control process 800 may be performed by different elements of the control system 500, such as, for example, the infusion device 502, the sensing arrangement 504, 600, the pump control system 520, 700, the motor control module 512, and/or the motor 507. It should be appreciated that the control process 800 may include any number of additional or alternative tasks, the tasks need not be performed in the illustrated order and/or the tasks may be performed concurrently, and/or the control process 800 may be incorporated into a more comprehensive procedure or process having additional functionality not described in detail herein. Moreover, one or more of the tasks shown and described in the context of FIG. 8 could be omitted from a practical embodiment of the control process 800 as long as the intended overall functionality remains intact.

In exemplary embodiments, the control process 800 initializes or otherwise begins by receiving or otherwise obtaining a new measurement data value (or sample) for a condition in the body of a user and updating a measurement data sequence of recent measurement data values for the user to include the new measurement data value (task 802, 804). In this regard, the control module 602 may sample, poll, or otherwise operate the sensing element 604 to obtain a new sample of the level of a condition in the body 501 of the user. In exemplary embodiments, the control module 602 obtains the new sample from the sensing element 604 on a regular periodic basis. For example, the control module 602 may sample the output of the sensing element 604 every five minutes to obtain a new measurement of the blood glucose level in the body 501 of the user. After obtaining a new sample, the control module 602 may obtain a stored sequence of recent measurement samples from the memory 608, add the new sample to the sequence of recent measurement samples, and shift the precedence of the previous measurement samples to follow the new measurement sample in the updated measurement sequence. For example, the sequence of recent measurement samples may be realized as a first-in first-out (FIFO) queue of measurement samples that are ordered sequentially, where the control module 602 updates the sequence of recent measurement samples by adding the measurement value for the new sample to the FIFO queue and removing the value of the oldest measurement sample from the queue. For purposes of explanation, the new or most measurement data value (or sample) may alternatively be referred to herein as the current measurement data value (or sample). In one or more embodiments, after updating the measurement data sequence, the data management application 610 stores or otherwise maintains the updated measurement sequence in memory 608, for example, by overwriting the previously stored measurement sequence. In some embodiments, the memory 608 may maintain the previously stored measurement sequence and the current (or updated) measurement sequence in memory 608 to support interpolating unusable measurement values using acceptable measurement values from the preceding stored measurement sequence, as described in greater detail below in the context of FIGS. 9-10.

Still referring to FIG. 8, the illustrated control process 800 continues by determining whether the new measurement sample is usable, and in response to determining that the new measurement sample is unusable, the control process 800 flags or otherwise indicates that the new measurement sample is unusable (tasks 806, 808). In this regard, when implemented by the sensing arrangement 504, 600, the data management application 610 applies various validation criteria and/or logic to the new measurement sample to verify that the new measurement sample is sufficiently accurate and/or reliable before the new measurement sample is capable of influencing operation of the infusion device 502. For example, the data management application 610 may ensure that the new measurement sample is greater than a minimum threshold value, less than a maximum threshold value, or otherwise within a range of acceptable valid measurement values for the condition in the body 501 of the user. Similarly, the data management application 610 may calculate or otherwise obtain one or more characteristics associated with the new measurement sample and ensure an obtained characteristic is greater than a minimum threshold value, less than a maximum threshold value, or otherwise within a range of acceptable values for that characteristic of the new measurement sample. For example, the data management application 610 may determine or obtain a signal-to-noise ratio associated with the new measurement sample and compare the signal-to-noise ratio to a minimum acceptable signal-to-noise ratio to ensure that the measurement value is not likely to have been corrupted or overly influenced by noise.

When the data management application 610 determines the new measurement sample is unusable (e.g., because its value is not within the range of acceptable valid measurement values, its signal-to-noise ratio is too low, or the like), the data management application 610 may flag or otherwise mark the new measurement sample as being invalid or otherwise unusable so that the measurement value is not utilized when determining commands for operating the motor 507 of the infusion device 502. For example, in some embodiments, the data management application 610 may replace the measurement value with an error code. In other embodiments, the sequence of recent measurement samples may maintain, in association with each respective measurement sample in the sequence, an indication of whether that respective measurement sample is acceptable or otherwise usable for subsequently determining dosage commands.

In accordance with one or more embodiments, when the current measurement sample is unusable, the sensing arrangement 504, 600 also transmits or otherwise provides the current measurement value and/or the updated measurement sample sequence to the infusion device 502 and/or the pump control system 520, 700 with a corresponding indication or notification that the current (or most recent) measurement is unacceptable. For example, the sensing arrangement 504, 600 may transmit or otherwise provide an error code for the current measurement sample or another indication that the current measurement sample is unusable or otherwise unacceptable. In some embodiments, when the infusion device 502 and/or the pump control system 520, 700 receives an error code for the current measurement sample or another an indication that the current measurement sample is unusable or otherwise unacceptable, the pump control system 520, 700 and/or the command generation application 714 may implement a modified control scheme or algorithm for determining dosage commands independent of any current and/or predicted measurement values in a manner that is likely to maintain the condition in the body 501 of the user within an acceptable range. In accordance with one embodiment, when the delivery has been suspended and more than a threshold number of unusable measurement samples have been received by the infusion device 502 while delivery is suspended, the pump control system 520, 700 and/or the command generation application 714 may automatically resume delivery.

Still referring to FIG. 8, when the new measurement sample is acceptable and usable, the control process 800 continues by determining whether the sequence of recent measurement samples is valid or otherwise acceptable for use in subsequently determining dosage commands for operating the infusion device (task 810). In this regard, the data management application 610 analyzes each measurement sample in the recent measurement sample sequence to ensure that none of the measurement samples has been flagged or otherwise identified as being unusable. When all of the measurement samples in the recent measurement sample sequence are usable, the control process 800 determines the measurement sequence is valid and acceptable and proceeds with determining a predicted measurement value for the condition in the body of the user at a time in the future and determining dosage commands for operating the infusion device in a manner that is influenced by the predicted measurement value (tasks 818, 820), in a similar manner as described below.

In exemplary embodiments, when the control process 800 determines that the sequence of recent measurement samples is invalid or otherwise unacceptable, the control process 800 continues by determining whether the recent measurement sample sequence can be interpolated to substitute modified measurement values for the measurement samples that have been flagged or otherwise identified as being unusable (task 812). In this regard, the data management application 610 determines whether the difference between two sequential usable values is less than or equal to a threshold number of measurement samples. The threshold number of measurement samples corresponds to a threshold amount of time that is short enough in duration that interpolating the recent measurement sample sequence to replace the unusable measurement samples between two sequential acceptable values allows any predicted measurement values calculated based thereon to achieve a desired level of accuracy and/or reliability. For example, if it is determined that gaps between sequential usable values that are less than or equal to 20 minutes can be interpolated and still result in predicted measurement values having a desired level of accuracy and/or reliability, then the threshold number of measurement samples may be chosen to be the number of measurement samples that would be expected to be obtained within a 20 minute timeframe. Continuing the example described above, if the new measurement samples are obtained every 5 minutes, a threshold number of measurement samples between sequential usable measurement values equal to 3 measurement samples will allow gaps of up to 20 minutes between usable measurement values to be interpolated. Thus, the data management application 610 may interpolate between any two usable measurement samples that are separated by three or fewer unusable measurement samples to obtain a modified (or adjusted) recent measurement sample sequence that does not include any invalid and/or unusable measurement values.

If the unusable measurement sample(s) in the recent measurement sample sequence can be interpolated, the control process 800 continues by performing interpolation using preceding and succeeding usable measurement samples in the measurement sequence to obtain one or more interpolated measurement values corresponding to one or more unusable measurement samples in the recent measurement sample sequence (task 814). The recent measurement sample sequence is then modified or otherwise adjusted by substituting the interpolated measurement values for the corresponding unusable measurement values, resulting in a modified (or adjusted) recent measurement sample sequence that does not include unusable measurement values for samples in the sequence that have been identified as unusable. For example, the data management application 610 may perform interpolation using any number of acceptable measurement samples that precede and/or succeed an unusable measurement sample (or consecutive unusable measurement samples) to determine interpolated measurement values for the unusable measurement sample(s). In accordance with one embodiment, the data management application 610 utilizes linear interpolation to obtain an interpolated measurement value for an unusable measurement sample(s) between two usable measurement samples. However, it should be appreciated that the subject matter described herein is not limited to any particular type of interpolation utilized to replace unusable measurement samples. In some embodiments, after modifying the measurement data sequence, the data management application 610 may store or otherwise maintain the modified measurement sequence in memory 608. In other embodiments, the data management application 610 may provide the modified measurement sequence to the data prediction application 612 while storing or otherwise maintaining the original unmodified measurement sequence in memory 608.

When the control process 800 determines recent measurement sample sequence cannot be interpolated, the control process 800 continues by replacing unusable measurement samples in the recent measurement sample sequence with the value of a more recently obtained usable measurement value (task 816). In this regard, when the number of consecutive unusable measurement samples exceeds a threshold number of measurement samples that are allowed to be interpolated (alternatively referred to herein as the interpolatable threshold), those consecutive unusable measurement samples are replaced with the more recent measurement data value that succeeds or follows those unusable measurement samples in the recent measurement sample sequence. In other words, the data management application 610 backfills consecutive unusable measurement samples that exceed the interpolatable threshold with the more recent usable measurement data value that immediately follows those consecutive unusable measurement samples. In some embodiments, any usable measurement samples that precede the consecutive unusable measurement samples in the recent measurement sample sequence are also replaced or otherwise backfilled to eliminate any potential spike, jump or other discontinuity at the transition from those prior usable measurement samples to the current measurement sample value being backfilled. For example, continuing the example described above, if the interpolatable threshold number of measurement samples is equal to 3 and the number of consecutive unusable measurement samples is greater than or equal to 4, the data management application 610 may replace the consecutive unusable measurement samples and any older measurement samples in the recent measurement sample sequence with the usable measurement value that immediately follows the consecutive unusable measurement samples in the sequence.

It should be noted that in some embodiments of the control process 800, both interpolation and replacement may be performed on a measurement data sequence to obtain a modified measurement data sequence. For example, as described in greater detail below in the context of FIGS. 9-10, in situations where there are multiple sets of consecutive unusable measurement samples in the sequence, any set of consecutive unusable measurement samples that has fewer than the interpolatable threshold number may be interpolated while any set of consecutive unusable measurement samples that has greater than the interpolatable threshold number may be replaced with the immediately following usable measurement value.

Additionally, it should also be noted that in some embodiments of the control process 800, when the measurement sequence is incomplete or otherwise does not contain the steady state number of measurement samples, the control process 800 may determine that the measurement sequence is not valid and acceptable (e.g., because it does not contain the desired amount of usable measurement values), in which case the control process 800 may proceed by backfilling the measurement sequence using the oldest usable measurement value in the measurement sequence. For example, the measurement sequence in memory 608 may initially be populated with an error code, a null value, or the like, thereby indicating the samples in the initial measurement sequence are not usable. If the measurement sequence contains 9 samples at steady state and the current measurement sequence contains only 2 usable samples, the control process 800 may backfill the measurement sequence with the least recent of the usable samples to obtain a complete modified measurement data sequence with the steady state number of measurement sample values. In this regard, upon initialization of the control system 500, predicted values for the condition in the body 501 of the user may still be calculated. Furthermore, in yet other embodiments, a complete modified measurement data sequence may be obtained by extrapolating the usable measurement data values backwards to fill the measurement data sequence.

Still referring to FIG. 8, after obtaining a modified recent measurement sample sequence, the control process 800 continues by determining a predicted measurement value for the condition in the body of the user at a time in the future (task 818). In exemplary embodiments, the data prediction application 612 calculates the predicted measurement value based at least in part on the current measurement data value and a weighted sum determined using the measurement data values in the recent measurement sample sequence received from the data management application 610 and/or memory 608. Thus, when one or more previously unusable measurement samples have been modified, either by interpolation or replacement with a more recent value, the predicted measurement value is calculated or otherwise determined based at least in part on those modified measurement data values in addition to the originally acceptable measurement values maintained in the modified measurement sequence.

In one or more exemplary embodiments, a predicted blood glucose level in the body 501 of the user at a time in the future is calculated using the equation $\hat{y}=y_t+hb_t$, where $\hat{y}$ is the predicted blood glucose level, $y_t$ is equal to the current (or most recent) blood glucose measurement value, h is the prediction horizon in terms of number of measurement samples in the future from the current time, and $b_t$ is the estimate of the trend in the measurements that is determined as a weighted sum of the measurement values in the recent measurement sequence. In exemplary embodiments, $b_t$ is governed by the equation $$b_t = \sum_{k=1}^{n} \beta(1-\beta)^{(k-1)} b_{t-k},$$

where $\beta$ is a tuning parameter, n is equal to the number of older blood glucose measurement values in the measurement sequence that precede the current measurement value. The $b_{t-k}$ term is calculated as the difference between the $k^{th}$ blood glucose measurement value preceding the current measurement value in the measurement sequence and the blood glucose measurement value that immediately precedes the $k^{th}$ blood glucose measurement value in the measurement sequence (e.g., $b_{t-k}=y_{t-k}-y_{t-k-1}$). In this regard, t corresponds to the current (or most recent) measurement sampling time (e.g., $y_t$ is the first or most recent measurement sample in the sequence), t−1 corresponds to the preceding (or next most recent) measurement sampling time (e.g., $y_{t-1}$ is the second most recent measurement sample in the sequence), and so on, such that $y_{t-n}$ corresponds to the oldest (or least recent) measurement sample in the sequence. It should be noted that the estimate of the trend is calculated in a deterministic manner rather than a recursive manner using a truncated Taylor series expansion of the equation $b_t=\beta(y_t-y_{t-1})+(1-\beta)b_{t-1}$, which, in turn, allows the estimate of the trend to be calculated using a modified data sequence in the event of unusable measurement samples rather than having to reinitialize the calculation. In one embodiment, the anticipated (or expected) blood glucose level in the body 501 of the user 30 minutes into the future. Thus, continuing the above example, if the measurement samples are obtained every 5 minutes, the predicted blood glucose level 30 minutes into the future ($\hat{y}$) is calculated by setting h=6, which corresponds to the number of measurement samples that would be obtained over a 30 minute duration of time.

After determining a predicted measurement value, the control process 800 continues by determining commands for operating the infusion device in a manner that is influenced by the predicted measurement value (task 820). For example, the sensing arrangement 504, 600 may transmit or otherwise provide the current blood glucose measurement value ($y_t$) and the predicted blood glucose measurement value ($\hat{y}$) in the body 501 of the user 30 minutes into the future to the pump control system 520, 700. Thereafter, the pump control system 520, 700 and/or command generation application 714 determines a dosage command based on the current blood glucose measurement value and one or more target blood glucose measurement value in a manner that is influenced by or otherwise accounts for the predicted blood glucose measurement value. For example, the pump control system 520, 700 and/or command generation application 714 may determine an initial dosage command based on a difference between the current blood glucose measurement value and a target blood glucose measurement value, and then utilize the predicted blood glucose measurement value as a modification factor that increases and/or decreases that dosage command, which is then provided to the motor control module 512 for generating appropriate motor commands. In some embodiments, the pump control system 520, 700 and/or command generation application 714 may set the dosage command to zero when the predicted blood glucose value is less than a lower threshold blood glucose level. As described above in the context of FIG. 5, in response to receiving a dosage command, the motor control module 512 may convert the dosage command to a corresponding motor command (e.g., a number of steps of rotor rotation) that will displace the plunger 517 by an amount corresponding to the desired dosage and then operate the motor 507 to achieve the desired displacement of the plunger 517. In this manner, delivery of the desired amount of fluid from the infusion device 502 to the body 501 of the user is achieved.

Still referring to FIG. 8, while the foregoing discussion of the control process 800 was described in the context of the sensing arrangement 504, 600 detecting or otherwise identifying acceptable and/or unusable measurement samples and/or measurement sequences, modifying measurement sequences, and determining predicted measurement values, in alternative embodiments, one or more of those aspects may be performed by the infusion device 502 and/or the pump control system 520, 700. For example, in one alternative embodiment, the sensing arrangement 504, 600 may merely obtain a new measurement value and transmit the new measurement value to the pump control system 520, 700, whereby the data management application 710 on the pump control module 702 manages or otherwise maintains the sequence of recent measurement values and determines whether the new measurement value is acceptable. In such embodiments, the pump control system 520, 700 may also account for measurement values that may have been dropped or otherwise lost in transmission from the sensing arrangement 504, 600 that were not received by the communications interface 704. For example, if the sensing arrangement 504, 600 obtains and transmits a new measurement value every 5 minutes, the data management application 710 may automatically identify an absent measurement sample and update the measurement sequence to reflect a new unusable measurement sample in response to a failure to receive a new measurement value 5 minutes (plus or minus a particular time window or margin for error) after the most recently obtained measurement sample. In a similar manner as described above, the data management application 710 on the pump control module 702 may also detect or otherwise identify an unacceptable and/or invalid data sequence and modify the measurement sequence using one or more acceptable measurement values within the measurement sequence (e.g., tasks 810, 812, 814, 816). Thereafter, the data prediction application 712 on the pump control module 702 determines a predicted measurement value that is provided to the command generation application 714 for generating operating commands for the infusion device 502 (e.g., tasks 818, 820), as described above.

In one or more embodiments, the sensing arrangement 504, 600 obtains new measurement values, updates the measurement sequences, and transmits the measurement sequences with a corresponding indication of any unusable measurement values in a measurement sequence (e.g., tasks 802, 804, 806, 808). In such embodiments, the data management application 710 on the pump control module 702 receives a measurement sequence from the sensing arrangement 504, 600 and determines whether the measurement sequence needs to be modified for subsequent usage (e.g., task 810). In this regard, the data management application 710 may modify unusable measurement values indicated by the sensing arrangement 504, 600 while also accounting for any measurement samples that may have been dropped or otherwise lost in transmission from the sensing arrangement 504, 600. For example, the data management application 710 may also identify absent or missing measurement samples within a measurement sequence received from the sensing arrangement 504, 600 that were likely dropped, lost, or otherwise corrupted during transmission.

FIG. 9 is depicts a table 900 including exemplary measurement sequences, and FIG. 10 depicts a table 1000 corresponding to the measurement sequences in the table 900 of FIG. 9 after invalid and/or unacceptable measurement sequences have been modified and a corresponding predicted value based thereon has been calculated using a in conjunction with the control process 800 described above. In FIG. 9, unusable measurement samples are identified by setting the corresponding measurement value to a null value. As described above, the unusable measurement samples could be measurement samples that did not result in a valid measurement value (e.g., an original measurement value outside the range of valid values for the sensing element 604), measurement samples having a low signal-to-noise ratio that are susceptible to being corrupted by noise, absent measurement samples that were lost or otherwise failed to be received by the infusion device 502, or the like. The first row of the tables 900, 1000 depicts a valid measurement sequence where all of the individual measurement samples are originally valid and acceptable. In the illustrated embodiment, the predicted values depicted in the table 1000 are calculated for the time 6 measurement samples into the future (e.g., h=6) with a tuning parameter of 0.3 (e.g., β=0.3).

The second row in the table 900 depicts a measurement sequence where a difference between two sequential usable measurement samples (e.g., $y_t$ and $y_{t-4}$) is equal to interpolatable number of measurement samples (e.g., 3 measurement samples corresponding to an allowable gap of 20 minutes between $y_t$ and $y_{t-4}$). The second row in table 1000 depicts the modified measurement sequence obtained by performing linear interpolation between the usable measurement values for $y_t$ and $y_{t-4}$ to replace the measurement samples between $y_t$ and $y_{t-4}$ with interpolated measurement values and the corresponding predicted measurement value calculated using those interpolated measurement values.

The third row in the table 900 depicts a measurement sequence where the difference between usable measurement samples $y_t$ and $y_{t-6}$ and the difference between usable measurement samples $y_{t-4}$ and $y_{t-1}$ are both less than or equal to the interpolatable number of measurement samples. The third row in table 1000 depicts the modified measurement sequence obtained by performing linear interpolation between the usable measurement values for $y_{t-8}$ and $y_{t-6}$ to obtain an interpolated value for $y_{t-7}$ and performing linear interpolation between the usable measurement values for $y_{t-4}$ and $y_{t-1}$ to obtain interpolated values for $y_{t-3}$ and $y_{t-2}$.

The fourth row in the tables 900, 1000 depicts a modified measurement sequence where a usable measurement sample (e.g., $y_{t-9}$) from a previously stored measurement sequence in memory 608, 706 is used to interpolate and replace the oldest measurement sample(s) in a current measurement sequence when the next preceding measurement value was an acceptable measurement value (e.g., $y_{t-9}=1$).

The fifth row in the table 900 depicts a measurement sequence where the difference between two sequential usable measurement samples $y_{t-1}$ and $y_{t-6}$ is greater than the interpolatable number of measurement samples. The fifth row in table 1000 depicts the modified measurement sequence obtained by backfilling or otherwise replacing measurement samples older than $y_{t-1}$ with the measurement value for $y_{t-1}$. In this regard, originally acceptable measurement values for $y_{t-6}$, $y_{t-7}$, and $y_{t-8}$ may be overwritten with the value of $y_{t-1}$. In this manner, backfilling for $y_{t-6}$, $y_{t-7}$, and $y_{t-8}$ eliminates the spike or jump that could otherwise occur when transitioning from the original value of $y_{t-6}$ (e.g., 2) to the backfilled value for $y_{t-5}$ (e.g., 4.5) and effectively resets the prediction algorithm with the value of $y_{t-1}$.

The sixth row in the tables 900, 1000 depicts a modified measurement sequence where the oldest measurement samples are unusable and replaced with the value of the usable measurement sample that succeeds the unusable measurement samples in the sequence.

The seventh row in the table 900 depicts a measurement sequence where the oldest two measurement samples in the sequence are unusable and cannot be interpolated because the preceding measurement sample (e.g., $y_{t-9}$) is unavailable or unusable. At the same time, the difference between usable samples $y_{t-3}$ and $y_{t-6}$ is less than the interpolatable number of measurement samples. In this regard, the seventh row in table 1000 depicts the modified measurement sequence obtained by backfilling or otherwise replacing measurement samples $y_{t-7}$ and $y_{t-8}$ with the usable measurement value for $y_{t-6}$, while also performing linear interpolation between the usable measurement values for $y_{t-3}$ and $y_{t-6}$ to obtain interpolated values for $y_{t-4}$ and $y_{t-5}$.

As described above, by virtue of calculating the predicted measurement value in a deterministic manner rather than a recursive manner, any measurement values that are invalid, unacceptable, or otherwise missing from a measurement sequence may be interpolated or replaced using acceptable measurement value(s) to obtain a modified measurement sequence, which may then be utilized to calculate a predicted measurement value without compromising the accuracy and/or reliability of the prediction. In this regard, a predicted measurement value remains available to the pump control system 520, 700 for influencing operation of the infusion device 502, rather than having to disable the predictive control and wait until a complete and valid measurement sequence is available before resuming the predictive control.

Figure 11:
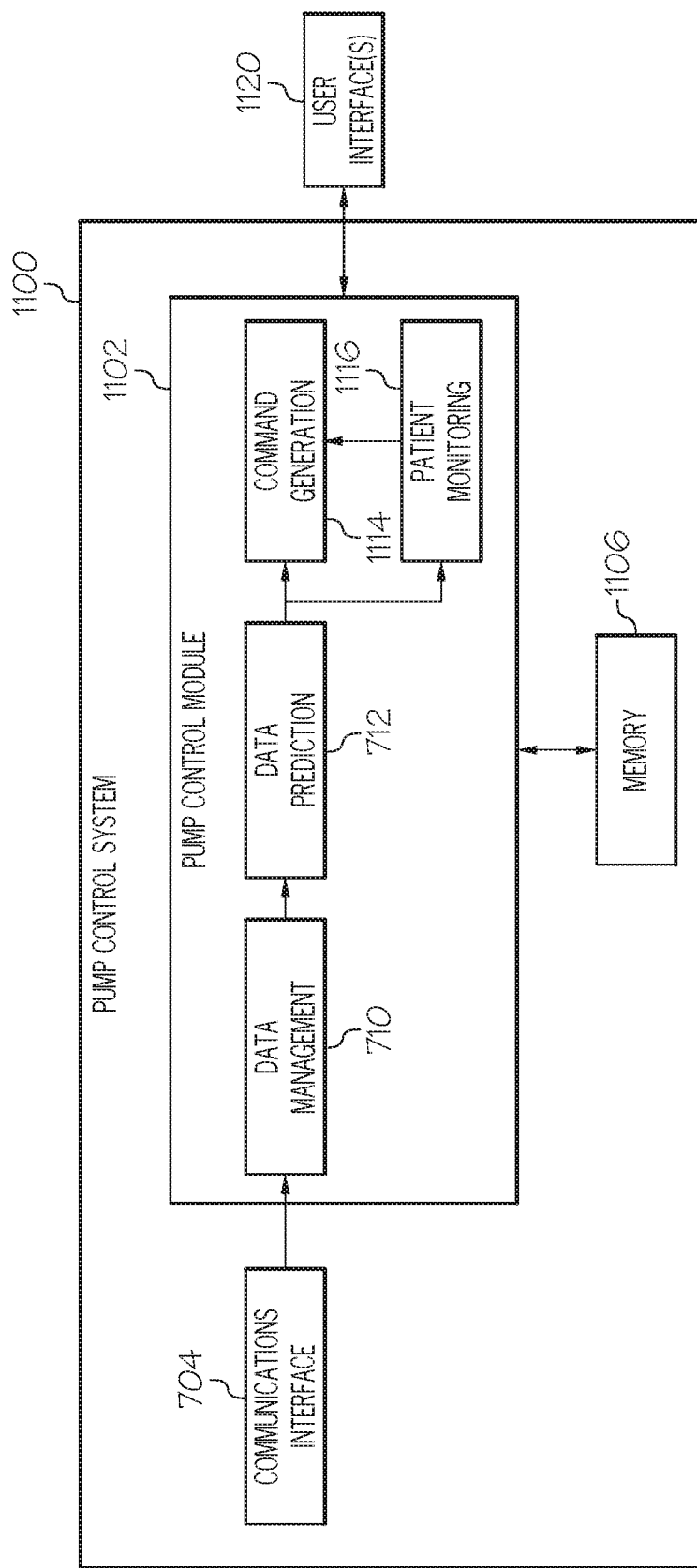
FIG. 11 depicts block diagram of an exemplary pump control system suitable for use in the control system of FIG. 5.

Referring now to FIG. 11, in one or more exemplary embodiments, a pump control system 1100 suitable for use as the pump control system 520 in FIG. 5 includes or otherwise implements a patient monitoring application 1116 configured automatically adjust the infusion device operating mode implemented by the command generation application 1114 and/or the pump control system 1100. It should be appreciated that the various elements of the pump control system 1100 are similar to counterpart elements described above in the context of the pump control system 700 of FIG. 7, and accordingly, such common features and/or functionality may not be redundantly described here in the context of FIG. 11. In this regard, the control module 1102 reads and executes the computer-executable programming instructions stored on the data storage element 1106 (or memory) to implement or otherwise generate the monitoring application 1116 in conjunction with the applications 710, 712, 1114 and perform the tasks, operations, functions, and processes described in greater detail below.

In the illustrated embodiment, the pump control module 1102 is coupled to one or more user interface elements 1120 to receive or otherwise obtain one or more user-configurable threshold values used by the monitoring application 1116 to automatically control the operating mode implemented by the command generation application 1114, such as, for example, a suspend protection threshold (SPT) value, a resume delivery protection threshold value, a minimum IOB threshold value, or the like. Thus, the one or more user interface element(s) 1120 include at least one input user interface element, such as, for example, a button, a keypad, a keyboard, a knob, a joystick, a mouse, a touch panel, a touchscreen, a microphone or another audio input device, and/or the like. The user input values obtained via a user interface element 1120 may be stored or otherwise maintained in the memory 1106 for future reference by the monitoring application 1116 during operation of the pump control system 1100. For example, the memory 1106 may include a dedicated register associated with the suspend delivery protection value that stores the SPT value received from a user via an input user interface element 1120.

Additionally, the pump control module 1110 may receive or otherwise obtain alert configuration information for the user associated with the infusion device 502 and generate or otherwise provide notifications to the user in accordance with that user's alert configuration while operating the infusion device 502. Accordingly, to generate user notifications according to the user's alert configuration information, the one or more user interface element(s) 1120 include at least one output user interface element, such as, for example, a display element (e.g., a light-emitting diode or the like), a display device (e.g., a liquid crystal display or the like), a speaker or another audio output device, a haptic feedback device, or the like. In a similar manner as described above, the user's alert configuration information obtained via a user interface element 1120 may be stored or otherwise maintained in the memory 1106 for future reference during operation of the pump control system 1100. In practice, one or more of the user interface element(s) 1120 may be integrated with the infusion device 502, or alternatively, be integrated in another component of an infusion system (e.g., the CCD 106, the computer 108, or the like) that is communicatively coupled to the infusion device 502 and/or the pump control system 520, 1100 as described above in the context of FIG. 1 (e.g., to support text messages, e-mails, or other remote user notifications).

In one or more exemplary embodiments, the monitoring application 1116 calculates or otherwise determines one or more thresholds used to control operation of the infusion device 502 based on the SPT value input by the user. The monitoring application 1116 may calculate or otherwise determine a predictive suspend threshold value by adding an offset value to the SPT value. In one embodiment, the offset value is fixed at an empirically determined value that achieves the desired tradeoff between the rate or frequency at which delivery is likely to be suspended and the rate or frequency at which the SPT value is likely to be violated. In this regard, increasing the offset value is likely to increase the suspend frequency and reduce the likelihood of the SPT value being violated, while decreasing the offset value is likely to decrease the suspend frequency and increase the likelihood of the SPT value being violated. For example, in one embodiment, the monitoring application 1116 adds an offset of 20 mg/dL to the SPT value to obtain the predictive suspend threshold value. In alternative embodiments, the predictive suspend threshold value may be calculated by multiplying the SPT value by a conversion factor. In exemplary embodiments, the predictive suspend threshold value is greater than or equal to the SPT value.

In a similar manner, the monitoring application 1116 calculates or otherwise determines a suspend enable threshold (SET) value having a value that is greater than the predictive suspend threshold value based on the SPT value and/or the predictive suspend threshold value. In one embodiment, the monitoring application 1116 adds an additional offset of 50 mg/dL to the SPT value in addition to the 20 mg/dL offset to obtain the SET value. In this regard, the additional offset is chosen to prevent delivery from being suspended prematurely while the user's current glucose is relatively high. Alternatively, the SET value may be calculated by multiplying the SPT value by another conversion factor. In some embodiments, the predictive suspend threshold value and the SET value calculated by the monitoring application 1116 may also be stored in the memory 1106 (e.g., in dedicated registers). Thus, it will be appreciated that in some alternative embodiments, the predictive suspend threshold value and the SET value may be user-configurable, in a similar manner as described above in the context of the SPT value. In alternative embodiments, the offset values or conversion factors used to calculate the predictive suspend threshold value and the SET value are stored in the memory 1106 and used to calculate the predictive suspend threshold value and the SET value at run time. In such embodiments, the offset values or conversion factors may be user-configurable.

As described in greater detail below in the context of FIG. 12, the current glucose measurement value is below the SET value before the suspend delivery mode is entered. When the current glucose measurement value is less than the SET value, the predicted blood glucose value is less than the predictive suspend threshold value, and predictive delivery suspension is enabled by the user, the monitoring application 1116 automatically signals, commands, or otherwise instructs the command generation application 1114 to enter or otherwise implement a suspend delivery mode during which insulin delivery is disabled. Alternatively, when the current glucose measurement value is less than both the SET value and the SPT value, the monitoring application 1116 automatically signals, commands, or otherwise instructs the command generation application 1114 to enter or otherwise implement the suspend delivery mode as long as automatic delivery suspension is enabled, regardless of whether predictive delivery suspension is enabled.

Still referring to FIG. 11, the monitoring application 1116 also calculates or otherwise determines one or more thresholds used to resume delivery of infusion based on the SPT value. The monitoring application 1116 may calculate or otherwise determine a resume enable threshold (RET) value by adding an offset value to the SPT value. In one exemplary embodiment, the offset value for determining the RET value is fixed and equal to the same offset value (e.g., 20 mg/dL) that is added to the SPT value to obtain the predictive suspend threshold value; however, in other embodiments, the offset value for determining the RET value may be greater than or less than the offset value that is added to the SPT value to obtain the predictive suspend threshold value. In this regard, the RET value is greater than the SPT value by at least an amount that makes it unlikely that the current glucose measurement value will reach the SPT value after delivery is re-enabled but before delivery can be re-suspended. Additionally, the monitoring application 1116 calculates or otherwise determines a predictive resume threshold value based on the SPT value and/or the RET value. In this regard, the predictive resume threshold value is greater than the RET value to ensure that the predicted blood glucose value is sufficiently above the SPT value and the RET value (e.g., on an upward trend) so that there is unlikely to be a need for the infusion device 502 to revert to the suspend delivery mode until at least a refractory period has elapsed after resuming delivery. For example, the monitoring application 1116 may add an additional offset of 20 mg/dL to the RET value (or alternatively, add 40 mg/dL to the SPT value). In a similar manner as described above, the RET value and the predictive resume threshold value calculated by the monitoring application 1116 may be stored in the memory 1106, or alternatively, the offset values or conversion factors used to calculate the RET value and the predictive resume threshold value may be stored in memory 1106 for calculation at run time. Likewise, in some embodiments, the RET value and the predictive resume threshold value (or alternatively, the offset values or conversion factors used to calculate them) may be user-configurable.

As described in greater detail below in the context of FIG. 13, in one or more embodiments, the suspend delivery mode is exited when the current glucose measurement value is greater than the RET value and the predicted glucose value is greater than the predictive resume threshold value. When the current glucose measurement value and the predicted blood glucose value are greater than the RET value and the predictive resume threshold value, respectively, the monitoring application 1116 automatically signals, commands, or otherwise instructs the command generation application 1114 to exit the suspend delivery mode and enter or otherwise implement another operating mode during which insulin delivery is enabled. For example, the command generation application 1114 may resume generating delivery (or dosage) commands to provide a basal infusion rate in an open-loop delivery control mode, or alternatively, by implementing a closed-loop control scheme configured to regulate the user's current glucose measurement value to a particular target blood glucose value by minimizing the difference between the current glucose measurement value and the target blood glucose value, as described in greater detail below in the context of FIG. 22.

Still referring to FIG. 11, in exemplary embodiments, the monitoring application 1116 is configured to implement one or more timers to ensure that the infusion device does not toggle between operating modes. In one embodiment, a minimum suspension time period is imposed, such that the monitoring application 1116 does not signal the command generation application 1114 to transition from the suspend delivery mode to another delivery mode until implementing the suspend delivery mode for at least the minimum suspension time period. In this regard, the suspend delivery mode may be maintained if the minimum suspension time period has not elapsed even if the current glucose measurement value is greater than the RET value and the predicted blood glucose value is greater than the predictive resume threshold value. In exemplary embodiments, the minimum suspension time period is fixed at thirty minutes, however, in alternative embodiments, the minimum suspension time period may be user-configurable. Additionally, a maximum suspension time period may be imposed, such that suspend delivery mode is not implemented indefinitely. In this regard, the infusion device may be transitioned to a normal delivery mode if the maximum suspension time period has elapsed even if the current glucose measurement value is less than the RET value and the predicted blood glucose value is less than the predictive resume threshold value. In exemplary embodiments, the maximum suspension time period is fixed at two hours, however, in alternative embodiments, the maximum suspension time period may be user-configurable.

In exemplary embodiments, a minimum delivery time period is also imposed to provide a minimum refractory period before the infusion device 502 can revert back to the suspend delivery mode. In this regard, the normal delivery mode may be maintained if the minimum delivery time period has not elapsed even if the current glucose measurement value is less than the SET value and the predicted blood glucose value is less than the predictive suspend threshold value. In exemplary embodiments, the minimum delivery time period is also fixed at thirty minutes, however, in alternative embodiments, the minimum delivery time period may be user-configurable. As described in greater detail below in the context of FIGS. 12-13, in exemplary embodiments, the refractory period implemented by the monitoring application 1116 is dynamically determined based on the responsiveness of the user. In this regard, after transitioning from the suspend delivery mode after the maximum suspension time period has elapsed, the monitoring application 1116 may generate or otherwise provide a notification to the user via a user interface element 1120 that identifies or otherwise indicates that the delivery was suspended for the maximum suspension time period. If the user is not responsive to the notification and an acknowledgment input has not been received via the user interface element(s) 1120, a maximum refractory time period may be imposed before the infusion device 502 is allowed to revert back to the suspend delivery mode. Conversely, if a user acknowledgment response is received via a user interface element 1120, the refractory time period is set to be equal to the minimum delivery time period.

Figure 12:
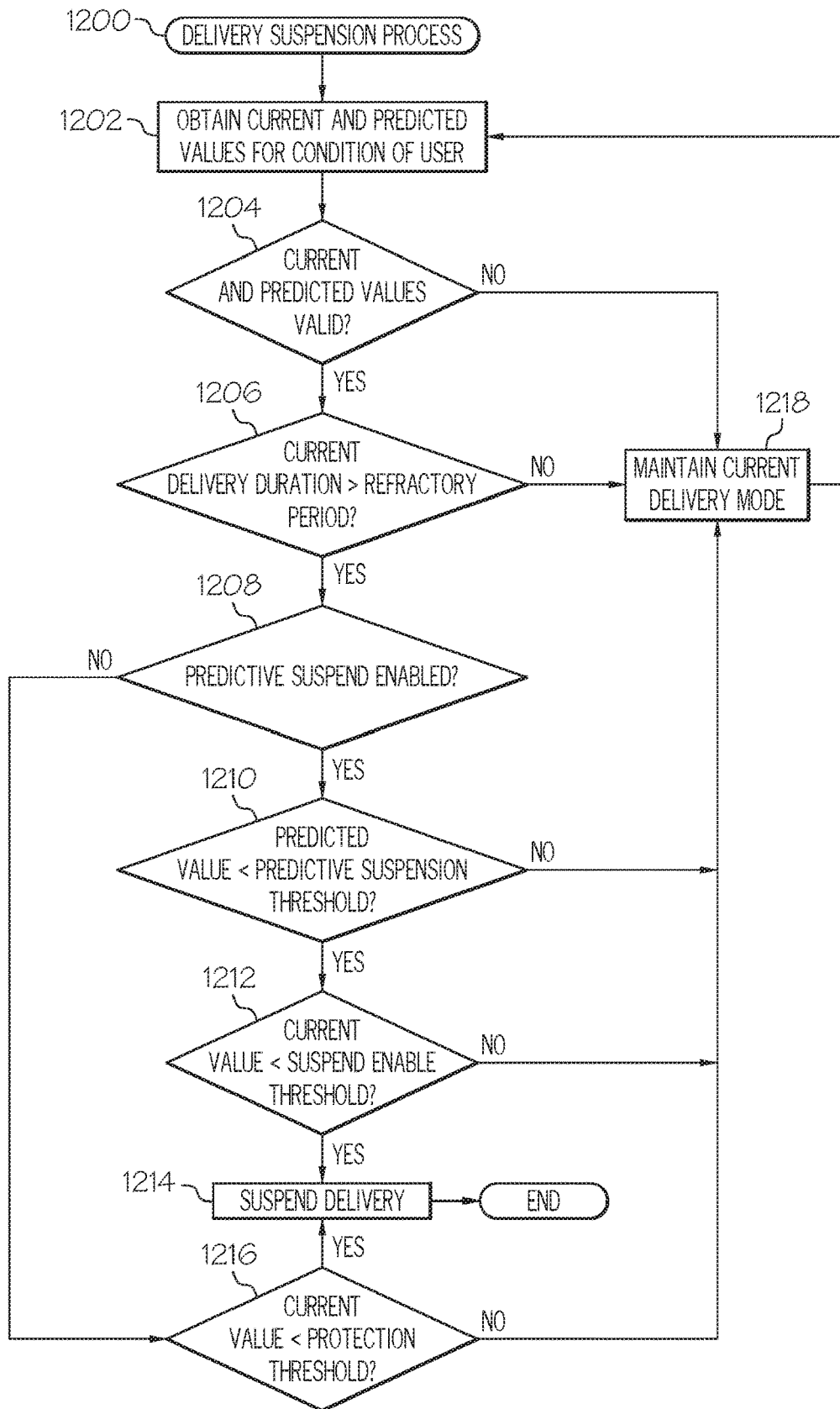
FIG. 12 depicts a flow diagram of an exemplary delivery suspension process suitable for use with the control system of FIG. 11.

FIG. 12 depicts an exemplary delivery suspension process 1200 suitable for implementation by a control system associated with a fluid infusion device, such as the pump control system 520, 1100 in the infusion device 502, to automatically suspend fluid delivery based on current and predicted values for a physiological condition of a user (or patient). The various tasks performed in connection with the delivery suspension process 1200 may be performed by hardware, firmware, software executed by processing circuitry, or any combination thereof. For illustrative purposes, the following description may refer to elements mentioned above in connection with FIGS. 1-7 and 11. In practice, portions of the delivery suspension process 1200 may be performed by different elements of the control system 500, such as, for example, the infusion device 502, the sensing arrangement 504, the pump control system 520, 1100, the pump control module 1102, the motor control module 512, and/or the motor 507. It should be appreciated that the delivery suspension process 1200 may include any number of additional or alternative tasks, the tasks need not be performed in the illustrated order and/or the tasks may be performed concurrently, and/or the delivery suspension process 1200 may be incorporated into a more comprehensive procedure or process having additional functionality not described in detail herein. Moreover, one or more of the tasks shown and described in the context of FIG. 12 could be omitted from a practical embodiment of the delivery suspension process 1200 as long as the intended overall functionality remains intact.

In exemplary embodiments, the delivery suspension process 1200 is performed when automatic delivery suspension is enabled (e.g., after the user has manipulated the user interface 1120 to enable automatic delivery suspension) and the infusion device is not currently being operated in a mode where delivery is suspended. As illustrated in FIG. 12, the delivery suspension process 1200 may repeat indefinitely while automatic delivery suspension is enabled until identifying or otherwise determining that operation of the infusion device should be suspended.

In the illustrated embodiment, the delivery suspension process 1200 begins by receiving or otherwise obtaining current and predicted values for the physiological condition of the user being monitored and identifying or otherwise determining whether those values are valid (tasks 1202, 1204). In this regard, the monitoring application 1116 receives or otherwise obtains the current glucose measurement for the user obtained by the sensing arrangement 504, 600 and/or sensing element 604 along with a predicted blood glucose value for the user at some point in the future from the data prediction application 612 and/or prediction application 712. The monitoring application 1116 verifies or otherwise confirms that neither the current glucose measurement value nor the predicted blood glucose value are flagged or otherwise marked as being invalid or unusable.

In response to identifying that the current glucose measurement value and/or the predicted blood glucose value are invalid or unusable, the delivery suspension process 1200 continues by maintaining operation of the infusion device in the current delivery mode (task 1218). If the current delivery mode is an open-loop basal delivery mode, the command generation application 1114 continues generating delivery (or dosage) commands configured to maintain a particular basal infusion rate for the user. In other embodiments, if the current delivery mode is a PID closed-loop delivery mode, the command generation application 1114 continues generating delivery commands using the current glucose measurement value and/or the predicted blood glucose value. For example, if the current glucose measurement value is valid and usable, the command generation application 1114 may calculate or otherwise determine a difference between the current glucose measurement value and a target blood glucose reference value (or glucose setpoint) and apply proportional-integral-derivative (PID) control parameters to the difference to arrive at a delivery command configured to regulate the current glucose measurement value to the target blood glucose reference value, as described in greater detail below in the context of FIG. 22. Conversely, if the current glucose measurement value is invalid or unusable, the command generation application 1114 may determine a delivery command based on the user's current insulin on board without relying on the current glucose measurement from the sensing arrangement 504, as described in greater detail below in the context of FIG. 21. Alternatively, if the current glucose measurement value is invalid or unusable, the command generation application 1114 may identify a default delivery command configured to maintain a particular infusion rate until a subsequently received current glucose measurement value is valid and usable. As described above, the delivery command generated by the command generation application 1114 is provided to the motor control module 512, which, in turn, operates the motor 507 to displace the plunger 517 and infuse or otherwise deliver insulin to the body 501 of the user.

When the current glucose measurement value and the predicted blood glucose value are both valid and usable, the delivery suspension process 1200 continues by identifying or otherwise determining whether the duration for which the infusion device has been operated in the delivery mode is greater than a refractory time period (task 1206). When the infusion device has been operated in the current delivery mode for less than the refractory time period, the delivery suspension process 1200 continues by maintaining operation of the infusion device in the current delivery mode (task 1218). As described above, the monitoring application 1116 implements or otherwise provides a timer that tracks or otherwise monitors the duration of time for which the command generation application 1114 implements a delivery mode to impose a refractory time period before the command generation application 1114 can revert back to implementing a suspend delivery mode, thereby providing a recovery period after transitioning from the suspend delivery mode to a delivery mode. In exemplary embodiments, the refractory period imposed by the monitoring application 1116 is dynamically determined based on the responsiveness of the user. In this regard, if the user has been classified as responsive, the monitoring application 1116 verifies, confirms, or otherwise ensures that the command generation application 1114 has implemented the delivery mode continuously for at least the minimum delivery time period (e.g., thirty minutes) before proceeding. Alternatively, when the user is nonresponsive, the monitoring application 1116 confirms that the command generation application 1114 has implemented the delivery mode continuously for at least the maximum refractory time period (e.g., four hours) before proceeding. It should be noted that in some embodiments, in response to the automatic delivery suspension being enabled, the refractory time period may be initialized at zero because delivery has not yet been suspended.

If the refractory period currently being imposed has elapsed, the delivery suspension process 1200 continues by identifying or otherwise determining whether predictive automatic delivery suspension has been enabled by the user (task 1208). When predictive automatic delivery suspension is enabled, the delivery suspension process 1200 continues by identifying or otherwise determining whether the predicted value is less than the predictive suspend threshold value (task 1210). If the predicted value is less than the predictive suspend threshold value, the delivery suspension process 1200 continues by identifying or otherwise determining whether the current measurement value is less than the suspend enable threshold value and suspending delivery when the current measurement value is less than the suspend enable threshold value (tasks 1212, 1214). Otherwise, if the predicted value is greater than the predictive suspend threshold value or the current measurement value is greater than the suspend enable threshold value, the delivery suspension process 1200 maintains delivery in a similar manner as described above (task 1218).

When predictive automatic delivery suspension is enabled, the monitoring application 1116 determines whether the user's predicted blood glucose value is less than the predictive suspend threshold value determined based on the SPT value set by the user. When the user's predicted blood glucose value is less than the predictive suspend threshold value, the monitoring application 1116 confirms that the current blood glucose measurement for the user is also less than the SET value. When the user's predicted blood glucose value is less than the predictive suspend threshold value and the current blood glucose measurement is also less than the SET value, the monitoring application 1116 automatically signals, commands, or otherwise instructs the command generation application 1114 to implement a suspend delivery mode where any nonzero delivery commands are disabled, deactivated, or otherwise prevented from being implemented by the motor control module 512. For example, the monitoring application 1116 may signal the command generation application 1114 to disable a delivery command generated using the PID control parameters and provide a delivery command of zero to the motor control module 512, thereby preventing further displacement of the plunger 517 and suspending delivery of insulin to the body 501 of the user. In other embodiments, the monitoring application 1116 may cause the pump control module 1102 to output a flag signal that indicates, to the motor control module 512, that any delivery commands output by the command generation application 1114 should be ignored or otherwise disregarded. Additionally, depending on the embodiment, the monitoring application 1116 may interact with an output user interface 1120 to generate or otherwise provide an auditory and/or visual notification that indicates, to the user, that insulin delivery is being suspended. The user notifications may be generated in accordance with user-specific and/or user-configurable alert configuration information, in a similar manner as described in U.S. patent application Ser. No. 14/174,487, which is incorporated by reference herein. In other embodiments, the configuration settings for user notifications when automatic delivery suspension is enabled may be fixed and maintained in memory 1106 in a manner that does not allow the user to modify the notification settings.

In alternative embodiments, if predictive automatic delivery suspension is disabled by the user but automatic suspension based on the suspend protection threshold is enabled, the delivery suspension process 1200 continues by identifying or otherwise determining whether the current measurement value is less than the suspend protection threshold value and suspending delivery when the current measurement value is less than the protection threshold value (tasks 1214, 1216). In this regard, the monitoring application 1116 determines whether the current glucose measurement value is less than the SPT value set by the user. When the user's current glucose measurement value is less than the SPT, the monitoring application 1116 automatically signals, commands, or otherwise instructs the command generation application 1114 and/or the motor control module 512 to implement a suspend delivery mode in a similar manner as described above, thereby preventing further displacement of the plunger 517 and suspending infusion of insulin to the body 501 of the user.

Figure 13:
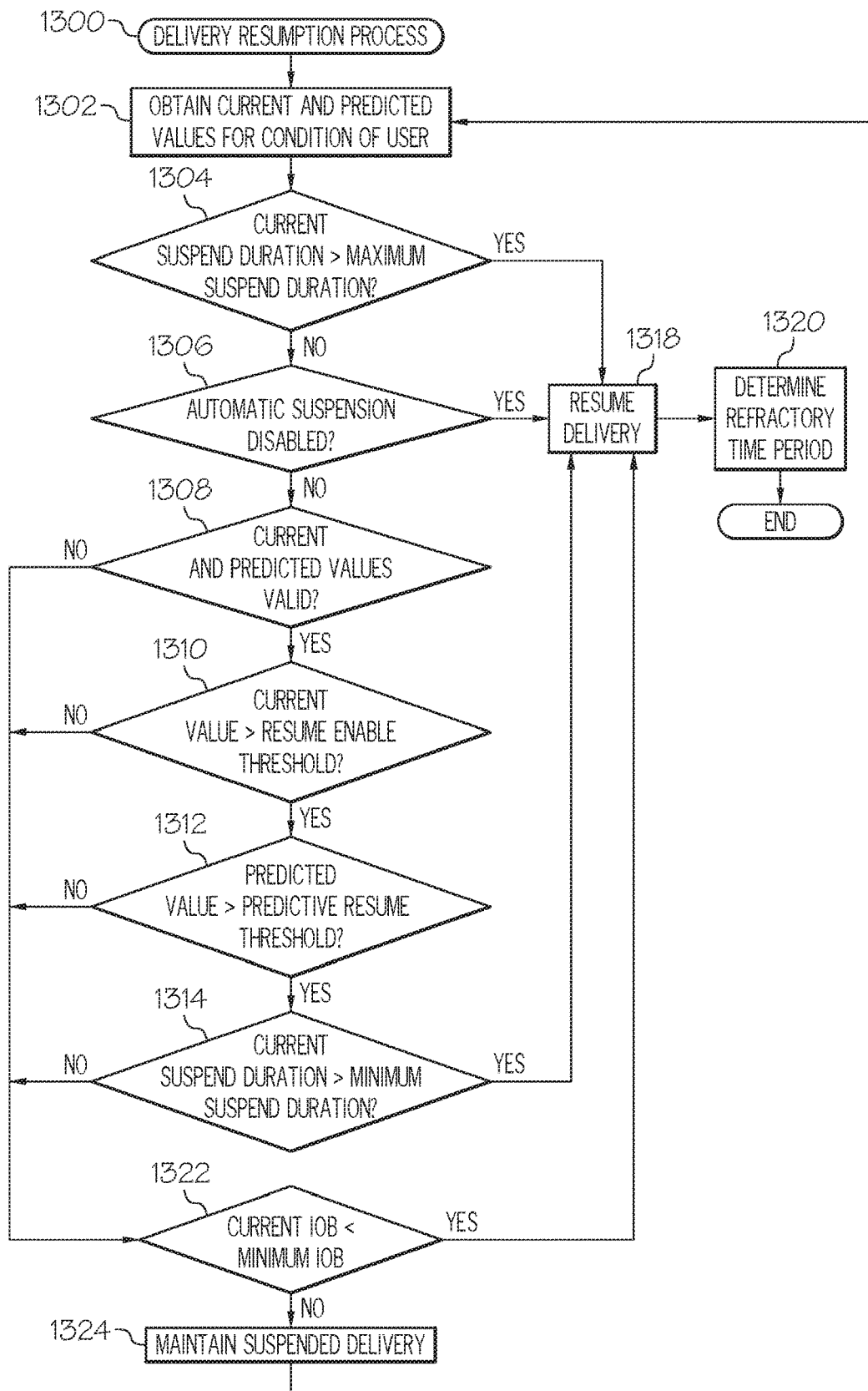
FIG. 13 depicts a flow diagram of an exemplary delivery resumption process suitable for use with the control system of FIG. 11 in conjunction with the delivery suspension process of FIG. 12.

FIG. 13 depicts an exemplary delivery resumption process 1300 suitable for implementation by a control system associated with a fluid infusion device, such as the pump control system 520, 1100 in the infusion device 502, in conjunction with the delivery suspension process 1200 of FIG. 12 to automatically resume fluid delivery based on current and predicted values for the physiological condition of the user (or patient). The various tasks performed in connection with the delivery resumption process 1300 may be performed by hardware, firmware, software executed by processing circuitry, or any combination thereof. For illustrative purposes, the following description may refer to elements mentioned above in connection with FIGS. 1-7 and 11. In practice, portions of the delivery resumption process 1300 may be performed by different elements of the control system 500, such as, for example, the infusion device 502, the sensing arrangement 504, the pump control system 520, 1100, the pump control module 1102, the motor control module 512, and/or the motor 507. It should be appreciated that the delivery resumption process 1300 may include any number of additional or alternative tasks, the tasks need not be performed in the illustrated order and/or the tasks may be performed concurrently, and/or the delivery resumption process 1300 may be incorporated into a more comprehensive procedure or process having additional functionality not described in detail herein. Moreover, one or more of the tasks shown and described in the context of FIG. 13 could be omitted from a practical embodiment of the delivery resumption process 1300 as long as the intended overall functionality remains intact.

In exemplary embodiments, the delivery resumption process 1300 is performed after the infusion device has automatically entered an operating mode where delivery is suspended or otherwise disabled (e.g., suspend delivery mode at task 1214) as a result of the delivery suspension process 1200 to prevent fluid infusion to a user. As illustrated in FIG. 13, the delivery resumption process 1300 may repeat indefinitely while delivery is suspended until identifying or otherwise determining that operation of the infusion device to deliver fluid should be resumed.

In the illustrated embodiment, the delivery resumption process 1300 begins by receiving or otherwise obtaining current and predicted values for the physiological condition of the user being monitored, identifying or otherwise determining whether the duration for which the infusion device has been operated in the suspend delivery mode is greater than a maximum suspension time period, and automatically resuming delivery of fluid using the current value for the physiological condition of the user when the current suspend duration is greater than the maximum suspension time period (tasks 1302, 1304, 1318). In this regard, after determining to suspend delivery, the monitoring application 1116 initializes a timer to monitor the duration of time for which the suspended delivery mode is implemented. When the current suspend duration is greater than the maximum suspension time period (e.g., two hours), the monitoring application 1116 automatically transitions the infusion device from the suspend delivery mode to another delivery mode. For example, the monitoring application 1116 may automatically signal, command, or otherwise instruct the command generation application 1114 to resume generating delivery commands and providing the delivery commands to the motor control module 512. Alternatively, the monitoring application 1116 may cause the pump control module 1102 to de-assert or otherwise remove a suspend delivery flag signal to indicate, to the motor control module 512, that delivery commands output by the command generation application 1114 should now be implemented or otherwise utilized to operate the motor 507. Additionally, depending on the embodiment, the monitoring application 1116 may interact with an output user interface 1120 to generate or otherwise provide an auditory and/or visual notification that indicates, to the user, that the maximum suspension time period has been met or exceeded and the suspend delivery mode has been automatically terminated.

When the maximum suspension time period has not elapsed since entering the suspend delivery mode, the delivery resumption process 1300 continues by identifying or otherwise determining whether the automatic delivery suspension has been disabled by the user and resuming delivery of fluid using the current value for the physiological condition of the user in response to detecting that automatic delivery suspension is disabled (tasks 1306, 1318). In this regard, if the user manipulates the user interface element 1120 to disable the automatic delivery suspension (e.g., delivery suspension process 1200), the monitoring application 1116 automatically signals, commands, or otherwise instructs the command generation application 1114 and/or the motor control module 512 to terminate the suspend delivery mode and begin implementing another operating mode where delivery is enabled.

When automatic delivery suspension remains enabled, the delivery resumption process 1300 continues by identifying or otherwise determining whether the current and predicted values for the physiological condition of the user are valid before identifying or otherwise determining whether the current value for the physiological condition is greater than a resume enable threshold (tasks 1308, 1310). When the current value for the physiological condition is greater than the resume enable threshold, the delivery resumption process 1300 continues by identifying or otherwise determining whether the predicted value for the physiological condition is greater than a predictive resume threshold (task 1312). When the predicted value is also greater than its corresponding resume threshold, the delivery resumption process 1300 verifies or otherwise confirms that the duration for which the infusion device has been operated in the suspend delivery mode is greater than a minimum suspension time period before resuming delivery (tasks 1314, 1318).

After the monitoring application 1116 verifies or otherwise confirms that neither the current glucose measurement value nor the predicted blood glucose value are flagged or otherwise marked as being invalid or unusable, the monitoring application 1116 compares the current glucose measurement value to the RET value. After the monitoring application 1116 determines the current glucose measurement value is greater than the RET value, the monitoring application 1116 determines whether the predicted blood glucose value is greater than the predictive resume threshold value. After identifying that both current glucose measurement value is greater than the RET value and the predicted blood glucose value is greater than the predictive resume threshold value, the monitoring application 1116 confirms that the current suspend duration is greater than the minimum suspension time period (e.g., thirty minutes). When the minimum suspension time period has elapsed, the monitoring application 1116 automatically transitions the infusion device from the suspend delivery mode to another delivery mode, such as a closed-loop delivery mode, for example, by signaling the command generation application 1114 and/or the motor control module 512 to resume implementing the normal closed-loop delivery mode.

In exemplary embodiments, when the delivery resumption process 1300 determines delivery should be resumed, the delivery resumption process 1300 also identifies or otherwise determines a suspension refractory time period for which the infusion device should be maintained in a delivery mode before the delivery suspension process 1200 can automatically transition the infusion device back to a suspended delivery mode (task 1320). In one or more embodiments, the monitoring application 1116 determines the refractory time period is equal to a maximum refractory time period (e.g., four hours) after determining that the current suspend duration is greater than or equal to the maximum suspend duration and the monitoring application 1116 has not identified, received, or otherwise detected user input via the user interface element(s) 1120. In this regard, absent the user manipulating an input user interface element 1120 to respond to a user notification generated by the monitoring application 1116 that indicates the maximum suspension time period has been met or exceeded, the monitoring application 1116 classifies the user as nonresponsive and imposes the maximum refractory time period until a user response is detected. Otherwise, when the user is responsive (e.g., by manually resuming delivery, disabling the automatic delivery suspension, responding to user notifications, or the like) or the monitoring application 1116 determines delivery should be resumed based on the user's glucose values (e.g., at tasks 1310, 1312 and 1314), the monitoring application 1116 sets the refractory time period to be equal to a minimum delivery time period (e.g., thirty minutes). Thereafter, the delivery suspension process 1200 imposes the refractory period determined by the delivery resumption process 1300 (e.g., at task 1206) before transitioning the infusion device back to a suspend delivery mode.

Still referring to FIG. 13, in exemplary embodiments, the delivery resumption process 1300 maintains the infusion device in the suspend delivery mode (task 1324) when one of the values for the physiological condition of the user is invalid, the current value for the physiological condition is less than the resume enable threshold, the predicted value for the physiological condition is less than the predictive resume threshold, and/or the duration of suspend delivery mode is less than the minimum suspension time period. In the illustrated embodiment, however, the delivery resumption process 1300 verifies or otherwise confirms the amount of infused fluid that is currently active in the body of the user is greater than a minimum threshold amount of active fluid in the user's body prior to maintaining suspended delivery (task 1322). In this regard, as described in greater detail below in the context of FIGS. 20-21, the delivery resumption process 1300 may be integrated with or otherwise implemented in conjunction with an IOB monitoring process 2000, whereby the delivery resumption process 1300 also confirms or otherwise verifies that the current IOB in the body of the user is greater than a minimum IOB for the user before maintaining the infusion device in the suspend delivery mode. In response to determining the current IOB for the user is less than the minimum JOB, the delivery resumption process 1300 determines to resume delivery and automatically transitions the infusion device from the suspended delivery mode to a delivery mode that is augmented or otherwise adjusted to regulate the user's IOB (task 1318). In such embodiments, rather than regulating the physiological condition of the user influenced by the infused fluid (e.g., the user's blood glucose level), the infusion device is operated to regulate the active amount of infused fluid in the user's body. For example, in response to determining to resume delivery based on the current IOB for the user being less than the minimum JOB, the monitoring application 1116 may signal, command, or otherwise instruct the command generation application 1114 to implement or otherwise support the IOB control process 2100 of FIG. 21, as described in greater detail below. In such embodiments, the delivery suspension process 1200 may impose a refractory period determined by the delivery resumption process 1300 (e.g., at task 1206) before transitioning the infusion device from the IOB delivery control mode back to a suspend delivery mode. In one embodiment, the maximum refractory time period (e.g., four hours) is imposed before transitioning the infusion device from the IOB delivery control mode back to a suspend delivery mode.

FIGS. 14-19 are graphs depicting the relationship between the current glucose measurement values for the user with respect to time for various embodiments of the delivery suspension process 1200 of FIG. 12 in conjunction with the delivery resumption process 1300 of FIG. 13 when automatic delivery suspension is enabled using a SPT value of 70 mg/dL. In some embodiments, the graphs may be presented on a display associated with any device of an infusion system, such as, for example, on a display element 226, 1120 of an infusion device 102, 200, 502 or a display associated with another device 106, 108 in the infusion system 100. It should be appreciated that FIGS. 14-19 are provided primarily to aid in understanding of the subject matter described herein and are not intended to be limiting. In this regard, numerous different combinations and/or scenarios of glucose values, user notifications, and user responses are likely to occur in practical embodiments of the subject matter described herein.

Figure 14:
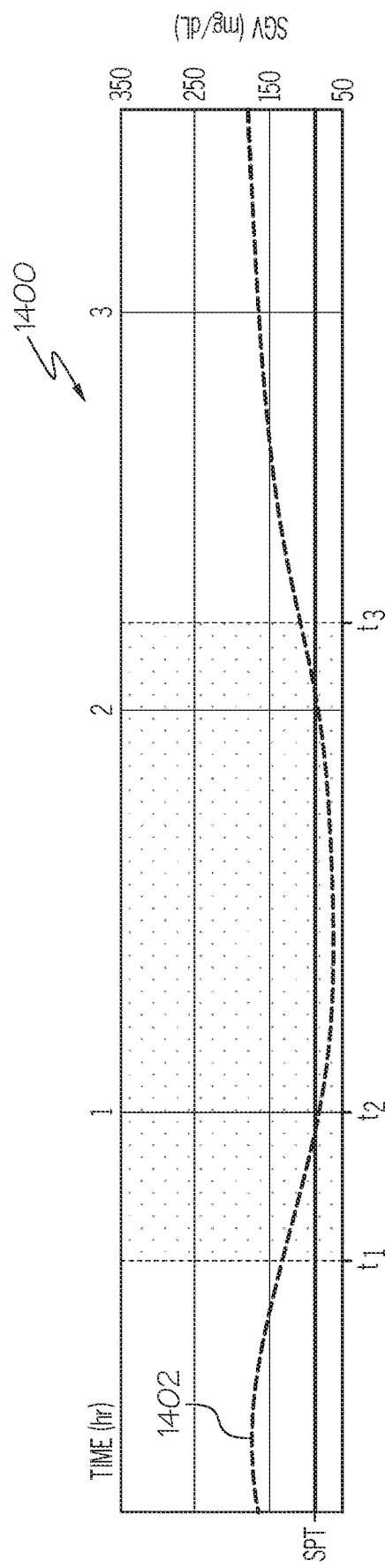
FIGS. 14-19 are graphs depicting exemplary relationships between a user's current measurement values with respect to time for various exemplary embodiments of the delivery suspension process of FIG. 12 in conjunction with the delivery resumption process of FIG. 13.

Turning to the graph 1400 in FIG. 14, at a first time $t_1$, the monitoring application 1116 automatically signals, commands, or otherwise instructs the command generation application 1114 and/or the motor control module 512 to operate in a suspend delivery mode when the user's predicted blood glucose value is less than the predictive suspend threshold value (e.g., 20 mg/dL plus the SPT value) and the current glucose measurement value 1402 is less than the SET value of 140 mg/dL (e.g., a 50 mg/dL offset added to the predictive suspend threshold value). Additionally, the monitoring application 1116 may interact with the user interface element(s) 1120 to generate or otherwise provide a notification to the user that the infusion device 502 has automatically entered the suspend delivery mode at time $t_1$.

At time $t_2$, the monitoring application 1116 automatically operates the user interface element(s) 1120 to generate or otherwise provide one or more low glucose notifications when current glucose measurement value 1402 is less than or equal to the SPT value of 70 mg/dL. In this regard, if the user does not acknowledge or otherwise respond to the low glucose notifications, the monitoring application 1116 may progressively escalate the low glucose notifications (e.g., by progressively increasing the volume, frequency, vibration magnitude, brightness, visibility, or the like) until receiving a response from the user and/or until the current glucose measurement value 1402 rises above the SPT value.

In the illustrated embodiment, at time $t_3$, the monitoring application 1116 automatically signals, commands, or otherwise instructs the command generation application 1114 and/or the motor control module 512 to resume operating in a delivery mode when the user's predicted blood glucose value is greater than the predictive resume threshold value of 110 mg/dL (e.g., an offset of 20 mg/dL added to the RET value and/or an offset of 40 mg/dL added to the SPT value) and the current glucose measurement value 1402 is greater than the RET value of 90 mg/dL (e.g., an offset of 20 mg/dL added to the SPT value). In one or more embodiments, because the determination to resume delivery is based on an increase in the user's current and/or predicted glucose values, the monitoring application 1116 automatically sets the refractory period to the minimum delivery time period of thirty minutes. Additionally, the monitoring application 1116 may interact with the user interface element(s) 1120 to generate or otherwise provide a notification to the user that the infusion device 502 has automatically resumed operating in a delivery mode at time $t_3$.

Figure 15:
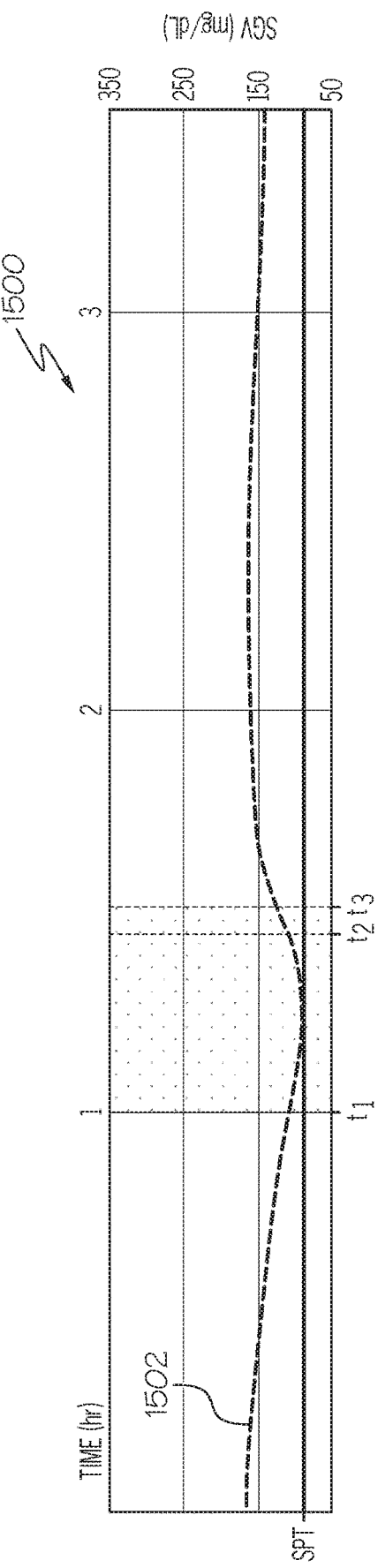

Turning now to the graph 1500 of FIG. 15, in a similar manner as described above in the context of FIG. 14, at a first time $t_1$, the monitoring application 1116 automatically signals, commands, or otherwise instructs the command generation application 1114 and/or the motor control module 512 to operate in a suspend delivery mode when both the user's predicted glucose value is less than the predictive suspend threshold value and the user's current glucose measurement value 1502 is less than the SET value. At time $t_2$, the monitoring application 1116 identifies or otherwise determines that both the user's predicted blood glucose value is greater than the predictive resume threshold value and the current glucose measurement value 1502 is greater than the RET value of 90 mg/dL, however, the monitoring application 1116 maintains operation of the infusion device 502 in the suspend delivery mode because the minimum suspension time period has not elapsed since time $t_1$. At time $t_3$, after a minimum suspension time period of thirty minutes has elapsed since time $t_1$, the monitoring application 1116 automatically signals, commands, or otherwise instructs the command generation application 1114 and/or the motor control module 512 to resume operating in a delivery mode and sets the refractory period to the minimum delivery time period when both the user's predicted glucose value is greater than the predictive resume threshold value and the current glucose measurement value 1502 is greater than the RET value.

Figure 16:
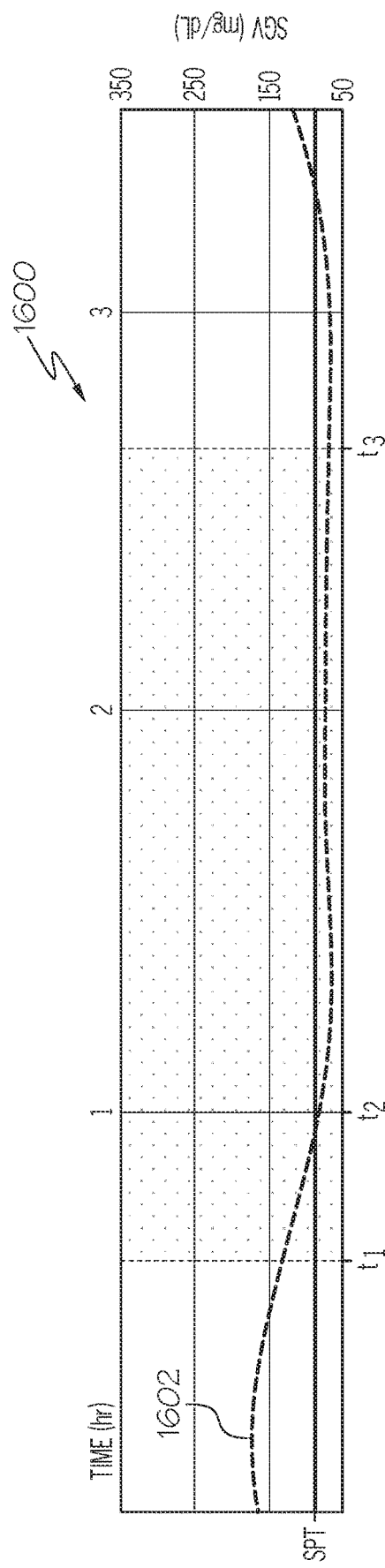

In the graph 1600 of FIG. 16, in a similar manner as described above in the context of FIG. 14, the monitoring application 1116 automatically signals, commands, or otherwise instructs the command generation application 1114 and/or the motor control module 512 to operate in a suspend delivery mode when both the user's predicted blood glucose value is less than the predictive suspend threshold value and the user's current glucose measurement value 1602 is less than the SET value at time $t_1$, and the monitoring application 1116 automatically operates the output user interface element(s) 1120 to generate or otherwise provide one or more low glucose notifications when the current glucose measurement value 1602 is less than or equal to the SPT value at time $t_2$.

At time $t_3$, the monitoring application 1116 identifies or otherwise determines that the current suspend duration is greater than or equal to the maximum suspend time period of two hours, and in response, the monitoring application 1116 automatically signals, commands, or otherwise instructs the command generation application 1114 and/or the motor control module 512 to resume operating in a delivery mode even though the user's predicted blood glucose value may be less than the predictive resume threshold value and/or the current glucose measurement value 1602 is less than the RET value. It should be noted, however, that even though the command generation application 1114 and/or the motor control module 512 may be operating in a mode where delivery is enabled, actual fluid delivery to the body of the user does not necessarily occur at all times for some delivery modes. For example, a closed-loop delivery mode may not deliver any insulin during periods when the user's current glucose measurement value being less than the target glucose value resulting in delivery commands equal to zero (e.g., because negative infusion is not possible).

In exemplary embodiments, the monitoring application 1116 interacts with the user interface element(s) 1120 to generate or otherwise provide a notification to the user that indicates the infusion device 502 has automatically resumed operating in a delivery mode at time $t_3$ based on the maximum suspend duration being met rather than an increase in the user's current and/or predicted blood glucose. In particular for the embodiment of FIG. 16 where the current glucose measurement value 1602 is below the SPT value after the maximum suspend duration has elapsed, the monitoring application 1116 may generate or otherwise provide one or more urgent notifications to increase the likelihood of the user consuming carbohydrates, recalibrating and/or replacing the sensing arrangement 504, or otherwise engaging in activities likely to remedy any potential hypoglycemic event. In one or more embodiments, the configuration settings for these urgent resume notifications are fixed and not user-configurable to ensure users are always alerted when the suspend delivery mode is automatically terminated while the user's current glucose measurement value 1602 is below the SPT value.

As described above in the context of FIGS. 12-13, in embodiments where the suspend delivery mode is terminated based on the maximum suspend time period elapsing and the monitoring application 1116 fails to receive an acknowledgment or response to the user notification, the monitoring application 1116 automatically sets the refractory period to the maximum refractory time period of four hours. Thereafter, as described in greater detail below in the context of FIGS. 18-19, the monitoring application 1116 may dynamically reduce the refractory time period (e.g., from four hours to the minimum delivery time of thirty minutes) upon receiving an acknowledgment or response to the user notification prior to four hours elapsing since time $t_3$.

Figure 17:
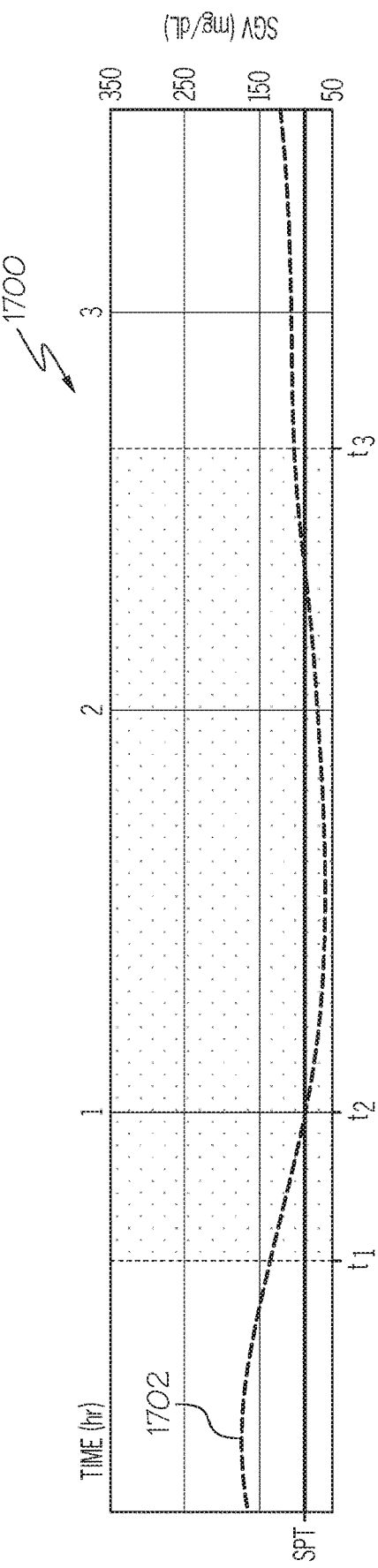

The graph 1700 of FIG. 17 is similar to the graph 1600 of FIG. 16 but depicts an embodiment where the user's current glucose measurement value 1702 is greater than the SPT value at time $t_3$. In this regard, the automatically signals, commands, or otherwise instructs the command generation application 1114 and/or the motor control module 512 to resume operating in a delivery mode based on the difference between time $t_3$ and time $t_1$ being greater than or equal to the maximum suspension time period, as described above. In the embodiment of FIG. 17, the monitoring application 1116 operates the output user interface element(s) 1120 to generate or otherwise provide a notification to the user that the infusion device 502 has automatically resumed operating in a delivery mode based on the maximum suspend duration being met. However, these user notifications may have reduced urgency associated therewith (e.g., fewer notifications, lower intensity and/or frequency of notifications, or the like) relative to the urgent resume notifications generated when the current glucose measurement value 1602 is less than the SPT value because the user's current glucose measurement value 1702 is greater than the SPT value.

Figure 18:
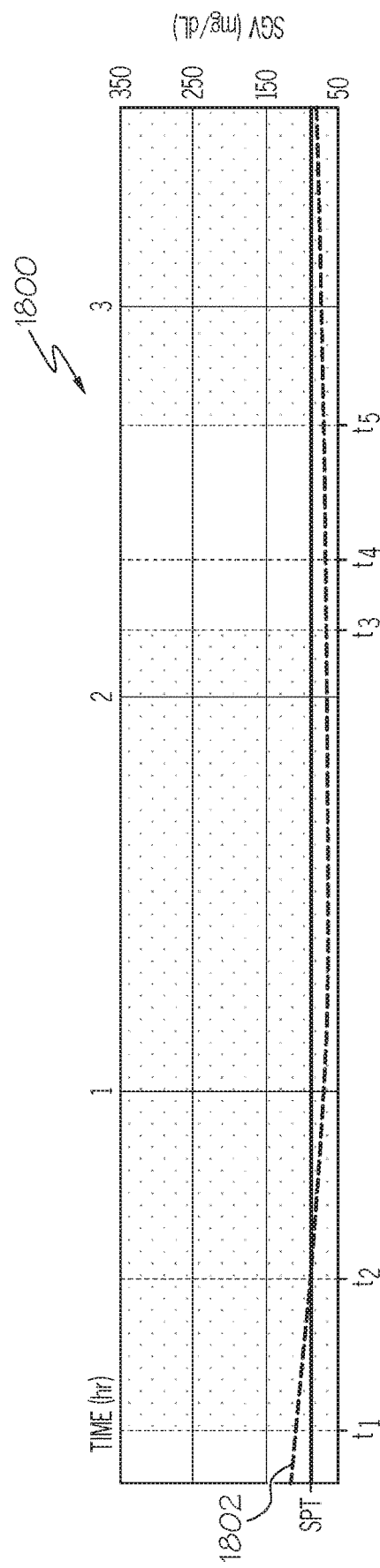

Turning now to the graph 1800 of FIG. 18, at time $t_1$, the monitoring application 1116 automatically signals the command generation application 1114 and/or the motor control module 512 to operate in a suspend delivery mode when the user's predicted glucose value is less than the predictive suspend threshold value and the user's current glucose measurement value 1802 is less than the SET value. At time $t_2$, the monitoring application 1116 automatically operates the output user interface element(s) 1120 to generate or otherwise provide one or more low glucose notifications when the current glucose measurement value 1802 is less than or equal to the SPT value. While the current glucose measurement value 1802 is less than the SPT value, the monitoring application 1116 may progressively escalate or otherwise increase the number and/or intensity of the user notifications in the absence of receiving an acknowledgment or other response from the user. At time $t_3$, once the current suspend duration reaches the maximum suspension time period of two hours, the monitoring application 1116 automatically signals the command generation application 1114 and/or the motor control module 512 to resume operating in a delivery mode. The monitoring application 1116 also sets the refractory period to the maximum refractory time period of four hours while continuing to generate low glucose user notifications or generating an urgent resume notification in addition to and/or in alternative to the low glucose notifications.

At time $t_4$, in response to receiving an acknowledgment or response to the user notifications from the user (e.g., the user clears or otherwise acknowledges the urgent resume notification), the monitoring application 1116 dynamically adjusts the refractory period from the maximum refractory time period of four hours to the minimum delivery time period of thirty minutes. Thereafter, at time $t_5$, once the minimum delivery time period has elapsed since time $t_3$, the monitoring application 1116 automatically signals the command generation application 1114 and/or the motor control module 512 to revert to the suspend delivery mode while both the user's predicted blood glucose value is less than the predictive suspend threshold value and the user's current glucose measurement value 1802 is less than the SET value.

Figure 19:
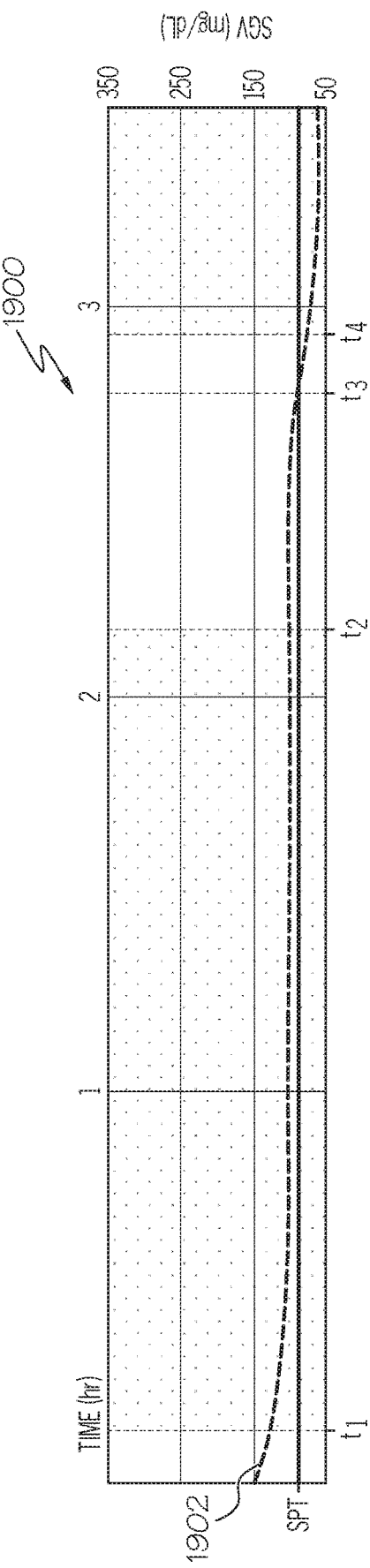

Turning to the graph 1900 of FIG. 19, at time $t_1$, the monitoring application 1116 automatically operates the infusion device 502 in a suspend delivery mode when both the user's predicted blood glucose value is less than the predictive suspend threshold value and the user's current glucose measurement value 1902 is less than the SET value. At time $t_2$, once the current suspend duration reaches the maximum suspension time period of two hours, the monitoring application 1116 automatically signals the command generation application 1114 and/or the motor control module 512 to resume operating in a delivery mode and sets the refractory period to the maximum refractory time period of four hours. At time $t_3$, when the user's current glucose measurement value 1902 is less than the SPT value while in the delivery mode and before the maximum refractory period has elapsed, the monitoring application 1116 may automatically generate or otherwise provide one or more low blood glucose user notifications via the output user interface element(s) 1120.

At time $t_4$, in response to receiving an acknowledgment or response to the low blood glucose notification, the monitoring application 1116 dynamically adjusts the refractory period from the maximum refractory time period of four hours to the minimum delivery time period of thirty minutes. Substantially immediately thereafter (e.g., on the next iteration of the delivery resumption process 1300), the monitoring application 1116 determines that the difference between time $t_4$ and time $t_2$ is greater than the minimum delivery time period (i.e., the adjusted refractory time period) and automatically signals the command generation application 1114 and/or the motor control module 512 to revert to the suspend delivery mode when both the user's predicted blood glucose value is less than the predictive suspend threshold value and the user's current glucose measurement value 1902 is less than the SET value.

Figure 20:
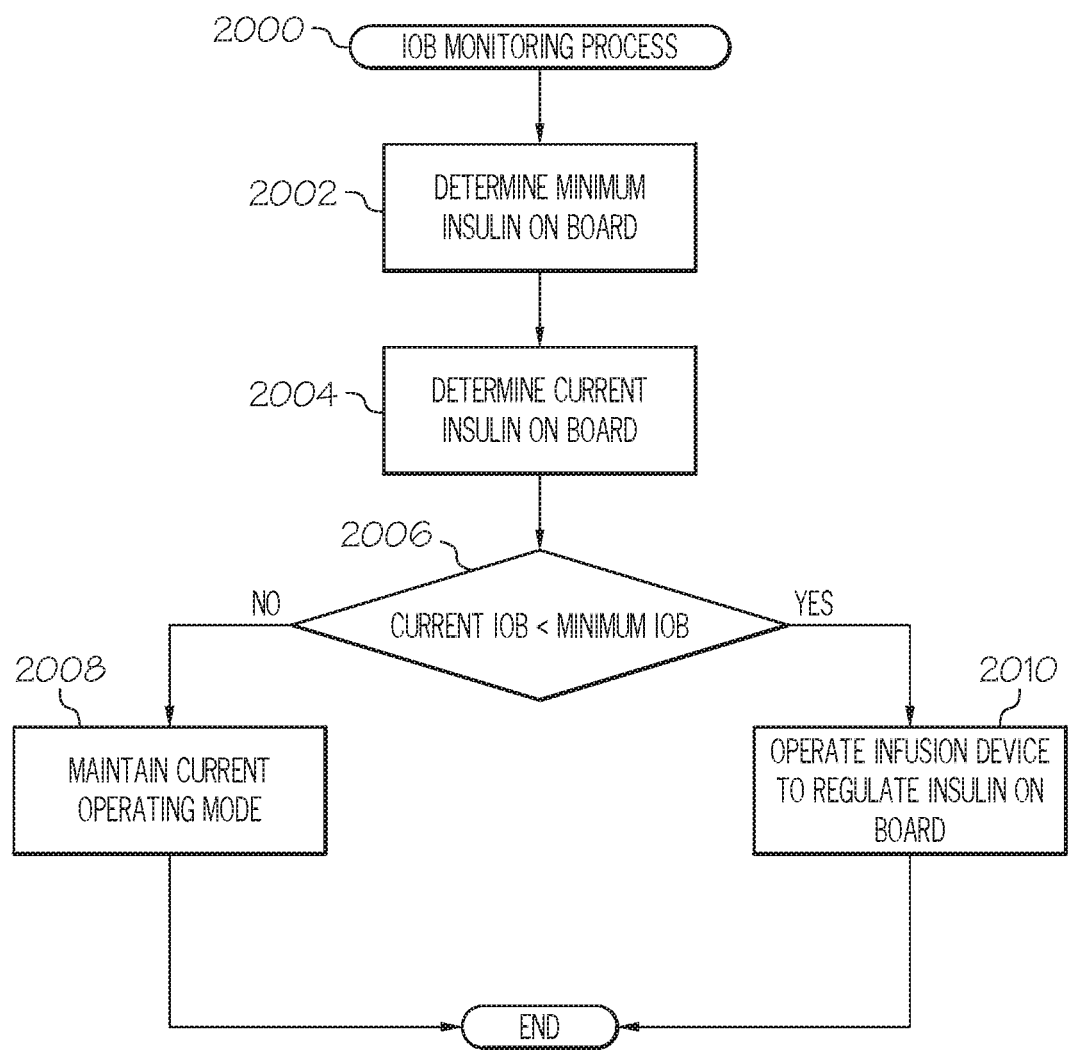
FIG. 20 depicts a flow diagram of an exemplary insulin on board monitoring process suitable for use with the control system of FIG. 11.

FIG. 20 depicts an exemplary IOB monitoring process 2000 suitable for implementation by a control system associated with a fluid infusion device, such as the pump control system 520, 1100 in the infusion device 502, to automatically operate the fluid infusion device to deliver fluid in a manner that regulates or otherwise controls the active amount of fluid (e.g., the JOB) in the body of a user (or patient). In this regard, in various situations, when the infusion rate is reduced to zero (e.g., in response to meal-related glucose fluctuations, erroneous and/or invalid glucose sensor measurement values, or the like) or suspended as described above in connection with delivery suspension process 1200, the active amount of fluid in the body of the user becomes depleted as the fluid is metabolized by the user's body. For example, when a current blood glucose measurement for the user that is fed back to the input of a closed-loop control system is below a target blood glucose reference value (or glucose setpoint), the closed-loop control system may output a delivery command of zero (since insulin cannot be removed from the user's body) until the user's current glucose measurement begins increasing towards and/or above the target value. During this time period, any remaining active insulin in the user's body is gradually being metabolized. Depending on how long the insulin delivery rate is equal to zero or infusion is otherwise suspended, the user's IOB may be relatively low (and potentially depleted completely) before insulin infusion is resumed when the user's current glucose measurement exceeds the target glucose value. The delay between when the user's IOB goes low or becomes depleted and when insulin delivery is resumed is further compounded by the delay between when insulin is infused and when the insulin is metabolized and begins to affect the user's glucose levels. As a result, the user's glucose level could be undesirably high before the infused insulin takes effect. Accordingly, to reduce the likelihood of a hyperglycemic event in response to periods of reduced and/or suspended insulin delivery, the IOB monitoring process 2000 monitors and detects when the user's current IOB falls below a desired threshold amount and initiates an IOB control process to regulate the user's IOB, as described in greater detail below in the context of FIG. 21 and FIGS. 23-24.

Still referring to FIG. 20, the various tasks performed in connection with the IOB monitoring process 2000 may be performed by hardware, firmware, software executed by processing circuitry, or any combination thereof. For illustrative purposes, the following description may refer to elements mentioned above in connection with FIGS. 1-7 and 11. In practice, portions of the IOB monitoring process 2000 may be performed by different elements of the control system 500, such as, for example, the infusion device 502, the sensing arrangement 504, the pump control system 520, 1100, the pump control module 1102, the motor control module 512, and/or the motor 507. It should be appreciated that the IOB monitoring process 2000 may include any number of additional or alternative tasks, the tasks need not be performed in the illustrated order and/or the tasks may be performed concurrently, and/or the IOB monitoring process 2000 may be incorporated into a more comprehensive procedure or process having additional functionality not described in detail herein. Moreover, one or more of the tasks shown and described in the context of FIG. 20 could be omitted from a practical embodiment of the IOB monitoring process 2000 as long as the intended overall functionality remains intact.

Depending on the embodiment, the IOB monitoring process 2000 may be implemented independently or integrated with the delivery resumption process 1300 of FIG. 13. For example, the IOB monitoring process 2000 may be performed during operation of the infusion device 502 in a normal closed-loop delivery mode to detect and respond to low IOB that results from a closed-loop control system generating delivery commands that result in a relatively low infusion rate or an infusion rate of zero over a period of time (e.g., when the user's current glucose values are below a target glucose value) when the closed-loop delivery mode is not suspended. In such embodiments, upon suspension of delivery, the IOB monitoring process 2000 may also be performed concurrently to the delivery resumption process 1300 while the infusion device 502 is operated in a suspend delivery mode, in which case task 1322 may be absent from delivery resumption process 1300. In alternative embodiments, the IOB monitoring process 2000 may be integrated into the delivery resumption process 1300 (e.g., at task 1322), such that the JOB control process 2100 of FIG. 21 is only performed when resuming delivery from a suspend delivery mode based on the user's current JOB.

The illustrated IOB monitoring process 2000 initializes or otherwise begins by obtaining, identifying or otherwise determining a desired minimum IOB threshold value for the user (task 2002). In accordance with one or more embodiments, the minimum JOB threshold value is user-configurable. For example, the patient or another user (e.g., a doctor or other trained medical personnel) may manipulate or otherwise operate an input user interface element 1120 to input or otherwise provide, to the monitoring application 1116, an IOB value below which the user would like to minimize his or her exposure to in order to avoid potential hyperglycemic rebound events. In response to receiving an input IOB protection value via a input user interface element 1120, the monitoring application 1116 may store or otherwise maintain the obtained JOB protection value in memory 1106 (e.g., in a dedicated register) for use as the minimum IOB threshold value. In other embodiments, the minimum IOB threshold value may be fixed and maintained in memory 1106 in a manner that does not allow the minimum IOB threshold value to be adjusted using the user interface element(s) 1120.

In yet other embodiments, the minimum IOB threshold value is calculated or otherwise determined by the monitoring application 1116 based on the nominal basal rate of insulin delivery that is or has been implemented by the command generation application 1114. For example, the monitoring application 1116 may calculate the minimum IOB threshold value by multiplying the nominal basal infusion rate by a conversion factor having a magnitude less than one (e.g., 0.2 or 20%) and then applying the final value theorem for the IOB resulting from that reduced basal rate to arrive at a corresponding steady-state IOB value, as described in greater detail below. It should be noted that in some embodiments, the monitoring application 1116 may continuously monitor the basal delivery rate implemented by the command generation application 1114 while in a normal closed-loop delivery mode and dynamically calculate the nominal basal delivery rate and the corresponding minimum IOB threshold value substantially in real-time, such that the minimum IOB threshold value reflects changes to the user's insulin response and/or insulin requirements over time. Additionally, in some embodiments, the monitoring application 1116 may account for manual boluses of insulin delivered in addition to the basal infusion rate to determine an overall nominal infusion rate for the user that reflects the user's historical insulin requirements. In alternative embodiments, a user may input or otherwise provide a minimum insulin infusion rate or a preprogrammed basal infusion rate, which may be utilized by the command generation application 1114 and/or the monitoring application 1116 to determine a corresponding minimum IOB threshold value. In yet other embodiments, the monitoring application 1116 may calculate the minimum IOB threshold value based on a minimum infusion rate imposed by the normal delivery mode implemented by the infusion device 502. Other factors that may be used to calculate a minimum IOB threshold value for a user may include, but are not limited to, the user's age, weight, fitness level, activity level, and/or other patient-specific characteristics or parameters.

Still referring to FIG. 20, the IOB monitoring process 2000 continues by obtaining, identifying or otherwise determining the current IOB for the user (task 2004). For example, in one or more embodiments, the monitoring application 1116 calculates or otherwise determines the user's current IOB based on any insulin delivered (e.g., the insulin automatically delivered as a result of the delivery control scheme implemented by the command generation application 1114 and any manually-initiated boluses of insulin) using the appropriate pharmacokinetics/pharmacodynamics model corresponding to the user's insulin response (e.g., using time constants corresponding to the user's insulin response). In other embodiments, the current IOB may be calculated by the command generation application 1114 or elsewhere within the control system 500 and/or the pump control system 520, 1100 and obtained therefrom by the monitoring application 1116. As described in greater detail below, depending on the embodiment, the current IOB may be calculated as the current IOB in the subcutaneous compartment, the current IOB in the plasma compartment plus the current IOB in the subcutaneous compartment, or the current IOB in the effect site compartment plus the current IOB in both the plasma compartment and the subcutaneous compartment. That said, the subcutaneous compartment will be the first of those compartments to be depleted of insulin after a prolonged period of zero insulin infusion, and accordingly, the subject matter may be described in the context of the current IOB in the subcutaneous compartment for purposes of explanation.

After obtaining the minimum IOB threshold value for the user and the current IOB value for the user, the IOB monitoring process 2000 compares the user's current IOB value to the minimum IOB threshold value to detect, identify, or otherwise determine whether the user's current IOB value is less than the minimum IOB threshold value (task 2006). When the user's current IOB value is greater than the minimum IOB threshold value, the IOB monitoring process 2000 maintains operating the infusion device in its current operating mode (task 2008). In this regard, if the command generation application 1114 and/or the motor control module 512 are currently implementing a suspend delivery mode and the monitoring application 1116 determines the user's current IOB value is greater than the minimum IOB threshold value, the monitoring application 1116 maintains the command generation application 1114 and/or the motor control module 512 in the suspend delivery mode, such that any delivery commands that would otherwise be generated by the command generation application 1114 are disabled or otherwise ineffectual (subject to the delivery resumption process 1300). Similarly, if the command generation application 1114 is currently implementing a closed-loop delivery mode and the monitoring application 1116 determines the user's current IOB value is greater than the minimum IOB threshold value, the monitoring application 1116 maintains the command generation application 1114 in the closed-loop delivery mode, such that any delivery commands generated by the command generation application 1114 are provided to the motor control module 512 without being modified or otherwise overridden.

When the user's current IOB value is less than the minimum IOB threshold value, the IOB monitoring process 2000 initiates operating the infusion device in an alternative (or adjusted) delivery mode configured to regulate the user's IOB to at least the minimum IOB threshold value (task 2010). In this regard, if the command generation application 1114 and/or the motor control module 512 are currently implementing a suspend delivery mode and the monitoring application 1116 determines the user's current IOB value is less than the minimum IOB threshold value, the monitoring application 1116 automatically signals, commands, or otherwise instructs the command generation application 1114 and/or the motor control module 512 to resume implementing a delivery mode in a similar manner as described above in the context of FIGS. 13-19. Additionally, in some embodiments, the monitoring application 1116 may also automatically operate an output user interface element 1120 to generate or otherwise provide a notification to the user that delivery is being resumed based on the user's current IOB falling below the user's minimum IOB threshold value, in a similar manner as described above in the context of FIGS. 13-19.

It should be noted that in some embodiments, when transitioning from the suspend delivery mode, the delivery mode initiated by the IOB monitoring process 2000 may be subject to the minimum suspension time period imposed by the automatic delivery suspension (e.g., task 1314), while in other embodiments, the IOB monitoring process 2000 may not be subject to the minimum suspension time period. Similarly, in some embodiments, after transitioning from the suspend delivery mode, the IOB monitoring process 2000 may be subject to the refractory time period imposed by the delivery suspension process 1200 (e.g., task 1206), such that the monitoring application 1116 maintains operation of the infusion device in the IOB control delivery mode for at least the minimum delivery time period even if the user's current IOB has met or exceeded the minimum IOB threshold value.

As described in greater detail below in the context of FIG. 21, in accordance with one or more embodiments, the difference between the user's current IOB and the minimum IOB threshold value is utilized to calculate or otherwise determine an alternative delivery command for regulating the user's current IOB to the minimum IOB threshold value. The alternative delivery command may be utilized to augment, adjust, or otherwise replace the normal delivery command generated in accordance with the normal delivery control mode implemented by the command generation application 1114 and/or pump control system 520, 1100. In some embodiments, the greater of the alternative delivery command and the normal delivery command may be provided to the motor control module 512. However, in alternative embodiments, the alternative delivery command may be weighted or otherwise combined with the normal delivery command to achieve an augmented delivery command that achieves a desired tradeoff between regulating the user's blood glucose and regulating the user's IOB. For example, the alternative delivery command and the normal delivery command may be averaged to achieve an augmented delivery command that balances regulating the user's blood glucose with regulating the user's IOB. The monitoring application 1116 maintains operation of the infusion device in a manner that is influenced by the alternative delivery command at least until the user's current IOB is greater than or equal to minimum IOB threshold value. Thereafter, the monitoring application 1116 may cause operation of the infusion device 502 to revert back to the suspend delivery mode pursuant to the delivery suspension process 1200 or otherwise maintain operation of the infusion device 502 in the normal delivery mode.

Figure 21:
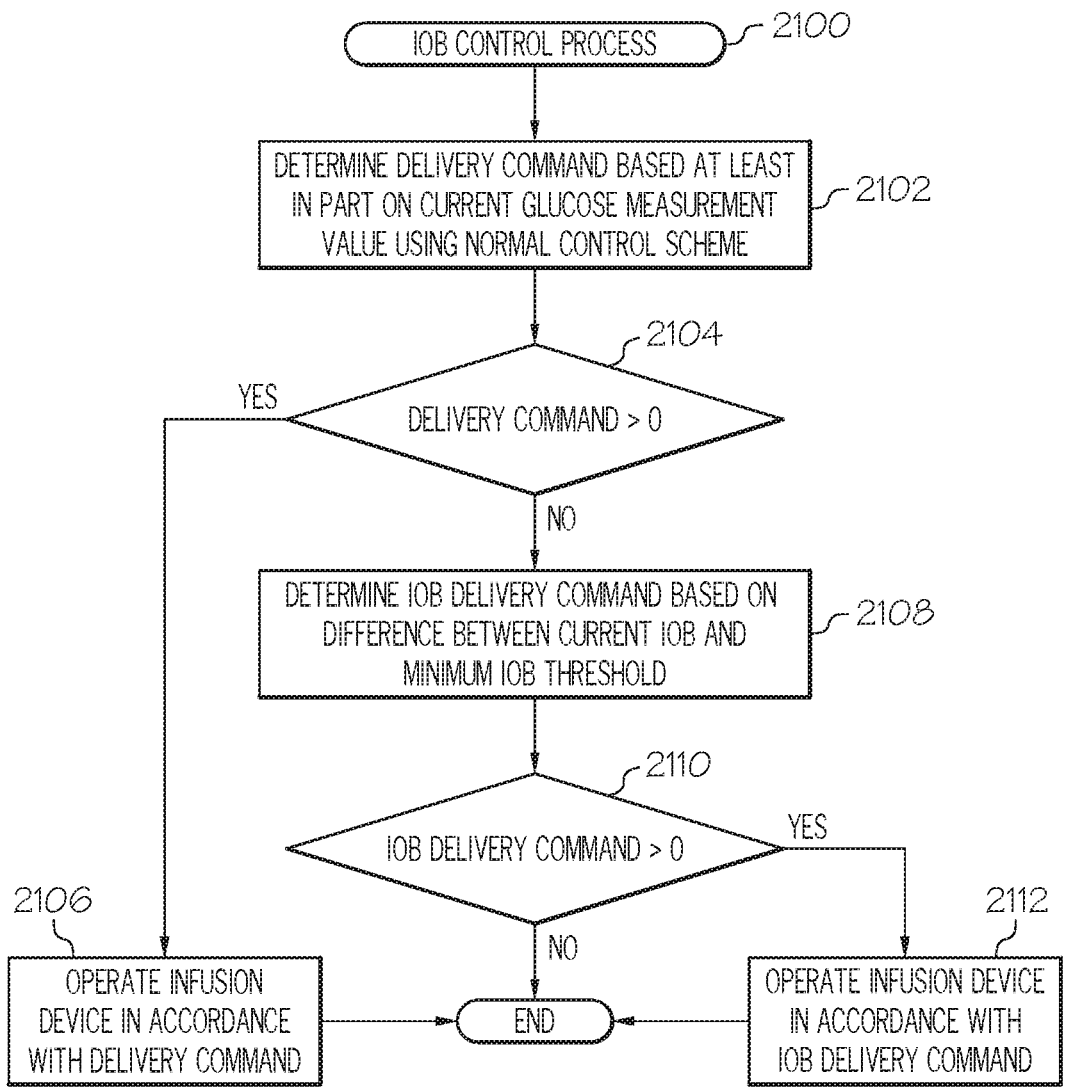
FIG. 21 depicts a flow diagram of an exemplary insulin on board control process suitable for use with the control system of FIG. 11 in conjunction with the insulin on board monitoring process of FIG. 20.

FIG. 21 depicts an exemplary IOB control process 2100 suitable for implementation by a control system associated with a fluid infusion device, such as the pump control system 520, 1100 in the infusion device 502, in conjunction with the IOB monitoring process 2000 to automatically regulate the user's IOB to a desired value (e.g., the minimum IOB threshold value). The various tasks performed in connection with the IOB control process 2100 may be performed by hardware, firmware, software executed by processing circuitry, or any combination thereof. For illustrative purposes, the following description may refer to elements mentioned above in connection with FIGS. 1-7 and 11. In practice, portions of the IOB control process 2100 may be performed by different elements of the control system 500, such as, for example, the infusion device 502, the sensing arrangement 504, the pump control system 520, 1100, the pump control module 1102, the motor control module 512, and/or the motor 507. It should be appreciated that the IOB control process 2100 may include any number of additional or alternative tasks, the tasks need not be performed in the illustrated order and/or the tasks may be performed concurrently, and/or the IOB control process 2100 may be incorporated into a more comprehensive procedure or process having additional functionality not described in detail herein. Moreover, one or more of the tasks shown and described in the context of FIG. 21 could be omitted from a practical embodiment of the IOB control process 2100 as long as the intended overall functionality remains intact.

In the illustrated embodiment, the IOB control process 2100 begins by obtaining, calculating or otherwise determining a baseline or reference delivery command for operating the infusion device based at least in part on the current glucose measurement value using the normal control scheme for when the infusion device is in a delivery mode (task 2102). In this regard, the command generation application 1114 may utilize the current glucose measurement value obtained via the sensing arrangement 504 in accordance with the normal control scheme implemented by the command generation application 1114. For example, the command generation application 1114 may determine a difference between the current glucose measurement value and a target glucose value (e.g., the glucose setpoint) and input or otherwise provide the difference to a closed-loop control system to obtain a closed-loop delivery command configured to regulate the current glucose measurement value to the target blood glucose value by minimizing the difference between the current glucose measurement value and the target value.

Figure 22:
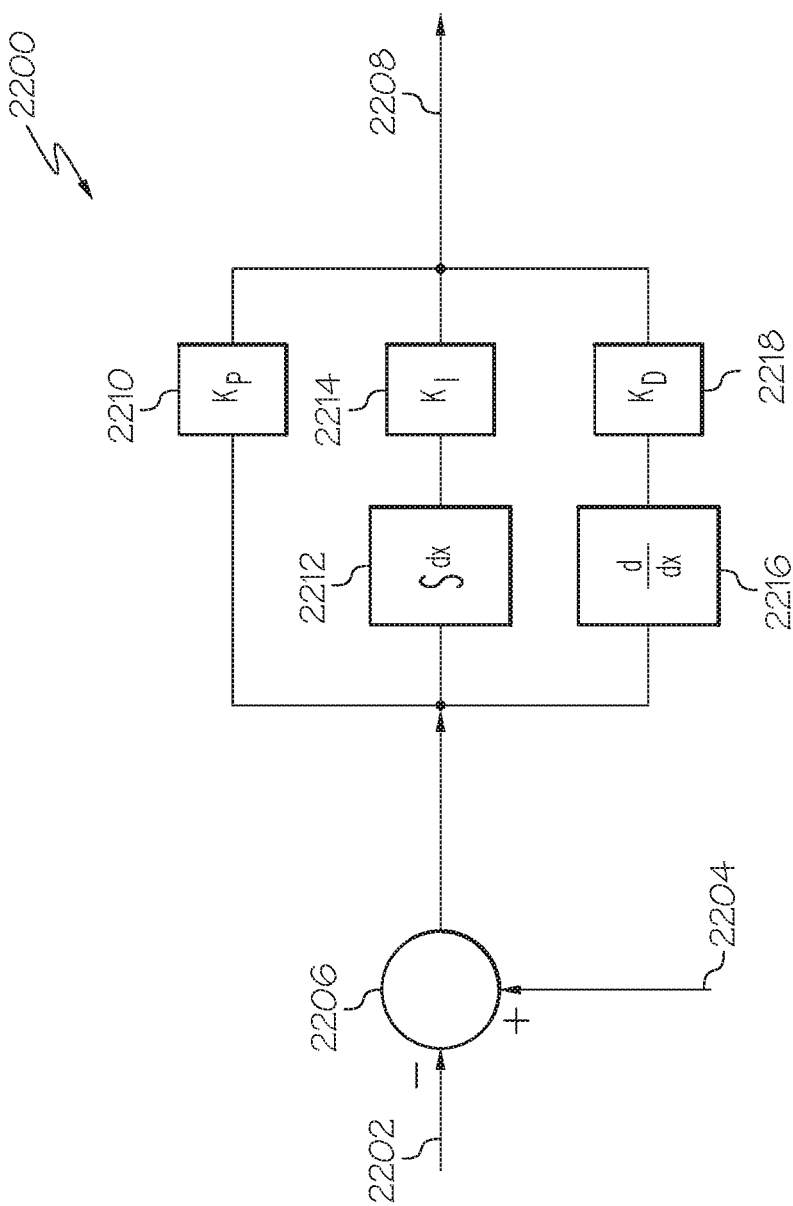
FIG. 22 is a block diagram of an exemplary closed-loop control system suitable for use with the control system of FIG. 11.

FIG. 22 depicts an exemplary embodiment of a closed-loop control system 2200 that may be implemented by the pump control system 520, 1100 and/or the command generation application 1114 associated with an infusion device 502 to operate the motor 507 of the infusion device 502 and regulate glucose levels in the body 518 of the user. It should be noted that FIG. 22 is a simplified representation of the closed-loop control system 2200 for purposes of explanation and is not intended to limit the subject matter described herein in any way. Practical embodiments of the closed-loop control system 2200 may include any number of control parameters configured to compensate, correct, or otherwise account for various operating conditions experienced and/or exhibited by the infusion device 502 and/or the sensing arrangement 504, such as, for example, one or more patient-specific control parameters (e.g., an insulin sensitivity factor, a daily insulin requirement, an insulin limit, a reference basal rate, a reference fasting glucose, an active insulin action duration, pharmacodynamical time constants, or the like). Various implementation details pertaining to determining gain coefficients and providing closed-loop control are described in greater detail in U.S. Pat. No. 7,402,153 or U.S. patent application Ser. No. 13/966,120, each of which is incorporated by reference herein in its entirety.

The closed-loop control system 2200 receives or otherwise obtains the target glucose value at input 2202. In exemplary embodiments, the target glucose value is stored or otherwise maintained in memory 1106, however, in some alternative embodiments, the target value may be received from an external component (e.g., CCD 106 and/or computer 108). The closed-loop control system 2200 receives or otherwise obtains the current glucose measurement value at input 2204 and calculates or otherwise determines the difference (or error signal) between the current glucose measurement value and the target glucose value at summation block 2206 (e.g., by subtracting the target glucose value from the current glucose measurement value). The difference output by the summation block 2206 is provided to each of a proportional term path, an integral term path, and a derivative term path. The proportional term path includes a gain block 2210 that multiplies the difference by a proportional gain coefficient, $K_P$, to obtain the proportional term. The integral term path includes an integration block 2212 that integrates the difference and a gain block 2214 that multiplies the integrated difference by an integral gain coefficient, $K_I$, to obtain the integral term. The derivative term path includes a derivative block 2216 that determines the derivative of the difference and a gain block 2218 that multiplies the derivative of the difference by a derivative gain coefficient, $K_D$, to obtain the derivative term. The proportional term, the integral term, and the derivative term are then added or otherwise combined to obtain a delivery command at output 2208, which, in turn, may be provided to the motor control module 512 for operating the motor 507. In exemplary embodiments, the delivery command at the output 2208 is configured to reduce or otherwise minimize the difference determined at the summation block 2206 to zero. In practice, the PID gain coefficients may be stored or otherwise maintained in memory 1106 for reference by the command generation application 1114 when generating the delivery command. In one embodiment, the integral gain coefficient may be equal to (or represented as) the proportional gain coefficient divided by an integral time $$\left(\text{e.g., } K_I = \frac{K_P}{\tau_I}\right)$$

while the derivative gain coefficient may be equal to the proportional gain coefficient multiplied by a derivative time constant (e.g., $K_D = \tau_D K_D$).

Referring again to FIG. 21, with continued reference to FIGS. 1-7, 11 and 22, the illustrated IOB control process 2100 continues by determining, verifying, or otherwise confirming whether or not the delivery command is greater than or equal to zero, and operating the infusion device in accordance with the normal delivery command when the delivery command is greater than zero (tasks 2104, 2106). In this regard, the delivery command generated by the closed-loop control system 2200 at the output 2208 will be greater than or equal zero when the current glucose measurement value from the sensing arrangement 504 at input 2204 is greater than or equal to the target blood glucose value at input 2202, in which case, the command generation application 1114 and/or the monitoring application 1116 enables or otherwise provides the delivery command at the output 2208 to the motor control module 512 to operate the motor 507 to deliver insulin to the body 518 of the user and regulate the user's glucose levels to the target value.

When the normal delivery command is less than zero, the IOB control process 2100 continues by calculating or otherwise determining an alternative delivery command for operating the infusion device based at least in part on the difference between the user's current IOB value and the minimum IOB threshold value (task 2108). In this regard, the alternative delivery command (also referred to herein as the IOB delivery command) is configured to regulate the user's current IOB to the minimum IOB threshold value, and thereby, reduce the likelihood of hyperglycemic rebound event after the user's glucose level begins to rise. As described in greater detail below, in an exemplary embodiment, an alternative closed-loop control system is implemented to regulate the difference between the user's current IOB value and the minimum IOB threshold value to be equal to zero.

The IOB control process 2100 continues by determining, verifying, or otherwise confirming whether or not the IOB delivery command is greater than or equal to zero, and operating the infusion device in accordance with the IOB delivery command when the IOB delivery command is greater than zero (tasks 2110, 2112). In this regard, the IOB delivery command generated by the command generation application 1114 and/or monitoring application 1116 will be greater than or equal zero when the user's current IOB value is less than or equal the minimum IOB threshold value, in which case, the command generation application 1114 and/ or the monitoring application 1116 enables or otherwise provides IOB delivery command to the motor control module 512 to operate the motor 507 to deliver insulin to the body 518 of the user and regulate the user's IOB to the minimum IOB threshold value. When both the normal delivery command and the IOB delivery command are less than zero, the IOB control process 2100 may terminate or exit without operating the infusion device to deliver insulin to the user (e.g., because both the user's blood glucose is below the target value and the user's current IOB is above the minimum IOB threshold).

It should be noted that FIG. 21 merely depicts one exemplary implementation of an IOB control process 2100, and in practice, the alternative IOB delivery command may be determined in any number of alternative manners. In this regard, in embodiments where both the normal delivery command and the IOB delivery command are greater than zero, the normal delivery command may be adjusted or otherwise modified using the IOB delivery command to achieve a desired tradeoff between regulating the user's blood glucose and regulating the user's JOB. For example, the normal delivery command and the IOB delivery command may be averaged together or otherwise combined using various weighting parameters and/or weighting functions to obtain an adjusted delivery command.

IOB Control

As described above in the context of FIGS. 20-21, to reduce the likelihood of hyperglycemic rebound events, the current IOB for the user is determined on a substantially continuous basis and monitored substantially in real-time to detect or otherwise identify when the user's IOB falls below a desired minimum threshold. In this regard, the current IOB is determined based on all insulin delivered, which includes manual boluses of insulin. Assuming an infusion rate $u_a(t)$ in units per hour (U/h), a pharmacokinetic model for the subcutaneous infusion of insulin is given by the following ordinary differential equations:

$$\dot{I}_S(t) = -\frac{1}{\tau_1} I_S(t) + \frac{1}{\tau_1} u_a(t),$$

$$\dot{I}_P(t) = -\frac{1}{\tau_2} I_P(t) + \frac{1}{\tau_2} I_S(t), \text{ and}$$

$$\dot{I}_E(t) = -\frac{1}{\tau_3} I_E(t) + \frac{1}{\tau_3} I_P(t),$$

where $I_S(t)$ corresponds to the subcutaneous compartment, $I_P(t)$ corresponds to the subcutaneous plus plasma compartment, $I_E(t)$ corresponds to the effect site compartment, $u_a(t)$ includes or otherwise accounts for both basal and bolus infusions, and the $\tau_n$ terms are the respective time constants associated therewith. For example, for a rapid-acting insulin such as aspart, $\tau_1 = 50/60$, $\tau_2 = 70/60$ h, and $\tau_3 = 55/60$ h.

The total insulin on board can be calculated using one or more of the compartments using equations:

$$IOB_1(t) = \int_0^t U_a(\tau)d\tau - \int_0^t I_S(\tau)d\tau,$$

$$IOB_2(t) = \int_0^t U_a(\tau)d\tau - \int_0^t I_P(\tau)d\tau, \text{ and}$$

$$IOB_3(t) = \int_0^t U_a(\tau)d\tau - \int_0^t I_E(\tau)d\tau,$$

where $IOB_1(t)$ corresponds to the insulin on board in the subcutaneous compartment, $IOB_2(t)$ corresponds to the insulin on board in the plasma compartment, and $IOB_3(t)$ corresponds to the insulin on board in all three compartments. These equations can be rewritten in the Laplace domain as:

$$IOB_1(s) = \frac{\tau_1}{(\tau_1 s + 1)} U_a(s),$$

$$IOB_2(s) = \frac{\tau_1 \tau_2 s + \tau_1 + \tau_2}{(\tau_1 s + 1)(\tau_2 s + 1)} U_a(s), \text{ and}$$

$$IOB_3(s) = \frac{\tau_1 \tau_2 \tau_3 s^2 + (\tau_1 \tau_2 + \tau_1 \tau_3 + \tau_2 \tau_3) s + \tau_1 + \tau_2 + \tau_3}{(\tau_1 s + 1)(\tau_2 s + 1)(\tau_3 s + 1)} U_a(s).$$

For purposes of explanation, the subject matter may be described herein in terms of the insulin on board in the subcutaneous compartment ($IOB_1$) because the subcutaneous compartment will be the first compartment to be depleted of insulin after prolonged periods of zero insulin infusion, and thus, is the first compartment to be maintained at the desired minimum JOB.

The minimum IOB threshold value for the insulin on board may be calculated based on the lowest desirable insulin infusion rate. For example, the minimum IOB threshold value for the IOB in the subcutaneous compartment may be calculated or otherwise determined using the equation $IOB_{min} = \tau_1 u_{min}$ by applying the final value theorem to the equation for $IOB_1(s)$, where $u_{min}$ corresponds to a steady state rate equal to the minimum desirable insulin infusion rate. As described above in the context of FIG. 20, the minimum desirable insulin infusion rate may be determined as a minimum insulin infusion rate input by a user or calculated based on the nominal basal delivery rate implemented by the command generation application 1114, a preprogrammed basal delivery rate, a historical average delivery rate for the user, or other historical data indicative of the user's insulin requirements. For example, if the nominal basal delivery rate is equal to 1 U/h, the monitoring application 1116 may multiply the nominal basal delivery rate by a factor of 0.2 to determine a minimum infusion rate of 0.2 U/h, resulting in a minimum IOB threshold value for the subcutaneous compartment equal to one sixth of a unit as a steady state result of the final value theorem. To regulate the current IOB in the subcutaneous compartment to the minimum IOB threshold value, a closed-loop proportional-integral control system may be configured to determine an IOB delivery command by implementing the following equation:

$$u_{IOB}(t) = K_{P_{min}} \left( e_{IOB}(t) + \frac{1}{\tau_{1_{min}}} \int_0^t e_{IOB}(\tau) d\tau \right),$$

where $e_{IOB}(t)$ is an error signal representing the difference between the current IOB and the minimum IOB threshold value (e.g., $e_{IOB}(t) = IOB_{min} - IOB_1(t)$), $K_{P_{min}}$ is the proportional gain coefficient for regulating the user's IOB to the minimum IOB threshold value, and $\tau_{1_{min}}$ is the integral time constant for regulating the user's IOB to the minimum IOB threshold value. In this regard, $K_{P_{min}}$ and $\tau_{1_{min}}$ may be tuned to achieve the desired response.

In alternative embodiments, instead of implementing a closed-loop proportional-integral control scheme to regulate the user's IOB to the minimum IOB threshold value, the IOB delivery command may be configured to provide a constant rate of infusion. For example, in one or more embodiments, the IOB delivery command may be fixed or otherwise set at a fraction of the basal delivery rate (e.g., 20% of the nominal basal delivery rate). In such embodiments, the response to the difference between the current IOB and the minimum IOB threshold value may be slower than it would be using the closed-loop proportional-integral control scheme (e.g., a longer amount of time required for the user's current IOB in the subcutaneous compartment to reach the minimum IOB threshold value), however, the complexity of implementation is reduced relative to the closed-loop control scheme.

As described above in the context of FIG. 21, the IOB delivery command ($u_{IOB}(t)$) is provided to the motor control module 512 when the user's current IOB is less than the minimum IOB threshold value to maintain the user's IOB at or near the minimum IOB threshold value and reduce the likelihood of a hyperglycemic event by preventing a total depletion of insulin on board. In this manner, the IOB control process 2100 in conjunction with the IOB monitoring process 2000 ensures the user has insulin on board, similar to healthy normal glucose tolerant users who generally always have insulin on board by virtue of healthy pancreatic function.

Figure 23:
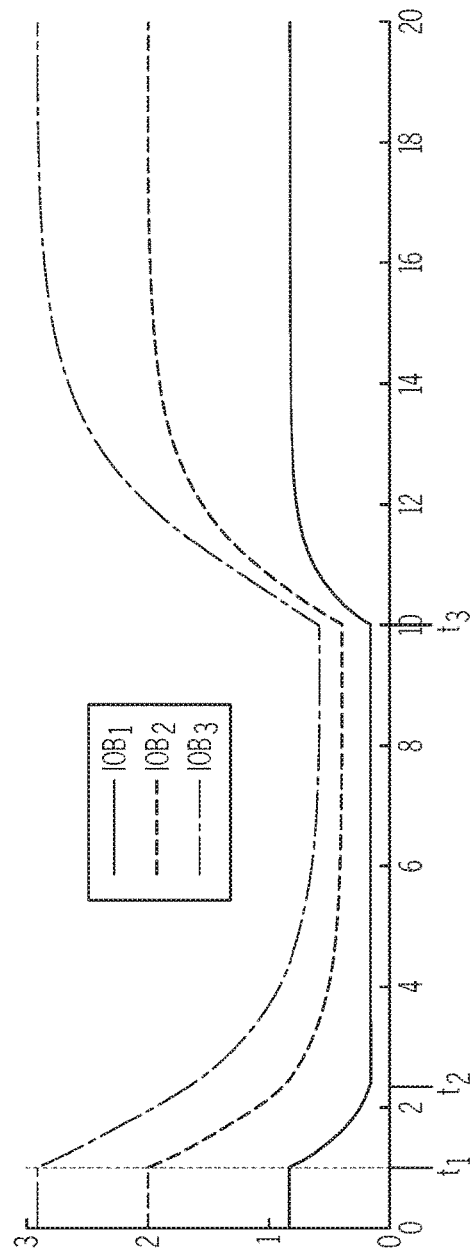
FIGS. 23-24 are graphs depicting exemplary relationships between insulin on board and insulin infusion rate for one exemplary embodiment of the insulin on board monitoring process of FIG. 20 in conjunction with the insulin on board control process of FIG. 21.
Figure 24:
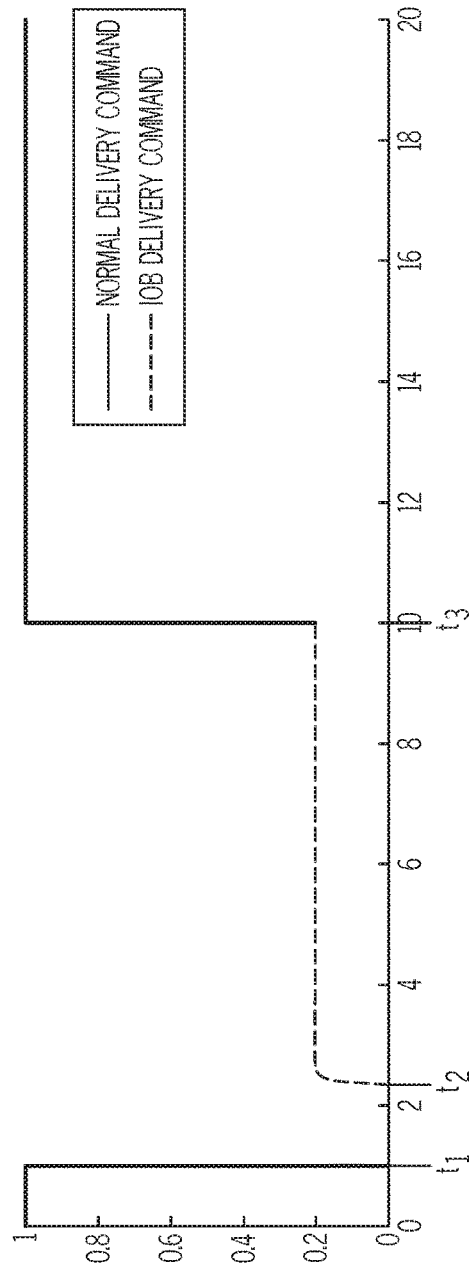

FIGS. 23-24 depict graphs of the IOB for the various compartments along with the corresponding infusion rate resulting from the IOB monitoring process 2000 of FIG. 20 and the IOB control process 2100 of FIG. 21 being implemented in conjunction with the delivery suspension process 1200 and the delivery resumption process 1300 of FIG. 13 using the above equations for determining the IOB delivery command. In this regard, FIGS. 23-24 depict a scenario where the nominal basal infusion rate is equal to 1 U/h, $u_{min}$=0.2 U/h (e.g., by multiplying the nominal basal delivery rate by a factor of 0.2), $\tau_1$=$^{50}$⁄$_{60}$ h, $IOB_{min}$=⅙ U for the subcutaneous compartment, $K_{P_{min}}$=20 h$^{-1}$, and $\tau_{1_{min}}$=1 h. As illustrated, after operating in the normal delivery mode for approximately one hour, the monitoring application 1116 may automatically suspend delivery at time $t_1$ based on the user's glucose values falling below their applicable suspend thresholds and/or the closed-loop control system 2200 implemented by the command generation application 1114 may generate delivery commands equal to zero based on the user's current glucose measurement value being less than the target glucose value. At time $t_2$, the monitoring application 1116 detects or otherwise identifies that the user's IOB in the subcutaneous compartment is less than or equal to the minimum IOB threshold value for the subcutaneous compartment (e.g., $IOB_{min}$=⅙ U), and thereafter, the command generation application 1114 and/or the monitoring application 1116 generates an alternative delivery command configured to regulate the user's IOB in the subcutaneous compartment to the minimum IOB threshold value (e.g., by providing an infusion rate of 0.2 U/h). Thereafter, at time $t_3$, when the monitoring application 1116 automatically resumes delivery based on the user's glucose values exceeding their applicable resume thresholds and/or the control scheme implemented by the command generation application 1114 generates delivery commands greater than zero (or greater than the IOB delivery command), the normal delivery commands are provided to the motor control module 512 and utilized to operate the motor 507 in lieu of the IOB delivery commands. As illustrated in FIG. 24, when the user's IOB in the subcutaneous compartment exceeds the minimum IOB threshold as a result of the increased infusion rate, the IOB delivery command generated based on the user's IOB is reduced to zero.

It should be noted that the IOB control described herein in the context of FIGS. 20-21 and FIGS. 23-24 may be utilized to augment or otherwise supplement the normal glucose control and/or the delivery suspension process 1200 in situations where the sensing arrangement 504 is providing invalid or unusable measurement values, providing erroneous low glucose measurement values, or is otherwise functioning improperly. In such situations, the likelihood of hyperglycemic events is reduced by ensuring that at least some minimum amount of IOB is present and being metabolized in the user's body.

Figure 25:
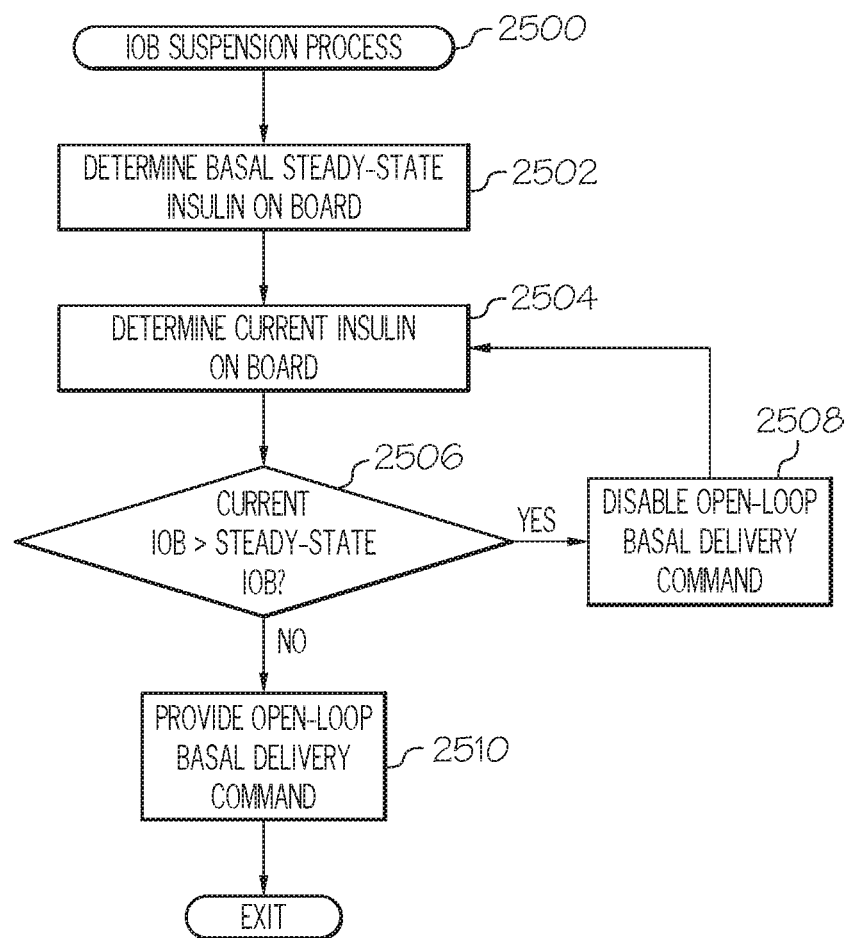
FIG. 25 depicts a flow diagram of an exemplary insulin on board suspension process suitable for use with the control system of FIG. 11.

FIG. 25 depicts an exemplary IOB suspension process 2500 suitable for implementation by a control system associated with a fluid infusion device, such as the pump control system 520, 1100 in the infusion device 502, in conjunction with an open-loop basal delivery mode to reduce the likelihood of a hypoglycemic event. The various tasks performed in connection with the IOB suspension process 2500 may be performed by hardware, firmware, software executed by processing circuitry, or any combination thereof. For illustrative purposes, the following description may refer to elements mentioned above in connection with FIGS. 1-7 and 11. In practice, portions of the IOB suspension process 2500 may be performed by different elements of the control system 500, such as, for example, the infusion device 502, the sensing arrangement 504, the pump control system 520, 1100, the pump control module 1102, the motor control module 512, and/or the motor 507. It should be appreciated that the IOB suspension process 2500 may include any number of additional or alternative tasks, the tasks need not be performed in the illustrated order and/or the tasks may be performed concurrently, and/or the IOB suspension process 2500 may be incorporated into a more comprehensive procedure or process having additional functionality not described in detail herein. Moreover, one or more of the tasks shown and described in the context of FIG. 25 could be omitted from a practical embodiment of the IOB suspension process 2500 as long as the intended overall functionality remains intact.

In exemplary embodiments, the IOB suspension process 2500 is performed upon entering an open-loop basal delivery mode to delay or otherwise suspend basal infusion in situations where there is sufficient insulin yet to be metabolized by the user and infusion of insulin may increase the likelihood of a hypoglycemic event. The IOB suspension process 2500 initializes or otherwise begins by obtaining, identifying or otherwise determining a basal steady-state IOB threshold value for the user (task 2502). In a similar manner as described above in the context of FIG. 20 with respect to the minimum IOB threshold value, the basal steady-state IOB threshold value may be user-configurable and stored or otherwise maintained in memory 1106. Alternatively, the basal steady-state IOB threshold value may be calculated or otherwise determined as the maximum IOB likely to result from delivery at the basal infusion rate. For example, the monitoring application 1116 may calculate the basal steady-state IOB threshold value by applying the final value theorem for the IOB resulting from that the nominal basal infusion rate (e.g., 1 U/h) to arrive at a corresponding steady-state IOB value. Again, in a similar manner as described above, the monitoring application 1116 may continuously monitor the basal delivery rate implemented by the command generation application 1114 while in a normal closed-loop delivery mode and dynamically calculate the nominal basal delivery rate and the corresponding basal steady-state IOB threshold value substantially in real-time and/or in a manner that accounts for manual boluses of insulin delivered in addition to the basal infusion rate.

The IOB suspension process 2500 continues by obtaining, identifying or otherwise determining the current IOB for the user (task 2504) in a similar manner as described above in the context of IOB monitoring process 2000 and comparing the user's current IOB value to the basal steady-state IOB threshold value to detect, identify, or otherwise determine whether the user's current IOB value is greater than the basal steady-state IOB threshold value (task 2506). In this regard, when the user's current IOB is greater than the basal steady-state IOB threshold value, the IOB suspension process 2500 continues by suspending or otherwise disabling the open-loop delivery commands (task 2508). In this regard, the loop defined by tasks 2504, 2506, and 2508 repeats indefinitely upon transitioning into the open-loop basal delivery mode from a closed-loop delivery mode until the current IOB is less than the basal steady-state IOB threshold value. When the user's current IOB is less than or equal to the basal steady-state IOB threshold value, the IOB suspension process 2500 enables or otherwise allows the open-loop delivery commands to be utilized to operate the motor of the infusion device to deliver fluid at the basal infusion rate (task 2510).

In alternative embodiments, the IOB suspension process 2500 may calculate or otherwise determine a duration of time for which the open-loop basal delivery commands should be suspended based on the difference between the user's current IOB and the basal steady-state IOB threshold value (e.g., the amount of time required for user's current IOB to exponentially decay to the basal steady-state IOB threshold value). In such embodiments, rather than repeating the loop defined by tasks 2504, 2506 and 2508, the IOB suspension process 2500 may suspend or otherwise disable the open-loop delivery commands for that amount of exponential decay time at task 2508 before enabling the open-loop delivery commands at task 2510.

Figure 26:
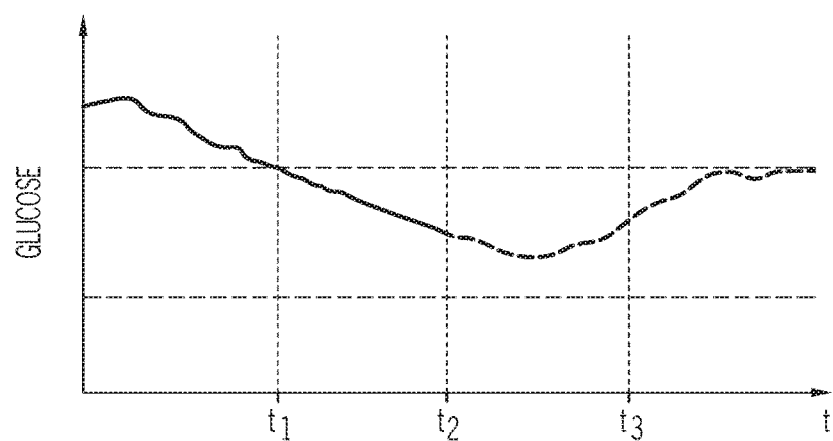
FIGS. 26-28 are graphs depicting exemplary relationships between glucose, insulin on board, and insulin infusion rate for one exemplary embodiment of the insulin on board suspension process of FIG. 25.
Figure 27:
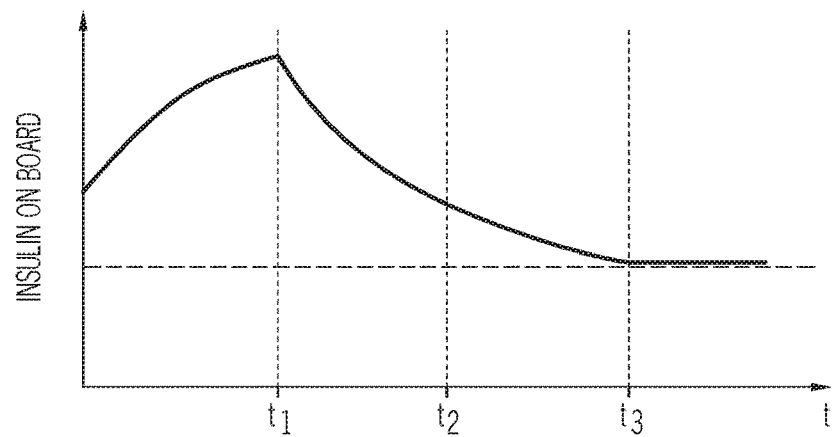
Figure 28:
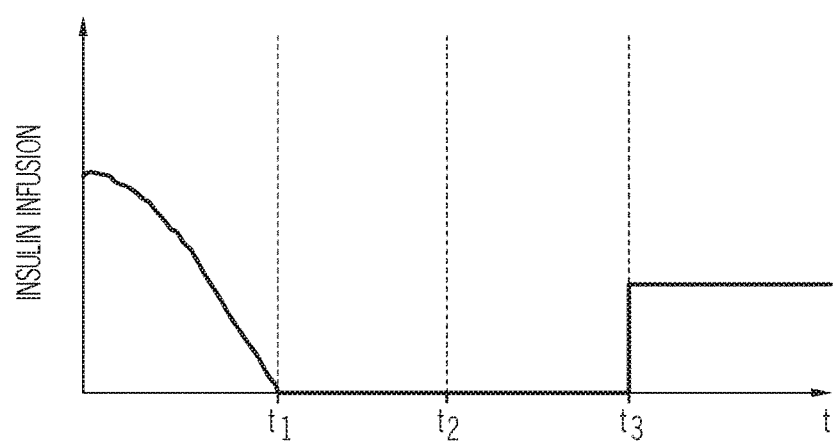

FIG. 26 depict graphs of a measured glucose value along with a corresponding graph of a user's IOB in FIG. 27, and FIG. 28 depicts a corresponding graph of the infusion rate implemented by the pump control system 520, 1100 in conjunction with the IOB suspension process 2500 of FIG. 25. Prior to $t_1$, when the user's current glucose measurement value is greater than the target glucose measurement value as depicted in FIG. 26, the closed-loop control system 2200 generates delivery commands based on the difference between the current glucose measurement value and the target glucose measurement value as depicted in FIG. 28, which increases the user's IOB as depicted in FIG. 27. After $t_1$, when the user's current glucose measurement value is less than the target glucose measurement value, the closed-loop control system 2200 generates delivery commands equal to zero. At time $t_2$, when the pump control system 520, 1100 determines that the infusion device 502 should be transitioned from the closed-loop delivery mode to an open-loop delivery mode (e.g., due to a failure to receive measurement values from the sensing arrangement 504), the IOB suspension process 2500 suspends or otherwise disables the open-loop delivery commands at time $t_2$ based on the user's current IOB being greater than the basal steady-state IOB threshold value, as depicted in FIGS. 27-28. In this regard, the IOB suspension process 2500 suspends or otherwise disables the open-loop delivery commands from time $t_2$ until time $t_3$ until the user's current IOB reaches the basal steady-state IOB threshold value before resuming the open-loop delivery commands at time $t_3$. As described above, in some embodiments, the duration of time that the open-loop delivery is suspended (e.g., $t_3-t_2$) may be calculated or otherwise predetermined based upon the difference between the user's current IOB and the basal steady-state IOB threshold value at time $t_2$. As illustrated in FIGS. 26-27, by virtue of the IOB suspension process 2500, the active IOB is metabolized and the downward trend in the user's glucose may be slowed or otherwise settled before enabling the basal insulin infusion, thereby reducing the likelihood of a hypoglycemic event.

For the sake of brevity, conventional techniques related to glucose sensing and/or monitoring, closed-loop glucose control, sensor calibration and/or compensation, and other functional aspects of the subject matter may not be described in detail herein. In addition, certain terminology may also be used in the herein for the purpose of reference only, and thus is not intended to be limiting. For example, terms such as "first", "second", and other such numerical terms referring to structures do not imply a sequence or order unless clearly indicated by the context. The foregoing description may also refer to elements or nodes or features being "connected" or "coupled" together. As used herein, unless expressly stated otherwise, "coupled" means that one element/node/feature is directly or indirectly joined to (or directly or indirectly communicates with) another element/node/feature, and not necessarily mechanically.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. For example, the subject matter described herein is not limited to the infusion devices and related systems described herein. Moreover, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application. Accordingly, details of the exemplary embodiments or other limitations described above should not be read into the claims absent a clear intention to the contrary.

What is claimed is:

1. An infusion device comprising:
    a motor operable to deliver fluid to a body of a user, delivery resulting in active fluid influencing a physiological condition in the body of the user; and
    a control module coupled to the motor to operate the motor to deliver the fluid based on a difference between a current measurement value for the physiological condition and a target value for the physiological condition when the current measurement value is greater than the target value, and when the current measurement value is less than or equal to the target value, wherein the control module is configured to:
        operate the motor to deliver the fluid to regulate a current amount of the active fluid in the body of the user to a lower threshold amount for the active fluid in the body of the user when the current amount is less than the lower threshold amount; and
        suspend operation of the motor when the current amount is greater than an upper threshold amount, and after suspending operation, automatically enable operation of the motor when the current amount of the active fluid in the body of the user is less than the lower threshold amount.

2. The infusion device of claim 1, the fluid comprising insulin, wherein:
    the current measurement value comprises a current glucose measurement value for the user;
    the lower threshold amount comprises a minimum insulin on board; and
    the upper threshold amount comprises a steady-state insulin on board resulting from a basal infusion rate.

3. The infusion device of claim 1, wherein the control module operates the motor to deliver the fluid to regulate the current amount of the active fluid by determining a delivery command using equation $$u_{IOB}(t) = K_{P_{min}}\left(e_{IOB}(t) + \frac{1}{\tau_{I_{min}}}\int_0^t e_{IOB}(\tau)d\tau\right),$$

where $u_{IOB}(t)$ represents the delivery command, $e_{IOB}(t)$ represents a difference between the current amount of the active fluid and the lower threshold amount, $K_{P_{min}}$ is a proportional gain coefficient for regulating the current amount of the active fluid, and $\tau_{I_{min}}$ is an integral time constant for regulating the current amount of the active fluid.

4. The infusion device of claim 1, further comprising:
    a user interface element to receive an input insulin on board protection value; and
    a data storage element, wherein the control module is coupled to the user interface element and the data storage element to store the input insulin on board protection value in the data storage element for use as the lower threshold amount.

5. The infusion device of claim 1, wherein the control module is configured to continuously monitor a basal delivery rate while in a normal closed-loop delivery mode, dynamically calculate a nominal basal delivery rate, and calculate the lower threshold amount based on the nominal basal delivery rate.

6. The infusion device of claim 1, wherein the control module maintains a closed-loop delivery mode when the current amount is greater than the lower threshold amount prior to initiating an alternative delivery mode to operate the motor to deliver the fluid to regulate the current amount of the active fluid in the body of the user to the lower threshold amount once the current amount is less than the lower threshold amount.

7. The infusion device of claim 1, wherein the control module maintains operation of the motor to deliver the fluid to regulate the current amount of the active fluid in the body of the user to the lower threshold amount for a refractory period prior to suspending operation of the motor.

8. The infusion device of claim 1, wherein the control module operates the motor to deliver the fluid to regulate the current amount of the active fluid in the body of the user to the lower threshold amount using an alternative closed-loop control system configured to regulate a difference between the current amount of the active fluid and the lower threshold amount to zero.

9. The infusion device of claim 1, further comprising:
    a user interface element to receive a basal steady-state insulin on board threshold value; and
    a data storage element, wherein the control module is coupled to the user interface element and the data storage element to store the basal steady-state insulin on board threshold value in the data storage element for use as the upper threshold amount.

10. The infusion device of claim 1, wherein the control module is configured to continuously monitor a basal delivery rate while in a normal closed-loop delivery mode, dynamically calculate a nominal basal delivery rate, and calculate the upper threshold amount based on the nominal basal delivery rate.

11. The infusion device of claim 1, wherein the control module disables open-loop delivery commands until the current amount is less than the upper threshold amount and enables the open-loop delivery commands to operate the motor when the current amount is less than the upper threshold amount.

12. The infusion device of claim 1, wherein the control module determines a duration of time for which operation of the motor should be suspended based on a difference between the current amount and the upper threshold amount.

13. An infusion device comprising:
a motor operable to deliver fluid to a body of a user, delivery resulting in active fluid influencing a physiological condition in the body of the user; and
a control module coupled to the motor to:
automatically suspend operation of the motor to deliver the fluid to the user based at least in part on a current measurement value for the physiological condition of the user;
determine a current amount of active fluid in the body of the user; and
after automatically suspending operation of the motor:
automatically resume operation of the motor to deliver the fluid to the user to regulate the current amount of active fluid to a lower threshold amount based on a difference between the current amount of active fluid and the lower threshold amount when the current measurement value for the physiological condition of the user is less than a threshold value for the physiological condition of the user; and
automatically suspend operation of the motor when the current amount of active fluid is greater than an upper threshold amount.

14. The infusion device of claim 13, the fluid comprising insulin, wherein:
the current measurement value comprises a current glucose measurement value for the user;
the lower threshold amount comprises a minimum insulin on board; and
the upper threshold amount comprises a steady-state insulin on board resulting from a basal infusion rate.

15. The infusion device of claim 13, the control module suspending operation of the motor based on the current measurement value, wherein the control module automatically enables operation of the motor when the current amount of the active fluid in the body of the user is less than the lower threshold amount.

16. The infusion device of claim 13, wherein the threshold value for the physiological condition of the user comprises a target value for a closed-loop operating mode.

17. The infusion device of claim 16, wherein the control module automatically resumes operation of the motor to deliver the fluid to the user to regulate the current amount of active fluid to the lower threshold amount based on the difference between the current amount of active fluid and the lower threshold amount when the current measurement value for the physiological condition of the user is less than the target value and the current amount of active fluid is less than at least one of the lower threshold amount and the upper threshold amount.

18. An infusion device comprising:
a motor operable to deliver fluid to a body of a user, delivery resulting in active fluid influencing a physiological condition in the body of the user; and
a control module coupled to the motor to:
determine a current amount of active fluid in the body of the user;
automatically suspend operation of the motor to the fluid upon transitioning to an open-loop mode from a closed-loop mode regulating a current measurement value for the physiological condition of the user to a target value when the current amount of active fluid is greater than an upper threshold amount; and
after automatically suspending operation of the motor, automatically resume operation of the motor to deliver the fluid to the user to regulate the current amount of active fluid to a lower threshold amount based on a difference between the current amount of active fluid and the lower threshold amount when the current amount of active fluid is less than the lower threshold amount.

19. The infusion device of claim 18, the fluid comprising insulin, wherein:
the current measurement value comprises a current glucose measurement value for the user;
the lower threshold amount comprises a minimum insulin on board; and
the upper threshold amount comprises a steady-state insulin on board resulting from a basal infusion rate.

* * * * *